United States Patent [19]

Grabiak et al.

[11] Patent Number: 5,000,775

[45] Date of Patent: Mar. 19, 1991

[54] 2-AMINO-4,5-DISUBSTITUTED-OXAZOLE/-THIAZOLE COMPOUNDS AS HERBICIDE ANTIDOTES

[75] Inventors: Raymond C. Grabiak, Maryland Heights; Robert K. Howe, Bridgeton; Len F. Lee, St. Charles, all of Mo.

[73] Assignee: Monsanto Company, St. Louis, Mo.

[21] Appl. No.: 815,102

[22] Filed: Dec. 31, 1985

[51] Int. Cl.$^5$ .................... A01N 43/00; A01N 43/02; A01N 43/64; A01N 37/00

[52] U.S. Cl. .................................. 71/88; 71/90; 71/93; 71/100; 71/118

[58] Field of Search ............... 71/88, 90, 93, 100, 71/118

[56] References Cited

U.S. PATENT DOCUMENTS

| | | | |
|---|---|---|---|
| 3,505,055 | 4/1970 | von Schmeling et al. | 71/90 |
| 3,542,801 | 11/1970 | Manning | 260/306.8 |
| 3,547,917 | 12/1970 | Kulka et al. | 260/247.1 |
| 3,879,351 | 4/1975 | Ariyan et al. | 424/270 |
| 3,933,838 | 1/1976 | Manghisi et al. | 260/306.8 |
| 4,199,506 | 4/1980 | Howe et al. | 548/201 |
| 4,284,426 | 8/1981 | Howe et al. | 71/90 |
| 4,303,439 | 12/1981 | Howe et al. | 71/88 |
| 4,308,391 | 12/1981 | Howe et al. | 548/194 |
| 4,437,876 | 3/1984 | Howe et al. | 71/90 |

Primary Examiner—Richard L. Raymond
Assistant Examiner—B. Bembenick
Attorney, Agent, or Firm—J. Timothy Keane; William I. Andress

[57] ABSTRACT

2-Amino-4,5-disubstituted-oxazole/thiazole compounds and antidotes for thiocarbamate, triazine and acetamide herbicides. These antidote compounds are especially effective to safen acetamide herbicides used to control grassy weeds in sorghum and broadleaf weeds in corn.

78 Claims, No Drawings

2-AMINO-4,5-DISUBSTITUTED-OXAZOLE/-THIAZOLE COMPOUNDS AS HERBICIDE ANTIDOTES

FIELD OF THE INVENTION

Herbicide antidotes are well-known crop protection chemicals. Of particular interest herein is a class of 2-amino-4,5-disubstituted-oxazole/thiazole compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

There are several classes of 2,4,5-substitutedthiazoles known as antidotes for herbicides. U.S. Pat. No. 4,199,506 and No. 4,437,876 to Howe et al describe 2-halo-4-substituted-5-thiazolecarboxylic acids and derivatives as antidotes for protecting corn, rice and sorghum from thiocarbamate herbicides such as triallate, or acetamide herbicides such as alachlor and acetochlor. U.S. Pat. No. 4,284,426 to Howe et al describes 2-chloro-4-substituted-5-thiazolemethyl-substituted compounds as antidotes for protecting sorghum treated with triallate, alachlor, butachlor or propachlor herbicides. U.S. Pat. No. 4,303,439 to Howe et al describes 2-substituted-4-substituted-5-oxazolecarboxylic acids/-esters as antidotes for protecting rice, sorghum or wheat from triallate, alachlor or butachlor herbicides. The 2-position of the thiazole ring is substituted by hydrido, alkoxy, halo or phenoxy groups. U.S. Pat. No. 4,308,391 to Howe et al describes 2-amino-4-substituted-5-thiazolecarboxylic acids and derivatives as intermediates for preparation of 2,4,5-substituted-thiazole antidote compounds such as shown in aformentioned U.S. Pat.s No. 4,199,506, No. 4,284,426 and No. 4,437,876.

Other classes of 2-aminothiazoles are known having various utilities. For example, U.S. Pat. No. 3,505,055 to von Schmeling describes 2-amino-4-methyl-5-carboxamido-thiazole compounds as plant growth regulants and as fungicides for coating and protecting crop seed. The 2-amino moiety is mentioned as substitutable by alkyl or phenyl groups. U.S. Pat. No. 3,542,801 to Manning describes 2-amino-4-(2-aminoethylamino)-5-halophenylthiazole compounds useful as hypotensive agents. There is no substitution shown for the 2-amino moiety. U.S. Pat. No. 3,547,917 to Kulka et al describes 2-amino-4-methylthiazole-5-carboxamides as fungicides and plant growth regulants. The 2-amino and 5-carboxamide moieties are mentioned a substitutable with many classes of radicals including alkyl, haloalkyl, cycloalkyl, alkenyl, phenyl, halophenyl and alkylphenyl. The Kulka et al '917 patent also mentions that N-heterocyclic groups may be substituted on the 2-amino nitrogen atom, such as furfuryl, α-pyridyl, or benzothiazolyl groups, or that the 2-amino nitrogen atom itself may be part of a heterocyclic ring such as a morpholido group. U.S. Pat. No. 3,879,531 to Ariyan et al describes 2-amino-4-methyl-5-thiazolecarboxamides for use as psychotherapeutic agents. The 2-amino moiety is shown as substitutable with methyl, ethyl or nitroso groups. The carboxamide nitrogen is shown as substitutable with hydrido, alkyl, phenyl or aralkyl groups. U.S. Pat. No. 3,933,838 to Manghisi et al describes 2-amino-4-aryl-5-substituted-thiazole compounds having various pharmacological properties, e.g., as antibacterial, anti-inflammatory, anti-ulcer, or antipyretic agents. The 2-amino moiety is mentioned as substitutable with alkyl, cycloalkyl, phenyl, halophenyl, alkylphenyl, alkoxyphenyl, or aralkyl groups. The thiazole 5-position substituents of Manghisi comprise a large class, all members of which are characterized in being attached to the thiazole 5-position carbon through one, two or three methylene carbons.

Weed control for corn and sorghum crops is one of the oldest and most highly developed areas in weed science. Thus, for a herbicide product to be accepted commercially, such herbicide product must provide a relatively high level of control of both grassy and broadleaf weeds in corn and sorghum, in addition to meeting several other criteria. For example, the herbicide must possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote having high safening activity suitable for a commercially-effective herbicide is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

DESCRIPTION OF THE INVENTION

A family of compounds useful as antidotes against herbicide injury to crop plants is provided by 2-amino-4,5-disubstituted-oxazole/thiazole compounds having the general structural formula

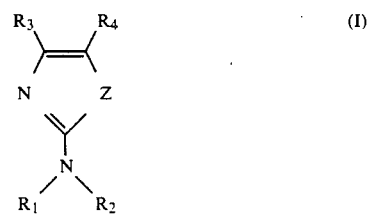

wherein Z is an oxygen atom or a sulfur atom; wherein each of R and Rz is independently selected from hydrido, alkyl, haloalkyl, hydroxyalkyl, monocycloalkyl, bicycloalkyl, tricycloalkyl, alkenyl, alkoxycarbonylalkyl, aryl and aralkyl, with the proviso that when Z is sulfur atom, $R_3$ and $R_2$ cannot both be hydrido; wherein each of $R_3$ and $R_4$ is independently selected from alkyl, alkoxy, hydroxyalkyl, alkoxyalkyl, haloalkyl, aryl, aralkyl, carboxylic acid derivatives and carbothioic acid derivatives selected from

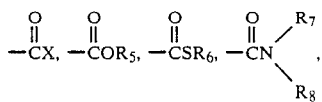

and oxazolyl or substituted oxazolyl of the formula

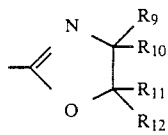

wherein X is halo, wherein each of $R_5$ and $R_6$ is independently selected from hydrido, alkyl, agriculturally-acceptable cations, alkoxyalkyl, aryl and aralkyl, wherein each of $R_7$ and $R_8$ is independently selected from hydrido, alkyl, hydroxyalkyl, alkoxyalkyl, aryl and aralkyl; wherein each of $R_1$ through $R_8$ is further independently selected from aryl and aralkyl substituted with one or more groups selected from alkyl, halo, haloalkyl, alkoxy, alkylthio, phenyl, phenoxy, phenylthio, dialkylamino, diphenylamino, cyano, nitro, carbamyl, acetamido and carboalkoxy; wherein each $R_9$ through $R_{12}$ is independently selected from hydrido, alkyl, hydroxyalkyl, alkoxy, alkoxyalkyl and halo; with the proviso that at least one of $R_3$ and $R_4$ must be selected from said carboxylic acid derivatives, said carbothioic acid derivatives, said oxazolyl and said substituted oxazolyl.

The compounds defined by formula I are believed to be novel with the further proviso that when Z is a sulfur atom and Ra is methyl, then $R_4$ cannot be

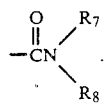

Where the term "alkyl" is used, either alone or within another term such as "haloalkyl", the term "alkyl" embraces linear or branched radicals having one to ten carbon atoms. The terms "monocycloalkyl", "bicycloalkyl" and "tricycloalkyl" embrace radicals having three to twenty carbon atoms. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl and perfluoroethyl groups. The terms "alkylol" and "hydroxyalkyl" embrace linear or branched alkyl groups having one to ten carbon atoms substituted with one or more hydroxyl groups. The term "alkenyl" embraces linear or branched radicals having two to ten carbon atoms and containing at least one carbon-carbon double bond. The terms "alkoxy" and "alkoxyalkyl" embrace linear or branched oxy-containing radicals having alkyl portions of one to ten carbon atoms, such as a methoxy group. The terms "carboalkoxy" and "alkoxycarbonyl" embrace alkoxy groups attached to a carbonyl radical, such as a carbethoxy group. The term "alkoxycarbonylakyl" embraces linear or branched radicals containing at least one oxy group and at least one carbonyl moiety separated by alkyl groups of one to ten carbon atoms and further characterized by the alkoxycarbonylalkyl radical being attached to the thiazole ring through the alkyl portion of the radical. The term "agriculturally-acceptable cations" embraces cations commonly used to form salts of the free acids, examples of such cations being alkali metal, alkaline earth, substituted amine and ammonium cations. The term "aryl" embraces univalent aromatic radicas such as phenyl and naphthyl. The term "aralkyl" embraces aryl-substituted alkyl radicals such as benzyl.

Also incuded in this invention are the stereo and optical isomers of compounds within the class defined by formula I.

Preferred antidotes within the class defined by formula I are compounds wherein the 2-amino moiety is substituted with one or two groups selected from linear and branched alkyl groups such as methyl, ethyl, n-propyl, isopropyl, n-butyl, sec-butyl, tert-butyl, n-pentyl, tert-pentyl, neopentyl, hexyl, heptyl, octyl, nonyl and decyl groups; monocycloalkyl groups such as cyclopropyl, cyclobutyl, cyclopentyl, cyclohexyl, cycloheptyl and cyclooctyl groups; alkenyl groups such as propenyl, butenyl and pentenyl; alkoxycarbonylalkyl groups such as 2-ethoxy-2oxoethyl and 2-propoxy-2-oxoethyl; phenyl; mono-, di- and tri- methyl substituted phenyl; mono-, di- and tri-fluoro substituted phenyl; and wherein the $R_3$ and $R_4$ substituents of formula I are independently selected from methyl, trifluoromethyl, hydroxycarbonyl, alkoxycarbonyl groups such methoxycarbonyl, ethoxycarbonyl and propoxycarbonyl, benzyloxycarbonyl, bromobenzyloxycarbonyl, trifluoromethylbenzyloxycarbonyl, chlorocarbonyl, phenyl, mono-, di- and tri-chlorophenyl, trifluoromethylphenyl, amido groups such as

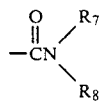

wherein each of $R_7$ and $R_8$ is independently selected from hydrido, alkyl of one to five carbon atoms and akylol of one to five carbon atoms, and oxazolyl groups such as

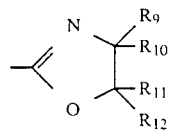

wherein each of $R_9$ through $R_{12}$ is independently selected from hydrido and alkyl of one to five carbon atoms.

Especially preferred compounds within formula I are 2-amino-4,5-disubstituted-oxazoles/thiazoles wherein each of $R_1$ and $R_2$ is independently selected from hydrido, methyl, ethyl, propyl, isopropyl, isobutyl, n-butyl, sec-butyl, tert-butyl, tert-pentyl, propenyl, cyclopentyl, phenyl and benzyl; wherein each of $R_3$ and $R_4$ is independently selected from trifluoromethyl, chlorophenyl, trifluoromethylphenyl,

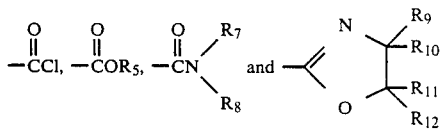

wherein $R_5$ is selected from hydrido, methyl, ethyl, benzyl, bromobenzyl and trifluoromethylbenzyl; wherein $R_7$ is hydrido; wherein $R_8$ is linear or branched alkylol of two to five carbon atoms; and wherein each of $R_9$ through $R_{12}$ is independently selected from hydrido, methyl and ethyl.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used with benefit in combination with an antidote of the described class include thiocarbamates, triazines and acetamides. Such combinations can be used to obtain selective weed control with low crop injury in several varieties of monocotyledonous crop plants such as corn, grain sorghum (milo), and cereals such as wheat, rice, barley, oats and rye, as well as several varieties of dicotyledonous crop plants including oil-seed crops such as soybeans and cotton.

Examples of thiocarbamate herbicides are the following:
cis-/trans-2,3-dichloroallyl-diisopropylthiolcarbamate (common name "diallate");
ethyl dipropylthiocarbamate (common name "EPTC");
2,3,3-trichloroallyl-diisopropylthiolcarbamate (common name "triallate");
S-ethyl diisobutyl(thiocarbamate) (common name "butylate");
S-propyl dipropyl(thiocarbamate) (common name "vernolate").

Examples of triazine herbicides are the following:
2-chloro-4,6-bis(ethylamino)-1,3,5-triazine (common name "simazine");
2-chloro-4-ethylamino-6-isopropylamino-sym-triazine (common name "atrazine");
2-chloro-4-(1-cyano)-1-methyl(ethylamino)-6-ethylamino-1,3,5-triazine (common name "cyanazine");

Examples of acetamide herbicides are the following:
2-chloro-N-isopropylacetanilide (common name "propachlor");
2-chloro-2'-(1,1-dimethylethyl)-6'-methyl-N-(methoxymethyl)acetanilide;
N-(butoxymethyl)-2-chloro-N-[2-(1,1-dimethylethyl)-6-methylphenyl]acetamide (common name "terbuchlor");
2-chloro-2',6'-diethyl-N-(methoxymethyl)acetanilide (common name "alachlor");
2-chloro-N-(isobutoxymethyl)-2',6'-acetoxylidide;
2-chloro-2',6'-diethyl-N-(butoxymethyl)acetamide (common name "butachlor");
2-chloro-N-(ethoxymethyl)-6'-ethyl-o-acetotoluidide (common name "acetochlor");
2-chloro-N-(2,6-dimethyl-1-cyclohexen-1-yl)-N(2-ethoxyethyl)acetamide;
ethyl ester of N-chloroacetyl-N-(2,6-diethylphenyl) glycine (common name "diethatyl ethyl");
2-chloro-N-(2,6-dimethylphenyl)-N-(2-methoxyethyl) acetamide (common name "dimethachlor");
2-chloro-N-(2-methoxy-1-methylethyl)-6'-ethyl-o-acetotoluidide (common name "metolachlor");
2-chloro-2',3'-dimethyl-N-(isopropyl)acetanilide;
2-chloro-2'-methyl-6'-methoxy-N-(propoxymethyl)acetanilide;
2-chloro-2'-methyl-6'-methoxy-N-(isopropoxymethyl) acetanilide;
2-chloro-2'-methyl-6'-ethoxy-N-(propoxymethyl)acetanilide;
N-(ethoxymethyl)-N-(2-ethyl-6-methyl-1-cyclohexen-1yl)-2-chloroacetamide;
N-(ethoxymethyl)-N-(2,5-dimethyl-1-cyclopenten-1-yl)-2-chloroacetamide;
2-chloro-2',6'-dimethyl-N-(1-pyrazol-1-ylmethyl)-acetanilide (common name "metazachlor");
2-chloro-N-(2,6-dimethyl-1-cyclohexen-1-yl)-N-(1H-pyrazol-1-ylmethyl)acetamide;
2-chloro-6'-trifluoromethyl-N-(isopropoxymethyl) acetanilide;
2-chloro-2'-methyl-6'-trifluoromethyl-N-(ethoxymethyl) acetanilide;
2-chloro-2'-trifluoromethyl-6-methyl-N-(propoxymethyl)acetanilide;
2-chloro-2'-methyl-6'-trifluoromethyl-N-(isopropoxymethyl)acetanilide;
2-chloro-2'-(3-methylbutoxy)-6'-methyl-N-(methyl)acetanilide;
2-chloro-2'-isobutoxy-6'-methyl-N-(propoxymethyl) acetanilide;
2-chloro-2'-methyl-6'-propoxy-N-(methyl)acetanilide;
2-chloro-2'-butoxy-6'-methyl-N-(methyl)acetanilide;
2-chloro-N-(ethoxymethyl)-N-[2-methyl-1-(1-methylethyl)1-propenyl]acetamide;
2-chloro-2'-ethyl-6'-(2-methylpropoxy)-N-(ethoxymethyl)acetanilide;
2-chloro-2'-methyl-6'-(1-methylbutoxy)-N-(methyl)acetanilide;
2-chloro-2'-ethyl-6'-(1-methylpropyl)-N-(methyl)acetanilide;
2-chloro-2'-(1,3-dimethylbutoxy)-6'-methyl-N(methyl)acetanilide;
2-chloro-2'-methyl-6'-(1-methylpropyl)-N-(methyl)acetanilide;
2-chloro-2'-ethyl-6'-trifluoromethyl-N-(1-pyrazolyl1-ylmethyl)acetanilide;
2-chloro-N-isopropyl-1-(3,5,5-trimethylcyclohexen-1-yl) acetamide (common name "trimexachlor");

Several of the mentioned herbicides are known in the art. Diallate and triallate herbicides are described in U.S. Pat. Nos. 3,330,643 and No. 3,330,821. Atrazine herbicide is described in U.K. Patent No. 814,947. Alachlor, butachlor and acetochlor herbicides are described in U.S. Pat. No. 3,442,945 and U.S. Pat. No. 3,547,620. Propachlor herbicide is described in U.S. Pat. No. 2,863,752 and Reissue Pat. No. 26,961. Metolachlor herbicide is described in U.S. Pat. No. 3,937,730. Metazachlor herbicide is described in U.S. Pat. No. 4,249,935. Trimexachlor herbicide is described in U.S. Pat. No. 4,319,918. U.S. Pat. No. 4,351,667 describes the herbicides N-(ethoxymethyl)-N-(2-ethyl-6-methyl-1-cyclohexen-1-yl)-2-chloroacettamide and N-(ethoxymethyl)-N-2-(2,5-dimethyl-1-cyclopenten-1-yl)-2-chloroacetamide. U.K. Pat. No. 2,072,175 describes the herbicide 2-chloro-2'-methyl-6'-methoxy-N-(isopropoxymethyl)acetanilide. U.K. Pat. No. 2,072,181 describes the herbicide 2-chloro-2'-methyl-6' trifluoromethyl-N-(ehtoxymethyl)acetanilide.

Combinations may be made of any one or more of the described antidote compounds with any one or more of the herbicide compounds mentioned herein.

Antidote compounds of the described class are effective to reduce herbicidal injury to grain sorghum (milo), wheat, rice, soybean and corn, especially where herbicide injury is associated with pre-emergent application of the herbicides. Antidote compounds of the invention have been found particularly effective to reduce injury to sorghum caused by alachlor herbicide. Also, the antidote compounds are particularly effective to reduce injury to corn caused by the acetamide herbicides acetochlor and 2-chloro-2'-methyl-6'-methoxy-N-(isopropoxymethyl)acetanilide, both of which are highly active acetanilide herbicides.

Acetochlor is especially suitable for use in corn for control of a greater variety of grassy and broadleaf weeds than typically provided by the commercial herbicide alachlor. Antidotes from the class defined by formula I, above, in combination with acetochlor have been found to have many advantages over alachlor for control of troublesome grassy and broadleaf weeds in corn. For example, these antidote+acetochlor combinations effectively control broadleaf weeds, such as velvetleaf, as well as grassy weeds, while alachlor does not consistently control such broadleaf weeds. Surprisingly, antidotes within the formula I class, above, reduce injury to corn due to acetochlor, without interfering with the efficacy of acetochlor as a herbicide in corn. In addition to broader spectrum weed control, acetochlor provides several other advantages over alachlor, namely, higher unit activity, lower application rates in most soils and higher activity in high organic matter soils. For those weeds controlled effectively by both acetochlor and alachlor, acetochlor provides equivalent weed control at about one-half the application rate of alachlor. This lower effective application rate for acetochlor translates into substantially lower exposure of the environment to the herbicide. By use of one of the above-described antidotes in combination with acetochlor, all of these advantages of acetochlor are available to improve corn production at a lower unit cost.

Antidote Compound Preparation

The 2-amino-4,5-disubstituted-oxazole/thiazole compounds of the invention may be prepared by one or more of the following general procedures:

Procedure I:

A primary or secondary amine or amine salt may be reacted with a 2-chloro-4,5-disubstituted oxazole/thiazole compound without solvent, or in an organic solvent such as toluene, ethyl ether or acetonitrile, at a temperature in a range from about $-77°$ C. to about $200°$ C., to provide a 2-amino-4,5-disubstituted oxazole/thiazole compound:

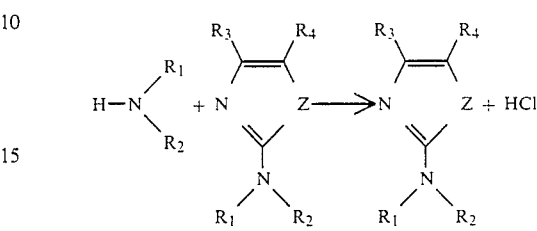

wherein each of $R_1$ through $R_4$ and $Z$ is independently selected from the groups described before. Particularly-preferred substituents are those wherein $R_1$ and $R_2$ are independently selected from hydrido; linear or branched alkyl; alkoxycarbonylalkyl having three to ten carbon atoms in total; phenyl; benzyl; halophenyl such as chlorophenyl and difluorophenyl; alkylphenyl such as mono- or di-methylphenyl; alkoxyphenyl such as methoxyphenyl; and haloalkylphenyl such as trifluoromethylphenyl. In all these preferred groups, the term "alkyl" preferably embraces groups having one to ten carbon atoms.

Procedure II:

A chloro-keto ester may be condensed with urea, thiourea, or an N-substituted or N,N-disubstituted urea or thiourea, without solvent, or in an organic solvent such as dimethylformamide or methanol, at a temperature in a range from about $25°$ C. to about $180°$ C., to provide an N-substituted or N,N-disubstituted 2-amino-4,5-disubstituted oxazole/thiazole compound:

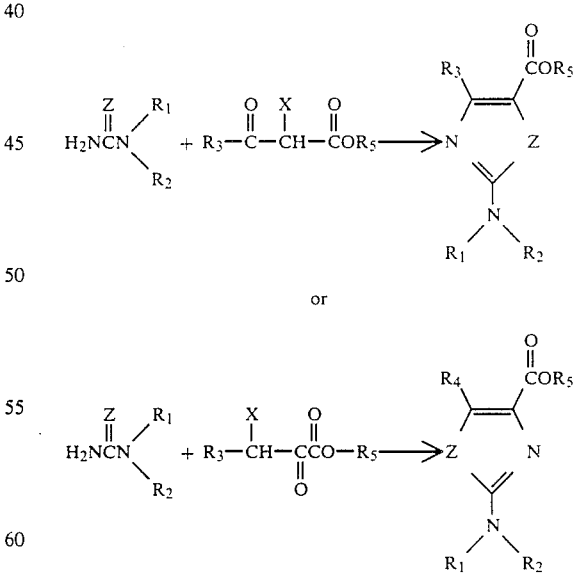

wherein each of $R_1$ through $R_5$ and $Z$ is independently selected from the groups described before. Particularly-preferred substituents are those wherein each of $R_1$ and $R_2$ is independently selected from hydrido, linear or branched alkyl of one to ten carbon atoms, especially groups such as tert-butyl, phenyl, benzyl, monocycloalkyl of five to ten carbon atoms, such as cyclopentyl and cyclohexyl, tricycloalkyl of nine to eighteen carbon atoms, such as adamantyl, alkenyl of two to eight carbon atoms, and haloalkylphenyl such as trifluoromethylphenyl; wherein $R_3$ is selected from alkyl of one to ten carbon atoms, and haloalkyl such as trifluoromethyl and perfluoroethyl; and wherein $R_5$ is alkyl of one to ten carbon atoms.

Procedure III:

The 2-amino-4,5-oxazole/thiazole-carboxylic acid ester compounds of Procedures I or II may be hydrolyzed in the presence of aqueous sodium hydroxide and in an organic solvent such as tetrahydrofuran at a temperature ranging from about 0° C. to about 100° C., to provide the corresponding 2-amino-4,5- oxazole/-thiazole carboxylic acid compound:

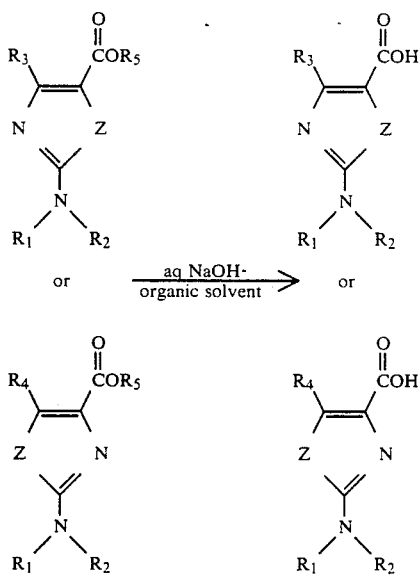

wherein each of $R_1$ through $R_5$ and Z is independently selected as described under Procedures I and II, above.

Procedure IV:

The 2-amino-4,5-oxazole/thiazole-carboxylic acid compounds of Procedure III may be reacted with excess thionyl chloride, and optionally with a catalytic amount of dimethylformamide at reflux to provide the corresponding 2-amino-4,5-oxazole/thiazole-carboxylic acid chloride compound which may be converted to the corresponding ester with an alcohol:

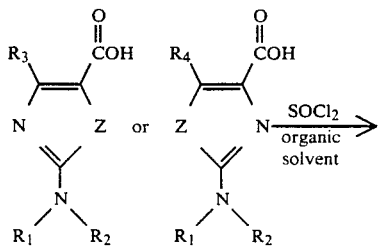

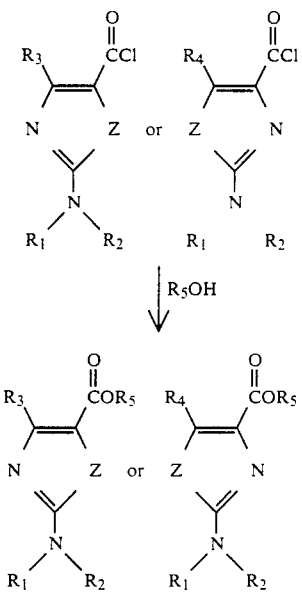

wherein each of $R_1$ through $R_5$ and Z is independently selected as described under Procedures I and II, above.

Procedure V:

The 2-amino-4,5-oxazole/thiazole-carboxylic acid chlorides of Procedure IV may be reacted with an amien or an aminoalcohol in an organic solvent such as methylene chloride or ethyl ether, and optionally with an acid scavenger such as triethylamine, at a temperature in a range from about −30° C. to about 100° C., to provide an N-hydroxyalkyl-2-amino-4,5-oxazole/-thiazole-carboxamide compound:

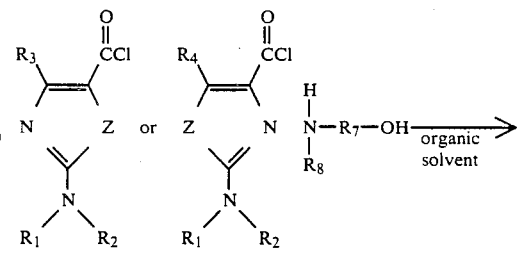

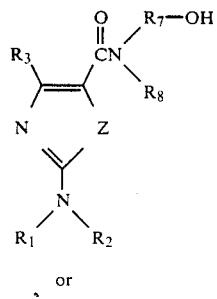

or

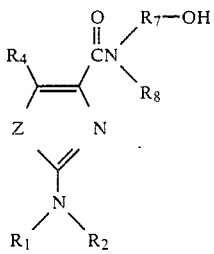

wherein each of $R_1$ through $R_3$ and Z is independently selected as described in Procedures I and II, above; wherein $R_7$ is selected from linear or branched alkyl groups having one to ten carbon atoms and the hydroxyl group may be attached to any carbon atom of the alkyl group; and wherein $R_8$ is hydrido, or a suitable substituent as described herein.

Procedure VI:

The 2-amino-4,5-oxazole/thiazole-carboxamidoalkylol compounds of Procedure V may be reacted with thionyl chloride, at a temperature in a range from about $-33°$ C. to about $100°$ C., and the product then treated with aqueous sodium hydroxide, at a temperature in a range from about $-33°$ C. to about $100°$ C., to provide a 2-amino-4,5-oxazole/thiazole-(2-oxazoline) compound:

wherien each of $R_1$ through $R_4$ and Z is independently selected as described in Procedures I and II above; wherein $R_7$ is as described in Procedure V and $R_8$ is hydrido; and wherien each of $R_9$ through $R_{12}$ preferably is independently selected from alkyl groups of one to five carbon atoms.

Procedure VII:

The 2-amino-4,5-oxazole/thiazole-carboxylic acid compound of Procedure III may be reacted with a halo/haloalkyl-substituted benzyl halide in the presence of potassium carbonate in an organic solvent such as dimethylformamide, at a temperature in a range from about $-33°$ C. to about $100°$ C., to provide a 2-amino 4,5-oxazole/thiazole-carboxylic acid benzyl ester compound:

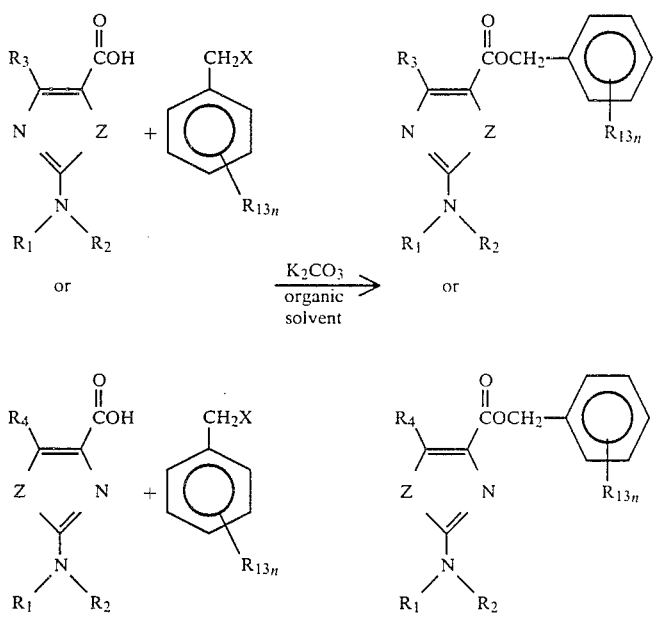

wherein each of $R_1$ through $R_4$ and Z is independently selected as described in Procedures I and II above; wherein X is halo, preferably chloro, bromo or iodo; and wherein $R_{13n}$ is selected from halo, preferably fluoro, chloro, or iodo, and haloalkyl, preferably trifluoromethyl or perfluoroethyl, and n is an integer selected from one through five.

Procedure VIII:

Any of the mono-N-substituted-2-amino-4,5-substituted-oxazole/thiazole compounds of Procedures I-VII may be further substituted at the N-amino-position by reaction with an alkyl halide in the presence of sodium hydride in an organic solvent such as tetrahydrofuran, at a temperature in a range from about $-30°$ pound:

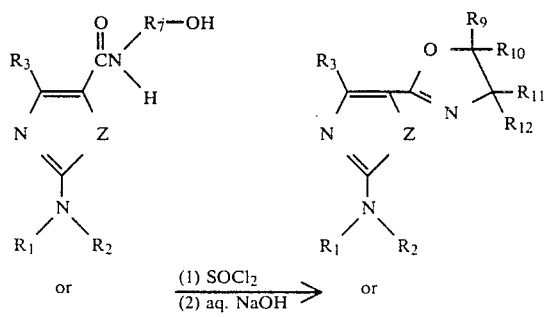

C. to about 0° C., to provide a di-N-substituted-2-amino 4,5-substituted oxazole/thiazole compound:

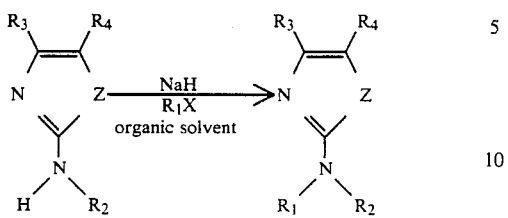

wherein each of $R_1$, $R_2$, $R_3$, $R_4$, X and Z is independently selected as described in Procedures I and II, above.

Procedure IX:

An excess of a primary or secondary amine may be reacted with a 2-halo-4,5-disubstituted oxazole/thiazole compound to provide a 2-amino-4,5-disubstituted oxazole/thiazole carboxamide compound:

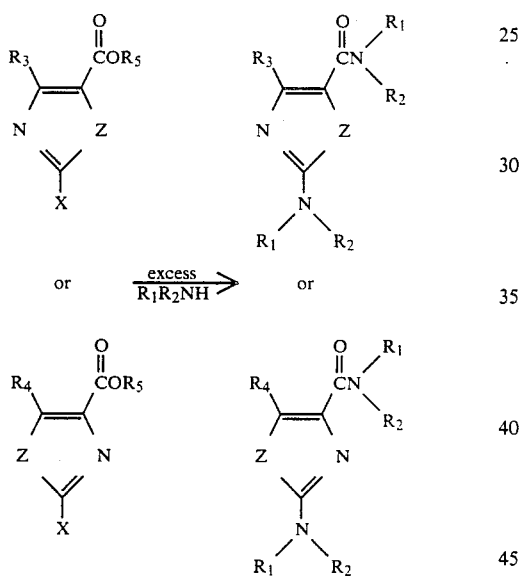

wherein Each or $R_1$, $R_2$, $R_3$, $R_4$, $R_5$ and Z is independently selected as described in Procedures I and II, above.

In any of the foregoing Procedures I - IX, for those oxazole/thiazole compounds having a 4- or 5- position carboxylic moiety, it is understood that counterpart compounds may be made having a 4- or 5-position carbothioic moiety.

The following examples are presented for illustrative purposes only and are not intended as a restriction on the scope of the invention. All parts are by weight unless otherwise indicated. Most of the commercially-available starting materials were obtained from Aldrich Chemical Co., Milwaukee, Wis. The substituted-oxazole/thiazole starting materials were prepared as generally described in U.S. Pat. Nos. 4,199,506 and No. 4,303,439. Table I sets forth analytical data for specific compounds prepared in accordance with the procedures of Examples 1-60.

EXAMPLE 1

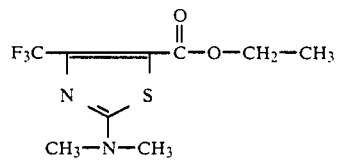

Ethyl 2-dimethylamino-4-trifluoromethyl-5-thiazolecarboxylate

To a vessel containing 591 g of ethyl ether cooled in a dry ice-acetone bath was added 12.5 g of dimethylamine with stirring. Then, to a reaction vessel cooled in a dry-ice acetone bath there was placed 11.5 g of the previously-prepared dimethylamine-in-ether solution followed by addition of 5.79 g (23 mmol) of ethyl 2-chloro-4-trifluoromethyl-5-thiazolecarboxylate in 20 ml of ethyl ether. A white precipitate formed immediately. The reaction mixture was stirred for 10 minutes and filtered. The ether filtrate was washed with 5% sodium hydroxide, dried over anhydrous calcium sulfate and concentrated under reduced pressure. The residual solid was treated with petroleum ether and filtered to provide 4.0 g of white solid product (m.p. 78°-79° C.) identified in Table I.

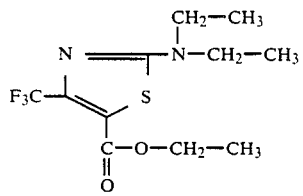

EXAMPLE 2

Ethyl 2-diethylamino-4-trifluoromethyl-5-thiazolecarboxylate

A reaction vessel was charged with 96.4 g (400 mmol) of ethyl 2-hydroxy-4-trifluoromethyl-5-thiazolecarboxylate and 117 g (766 mmol) of phosphorus oxychloride and then cooled in an ice bath. To the cooled mixture was added 40 g of diethylamine. The reaction mixture was heated at reflux at 163° C. with stirring for about 14 hours. Excess phosphorus oxychloride was removed under reduced pressure. The residue was poured into ice water and a solid precipitate was collected. The solid precipitate was dissolved in ethyl ether, washed with 5% sodium hydroxide, dried with calcium sulfate, and concentrated under reduced pressure to provide 50 g of residue. This residue was subjected to Kugelrohr distillation (100°-120° C. @ 0.5 mm Hg) to provide 3.5 g of a yellow liquid identified in Table I.

EXAMPLE 3

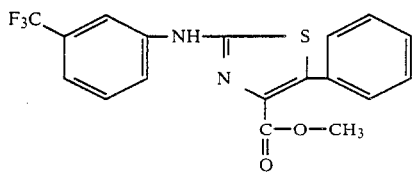

Methyl 5-phenyl-2-{[3-(trifluoromethyl)phenyl]amino}4-thiazolecarboxylate

A reaction vessel was charged with 2.8 g of methyl 5-phenyl-2-chloro-4-thiazolecarboxylate and 9.7 g of meta-aminobenzotrifluoride. The reaction mixture was stirred overnight and then heated and stirred at 150° C. for about 6 hours during which time a crystalline solid appeared. The mixture was treated with ethyl ether and water. The ether extract was dried with magnesium sulfate and concentrated. The residue was crystallized from anhydrous ethyl ether to provide a white amorphous powder (m.p. 147°–149° C.) identified in Table I.

EXAMPLE 4

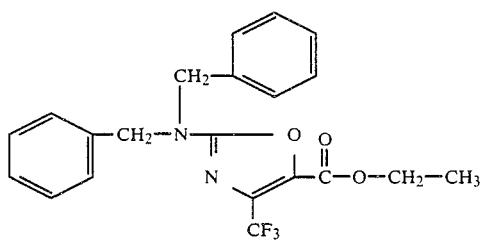

Ethyl 2-[bis(phenylmethyl)amino]-4-trifluoromethyl-5-oxazolecarboxylate

A reaction vessel was charged with 7.2 g (30 mmol) of dibenzylurea and 2.18 g (10 mmol) of 2-chloro-4,4,4-trifluoroacetoacetate. The reaction mixture was stirred and heated at 140°–150° C. for 18 hours under a calcium sulfate drying tube. After the mixture cooled to room temperature, the resultant solid material was diluted with methylene chloride, then washed three times with water, dried over sodium sulfate, and concentrated under reduced pressure to provide 7.8 g of an off-white solid material. This solid material was stirred in hot ethyl ether, cooled, and filtered to remove starting urea compound. The filtrate was concentrated under reduced pressure to provide a beige-colored solid which was then dissolved in hot carbon tetrachloride. This solution cooled and additional urea precipitated which was collected. The filtrate was concentrated under reduced pressure to provide 4.2 g of a light-orange glass. This glass was triturated in cyclohexane and filtered to yield 1.6 g of white needle-like crystal material (m.p. =90°–92° C.). The filtrate was concentrated under reduced pressure and the resulting off-white solid material was extracted with hot petroleum ether. The ether extract was decanted from an orange oil, reduced in volume and then cooled to provide 0.9 g of an off-white needle-crystal material (m.p.=89°–92° C.). The material was collected and the filtrate was concentrated under reduced pressure to provide 0.55 g of an off-white solid material which was allowed to stand overnight on a clay plate. The solid material was recrystallized from hexane at −76° C. to provide 0.45 g of white solid material (m.p.=90°–92° C.). A total amount of 2.95 g of white solid material was recovered as identified in Table I.

EXAMPLE 5

(Procedure I)

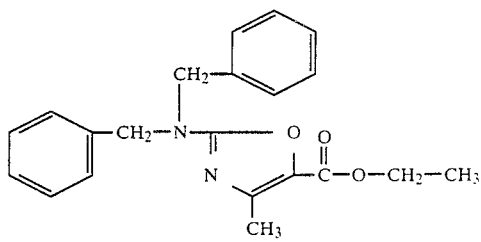

Ethyl 2-[bis(phenylmethyl)amino]-4-methyl-5-oxazolecarboxylate

A reaction vessel fitted with a calcium sulfate drying tube was charged with 5 ml of toluene, 0.56 g (2 mmol) of ethyl 2-iodo-4-methyl-5-oxazolecarboxylate and 2 ml (10 mmol) of dibenzylamine. The reaction mixture was stirred overnight at room temperature. The reaction mixture was then heated at reflux for 4 hours, cooled, and then diluted with ethyl ether. The mixture was washed with water, then with 5% hydrochloric acid, and then with water. The ether solution was dried with sodium sulfate and then concentrated under reduced pressure to yield 0.4 g of a yellow glass. This glass was dissolved in hot hexane and then with the vessel cooling in a dry ice bath, a white solid material was deposited. The solid material was filtered off giving 0.35 g of product (m.p.=75°–77° C.) identified in Table I.

EXAMPLE 5

(Procedure II)

A reaction vessel fitted with a calcium sulfate drying tube was charged with 3.05 g (22 mmol) of ethyl 2-chloroacetoacetate and 6.4 g (27 mmol) of 1,1-dibenzylurea. The reaction mixture was stirred and heated at 140°–150° C. for 19 hours to yield a black tar product which was dissolved in methylene chloride, then washed with saturated aqueous sodium bicarbonate, followed by three washings with water. The methylene chloride extract was dried over sodium sulfate and then concentrated under reduce pressure to provide 7.6 g of a dark brown oil. This oil was subjected to Kugelrohr distillation (200° C. @ 1.5 mm Hg) to remove volatile starting materials and by-products. The yellowish undistilled pot residue was then dissolved in hot petroleum ether. Upon cooling of this solution in an acetone-ice bath, 4.15 g of a beige solid material was deposited. This solid material was dissolved in hot hexane and filtered hot. This solution cooled and 3.45 g of a beige crystalline solid product (m.p.=73°–76° C.) was recovered as identified in Table I. NMR/GLC analysis confirmed that the products of Procedures I and II of Example 5 were identical.

EXAMPLE 6

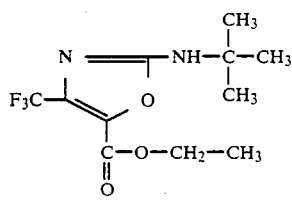

Ethyl 2-[(1,1-dimethylethyl)amino]-4-trifluoromethyl-5-oxazolecarboxylate

A reaction vessel was charged with 10.9 g (50 mmol) of ethyl 2-chloro-4,4,4-trifluoroacetoacetate and 7.0 g (60 mmol) of tert-butylurea. The reaction mixture was stirred and heated at 140°-150° C. for 19 hours under a calcium sulfate drying tube. With the mixture at room temperature, the mixture was slurried in methylene chloride and washed three times with water. The methylene chloride extract was dried over magnesium sulfate and then concentrated under reduced pressure to yield 8.8 g of a mustard-colored solid material. This solid material was dissolved in hot hexane and then filtered hot. The filtrate was cooled in a dry ice bath. The filtrate yielded 7.3 g of a beige solid product (m.p.=56°-59° C.) identified in Table I.

EXAMPLE 7

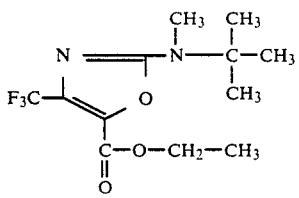

Ethyl 2-[(1,1-dimethylethyl)methylamino]-4-trifluoromethyl-5-oxazolecarboxylate A 50% oil dispersion of sodium hydride (0.38 g; 7.9 mmol) was washed three times with petroleum ether under a nitrogen atmosphere. The oil-free sodium hydride was suspended in 15 mol anhydrous tetrahydrofuran in a reaction vessel cooled in an ice bath. Then, with the sodium hydride suspension at 0° C. and stirred, there was added dropwise 25 ml anhydrous tetrahydrofuran containing 2.0 g (7.15 mmol) of ethyl 2-[(1,1-dimethylethyl)amino]-4-trifluoromethyl-5-oxazolecarboxylate (as prepared in Example 6. The reaction mixture was stirred for ½ hour at 0° C. and then 15 ml of anhydrous tetrahydrofuran containing 2.54 g (20 mmol) of methyl iodide was added dropwise to the mixture. The reaction mixture was stirred at room temperature for 3 hours. An additional 0.2 g (4 mmol) of 50% oil dispersion of sodium hydride (washed as before) was added and the mixture was stirred at room temperature for one hour. The reaction mixture was heated at reflux for 45 minutes, then stirred overnight at ambient temperature. The mixture was partitioned between ethyl ether and 5% hydrochloric acid solution. The organic phase was dried with sodium sulfate and concentrated under reduced pressure to yield 2.1 g of a reddish-brown product which was subjected to Kugelrohr distillation (100°-120° C. @ 2.5 mm Hg) to yield 1.7 g of a brown oil. This brown oil was dissolved in methylene chloride, washed with 10% sodium bisulfite, and concentrated under reduced pressure to yield 1.3 g of a colorless oil which was subjected to Kugelrohr distillation (100° C. @ 4 mm Hg) to yield 1.25 g of a pale yellow oil identified in Table I.

EXAMPLE 8

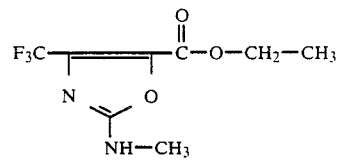

Ethyl 2-(methylamino)-4-trifluoromethyl-5-oxazolecarboxylate

By the procedure of Example 4, 4.45 g (60 mmol) of methylurea was reacted with 10.9 g (50 mmol) of ethyl 2-chloro-4,4,4-trifluoromethylacetoacetate. The product mixture was treated with methylene chloride, washed with water, dried and concentrated. The residue was recrystallized from toluene to yield 6.7 g of a pale yellow needle-crystal product (m.p.=136°-138° C.) identified in Table 1.

EXAMPLE 9

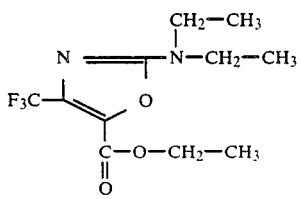

Ethyl 2-(diethylamino)-4-trifluoromethyl-5-oxazolecarboxylate

To a reaction vessel containing a stirred mixture of 3.15 g (13 mmol) of ethyl 2-chloro-4-trifluoromethyl-5-oxazolecarboxylate in 25 ml of toluene, there was added 3 ml (29 mmol) of diethylamine. The reactionmixture was stirred at ambient temperature for 4 hours and then suction filtered. The filtrate was washed with 5% hydrochloric acid, then with saturated brine, then dried over sodium sulfate and concentrated under reduced pressure to yield 3.3 g of a pale yellow oil. This oil was subjected to Kugelrohr distillation (60° C. @ 3 mm Hg) to remove trace amounts of starting material. Further Kugelrohr distillation provided 2.9 g of colorless oil (b.p. 110° C. @ 3 mm Hg) identified in Table I.

EXAMPLE 10

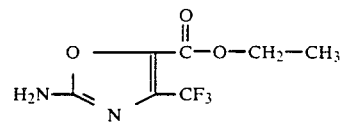

Ethyl 2-amino-4-(trifluoromethyl)-5-oxazolecarboxylate

A mechanically-stirred mixture of 53.2 g (0.885 mol) of urea and 38.6 g (0.177 mol) of ethyl α-chloro-γ,γ,γ-trifluoroacetoacetate was reacted in 50 ml dry dimethylformamide at 100°-110° C. for 71 hours. The reaction mixture was cooled to ambient temperature and the resulting orange slurry was poured into 500 ml of water and then cooled in an ice bath. Suction filtration of the mixture provided a mustard-colored solid material which when dried under an infrared lamp yielded 26.0 g of material. This solid material was slurried in hot chloroform, then cooled in an ice bath to yield 22.1 g of beige plate-like crystal material (m.p. 193–195° C.). A second crystal crop was obtained after concentration of the slurry residue, recrystallization in hot ether and filtration through glass wool. Total yield was 22.4 g of crystal product (m.p.=193°–195° C.) identified in Table 1.

EXAMPLE 11

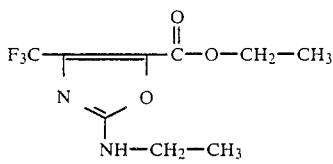

Ethyl 2-(ethylamino)-4-(trifluoromethyl)-5-oxazolecarboxylate

By the procedures of Example 4, 5.3 g (60 mmol) of ethyl urea was reacted with 10.9 g (50 mmol) of ethyl 2-chloro-4,4,4-trifluoroacetoacetate at 140°-150° C. for 24 hours. The product mixture was treated with methylene chloride, washed with water, dried and concentrated. The residue was recrystallized from methylcyclohexane to yield 8.0 g of crystal product (m.p.=89°-90° C.) identified in Table I.

EXAMPLE 12

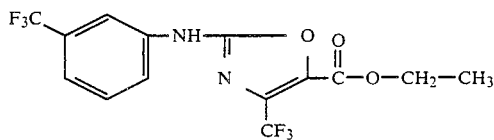

Ethyl 2-{[3-trifluoromethyl)phenyl]amino}-4-(trifluoromethyl)-5-oxazolecarboxylate To a stirred solution of 75 ml ethyl ether containing 9.7 g (0.04 mol) of ethyl 2-chloro-4-trifluoromethyl-5-oxazolecarboxylate, there was added 12.9 ml (0.08 mol) of meta-amino benzotrifluoride. The reaction mixture was stirred at ambient temperature for 5 days. The product mixture was filtered and the filtrate was treated with ethyl ether, washed with 5% hydrochloric acid, dried over magnesium sulfate, and concentrated under reduced pressure. The residue was recrystallized from methylene chloride to yield 6.6 g of crystal product (m.p.=158°-160° C.) identified in Table I.

EXAMPLE 13

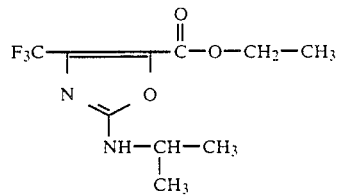

Ethyl 2-[(1-methylethyl)amino]-4-(trifluoromethyl)-5-oxazolecarboxylate

By the procedure of Example 4, 6.1 g (60 mmol) of isopropyl urea was reacted with 10.9 g (50 mmol) ethyl 2-chloro-4,4,4-trifluoroacetoacetate at 140°-150° C. for 24 hours. The product mixture was treated with methylene chloride, washed with water, dried and concentrated. The residue was recrystallized from methylcyclohexane to yield 6.3 g of crystal product (m.p.=51°-52° C.) identified in Table I.

EXAMPLE 14

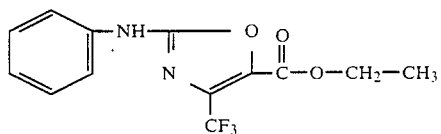

Ethyl 2-(phenylamino)4(trifluoromethyl)-5-oxazolecarboxylate

By the procedure of Example 4, 8.2 g (60 mmol) of phenyl urea was reacted with 10.9 g (50 mmol) of ethyl 2-chloro-4,4,4-trifluoroacetoacetate at 140°-150° C. for 24 hours. The product mixture was treated with methylene chloride, washed with water, dried and concentrated. The residue was recrystallized from methylcyclohexane to yield 6.2 g of crystal product (m.p.=114°-116° C.) identified in Table I.

EXAMPLE 15

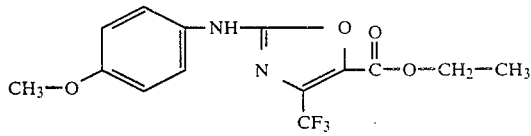

Ethyl 2-[(4-methyloxyphenyl)amino-4-(trifluoromethyl)-5-oxazolecarboxylate

To a stirred solution of 100 ml toluene containing 7.3 g (0.03 mol) of 2-chloro-4-trifluoromethyl-5-oxazolecarboxylate, there was added 19.8 g (0.06 mol) of para-anisidine. The reaction mixture was stirred at reflux for 72 hours. A dark brown solid product was obtained which was slurried in ethyl ether, washed with 5% hydrochloric acid or 25% sulfuric acid, dried with magnesium sulfate, and concentrated under reduced pressure to yield 9.2 g of a thick brown oil. This oil was subjected to Kugelrohr distillation (80° C. @ 0.5 mm Hg) to yield 6.0 g of a yellow solid which when recrystallized from carbon tetrachloride yielded 4.2 g of white solid product (m.p.=124°-125° C.) identified in Table I.

EXAMPLE 16

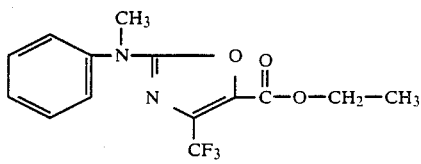

Ethyl 2-(methylphenylamino)-4-(trifluoromethyl)-5-oxazolecarboxylate

By the procedure of Example 15, 4.29 g (0.04 mol) of N-methyl aniline was added to 75 ml of toluene containing 4.87 g (0.02 mol) of 2-chloro-4-trifluoromethyl-5-oxazolecarboxylate. The reaction mixture was stirred at reflux for 72 hours. The product mixture was slurried in ethyl ether, washed with water and 25% sulfuric acid, dried and concentrated. The residue was distilled and the distillate recrystallized from a chloroformmethylcyclohexane solution to yield 3.5 g of a white-powder product (m.p.=78°-81° C.) identified in Table I.

EXAMPLE 17

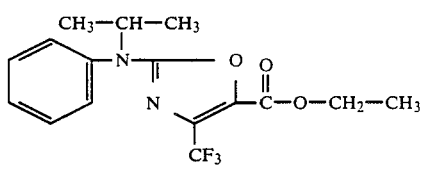

Ethyl 2-[(1-methylethyl)phenylamino]-4-(trifluoromethyl)-5-oxazolecarboxylate

By the procedure of Example 15, 2.59 g (0.019 mol) of N-isopropyl aniline was reacted neat with 2.32 g (0.0095 mol) of ethyl 2-chloro-4-trifluromethyl-5-oxazolecarboxylate at 140°-150° C. for 4 hours. The product mixture was slurried in ethyl ether, washed with 25% sulfuric acid and water, dried and concentrated. The residue was distilled and the distillate was recrystallized from methylcyclohexane to yield 0.7 g of a white-powder product (m.p.=66°-68° C.) identified in Table 1.

EXAMPLE 18

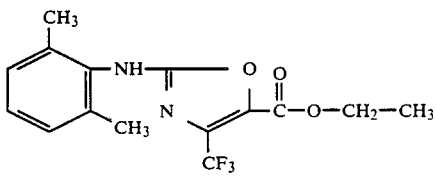

Ethyl 2-[(2,6-dimethylphenyl)amino]-4-(trifluoromethyl)-5-oxazolecarboxylate

By the procedure of Example 15, 4.84 g (0.04 mol) of 2,6-dimethyl aniline was added to a stirred solution of 75 ml toluene containing 4.87 g (0.02 mol) of 2-chloro-4-trifluoromethyl-5-oxazolecarboxylate. The reaction mixture was stirred at reflux for 24 hours. The product was separated, distilled and then recrystallized from petroleum ether to yield 1.99 g of crystal product (m.p.=79°-81° C.) identified in Table I.

EXAMPLE 19

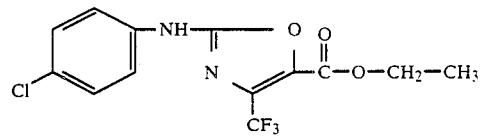

Ethyl 2-[(4-chlorophenyl)amino]-4-)trifluoromethyl)-5-oxazolecarboxylate

By the procedure of Example 15, 3.57 g (0.028 mol) of para-chloro-aniline was reacted neat with 3.41 g (0.014 mol) of ethyl 2-chloro-4-trifluoromethyl-5-oxazolecarboxylate at 145°-155° C. for 5 hours. The product was separated and then recrystallized from a chloroform-methylcyclohexane mixture to yield 1.65 g of a light brown solid product (m.p.=195°-197° C.) identified in Table I.

EXAMPLE 20

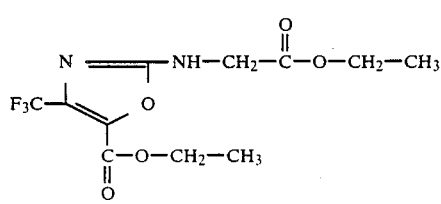

Ethyl 2-[(2-ethoxy-2-oxoethyl)amino]-4-(trifluoromethyl)-5-oxazolecarboxylate

By the procedure of Example 15, 4.19 g (0.03 mol) of glycine ethyl ester hydrochloride was added to a mixture of 100 ml toluene containing 4.87 g (0.02 mol) of ethyl 2-chloro-4-trifluoromethyl-5-oxazolecarboxylate and 6.07 g (0.06 mol) of triethylamine. The reaction mixture was stirred at ambient temperature for 48 hours. The product was separated and then recrystallized from methylcyclohexane to yield 3.55 g of a yellow powder product (m.p.=62°-63° C.) identified in Table I.

EXAMPLE 21

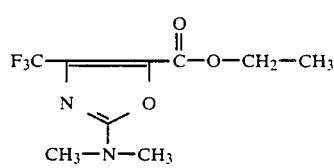

Ethyl 2-(dimethylamino)-4-(trifluoromethyl)-5-oxazolecarboxylate

A reaction vessel was charged with 4.17 g (0.03 mol) of para-nitrophenol, 50 ml of dry dimethylformamide containing dimethylamine as impurity, and potassium carbonate. After stirring of this mixture at ambient temperature, there was added 4.86 g (0.02 mol) of ethyl 2-chloro-4-trifluoromethyl-5-oxazolecarboxylate. The reaction mixture was stirred at ambient temperature for 24 hours. The resulting yellow mixture was extracted with ethyl ether and water. The organic phase was washed five times successively with 5% sodium hydroxide and five times with water, then dried with magnesium sulfate, and concentrated under reduced pressure to yield 2.2 g of a yellow solid which was recrystallized in methylcyclohexane to yield 1.7 g of a white powder. Chromatographic separation on silica gel using dichloroethane as eluent yielded 0.96 g of a light yellow powder product (m.p.=53°-55° C.) identified in Table I.

EXAMPLE 22

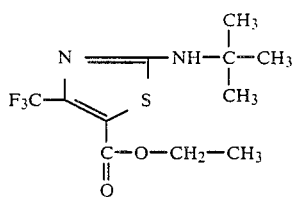

Ethyl 2-[(1,1-dimethylethyl)amino]-4-(trifluoromethyl)-5-thiazolecarboxylate

A stirred mixture of 2.6 g (10 mmol) of ethyl 2-chloro-4-trifluoromethyl-5-thiazolecarboxylate and ml of tert-butylamine was heated at reflux for 20 hours. The mixture was diluted with ethyl ether and washed twice with water. The ether phase was dried with magnesium sulfate and concentrated under reduced pressure to yield 2.85 g of a beige solid material which was recrystallized from methylcyclohexane to yield 2.4 g of a white plate crystal product (m.p.=104°-106° C.) identified in Table 1.

EXAMPLE 23

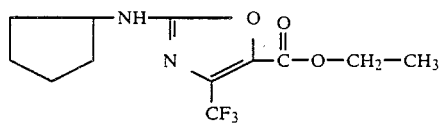

Ethyl 2-(cyclopentylamino)-4-(trifluoromethyl)-5-oxazolecarboxylate

By the procedure of Example 4, 7.68 g (60 mmol) of cyclopentyl urea was reacted with 10.9 g (50 mmol) of ethyl 2-chloro-4,4,4-trifluoroacetoacetate at 140°-150° C. for 18 hours. The product was separated and then recrystallized from methylcyclohexane to yield 5.0 g of a white solid product (m.p.=41°-42° C.) identified in Table I.

EXAMPLE 24

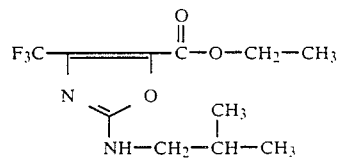

Ethyl 2-[(2-methylpropyl)amino]-4-(trifluoromethyl)-5-oxazolecarboxylate

By the procedure of Example 4, 7.0 g (60 mmol) of isobutyl urea was reacted with 10.9 g (50 mmol) of ethyl 2-chloro-4,4,4-trifluoroacetoacetate at 140°-150° C. for 18 hours. The product was separated and then recrystallized from methylcyclohexane to yield 4.72 g of a yellow powder product (m.p.=43°-44° C.) identified in Table I.

EXAMPLE 25

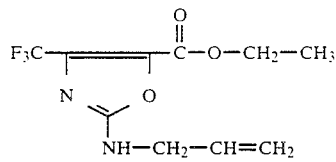

Ethyl 2-(2-propenylamino)-4-(trifluoromethyl)-5-oxazolecarboxylate

By the procedure of Example 4, 6 g (60 mmol) of allyl urea was reacted with 10.9 g (50 mmol) of ethyl 2-chloro-4,4,4-trifluoroacetoacetate at 140°-150° C. for 18 hours. The product was separated and then recrystallized from methylcyclohexane to yield 4.77 g of a yellow solid product (m.p.=48°-49° C.) identified in Table I.

EXAMPLE 26

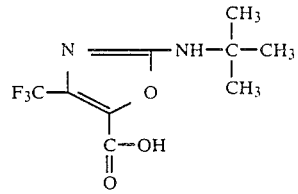

2-[(1,1-Dimethylethyl)amino]-4-(trifluoromethyl)-5-oxazolecarboxylic acid

A reaction vessel was charged with 200 ml tetrahydrofuran and 28 g (100 mmol) of ethyl 2-[(1,1dimethylethyl)amino]-4-trifluoromethyl-5-oxazolecarboxylate (prepared by Example 6). With this mixture stirred at ambient temperature, 50% aqueous sodium hydroxide (16 g; 200 mmol) was added followed by 50 ml water as a rinse. The reaction mixture was stirred at ambient temperature for 16 hours. The mixture was then poured into 500 ml of 5% hydrochloric acid. After cooling with an ice bath, the mixture was filtered, washed with water, and then dried to yield 2.4 g of a white powder

EXAMPLE 27

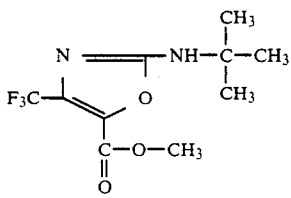

Methyl
2-[(1,1-dimethylethyl)amino-4-(trifluoromethyl)-5-oxazolecarboxylate

To a stirred suspension of 2.5 g (10 mmol) of 2-(tert-butylamino)-4-trifluoromethyl-5-oxazolecarboxylic acid in 10 ml thionyl chloride, there was added 5 drops dimethylformamide. This suspension was heated at reflux for one hour, and the resulting homogeneous orange-colored mixture was concentrated under reduced pressure to yield an orange oil. This oil was dissolved in methylene chloride and concentrated under reduced pressure three times successively to yield 2.8 g of an orange oil identified as crude acid chloride. This oil was stirred with 15 ml of methanol at ambient temperature for 15 minutes and then the methanol was removed under reduced pressure with a rotary evaporator. The remaining yellow oil (2.4 g) was purified by HPLC separation using methylene chloride and silica gel to yield 1.75 g of a pale yellow oil which was crystallized from hexane at $-76°$ C. to yield 1.6 g of a white crystalline solid (m.p.=57°-59° C.) identified in Table I.

EXAMPLE 28

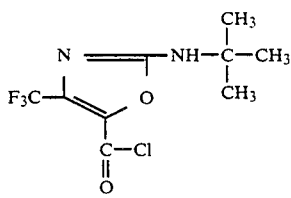

2-[(1,1-dimethylethyl)amino]-4-(trifluoromethyl)-5-oxazolecarbonyl chloride

By the procedure of Example 27, 17 g (64.5 mmol) of 2-(tert-butylamino)-4-trifluoromethyl-5-oxazolecarboxylic acid, 67 ml thionyl chloride and 4 of drops dimethylformamide were reacted together. The product was separated and then distilled to yield 17.2 g of a yellow solid product (m.p.=52°-60° C.; b.p. 70° C. @ 0.25 mm Hg) identified in Table I.

EXAMPLE 29

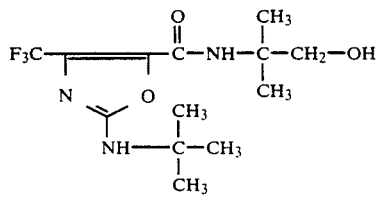

2-[(1,1-dimethylethyl)amino]-N-(2-hydroxy-1,1-dimethylethyl)-4-(trifluoromethyl)-5-oxazolecarboxamide A reaction vessel fitted with a calcium sulfate drying tube was charged with 4.9 g (55 mmol) of 2-amino-2-methyl-1-propanol and 50 ml of anhydrous ethyl ether. With this mixture stirred at 0°-5° C., there was added dropwise over a period of 45 minutes a solution of 50 ml anhydrous ethyl ether containing 6.5 g (25 mmol) of 2-(tert-butylamino)-4-trifluoromethyl-5-oxazolecarbonyl chloride. The reaction mixture was stirred at ambient temperature for 1½ hours, then filtered to remove the HCl salt of 2-amino-2-methyl1-propanol. The ether filtrate was washed successively with one molar oxalic acid and saturated brine, then dried under magnesium sulfate, and concentrated under reduced pressure to yield 8.2 g of a colorless, viscous oil. This oil was mixed with hexane and heated to reflux to yield a white solid material. The material was cooled and filtered to yield 7.7 g of a white crystalline product (m.p.=140°-144° C.) identified in Table I.

EXAMPLE 30

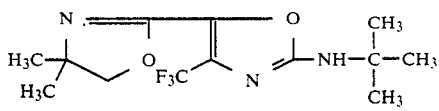

N-(1,1-dimethylethyl)-4,5-dihydro-4,4-dimethyl-4'-(trifluoromethyl)-2,5'-bioxazol-2'-amine Over a period of 10 minutes, 3.8 g (32 mmol) of thionyl chloride was added dropwise to 3.23 g (10 mmol) of stirred solid N'-(2',2'-dimethyl-3'-hydroxypropyl)-2-(tert-butylamino)-4-trfluoromethyl-5-oxazolecarbamide. The reaction mixture was observed to warm and evolve gases. The resulting yellow homogeneous mixture was stirred at ambient temperature for one hour, then diluted with ether, and filtered to yield 3.1 g of a white solid material (m.p.=108°-111° C.; presumably the hydrochloride salt of the oxazoline). This solid material was added to a stirred mixture of 25 ml of 10% sodium hydroxide and 25 ml of crushed ice to form a white slurry which was then extracted with ethyl ether. The ether extract was washed with saturated brine, dried over potassium carbonate and concentrated under reduced pressure to yield a white solid material which was recrystallized from hexane at $-76°$ C. to yield 2.35 g of a white solid product (m.p.=88°-90° C.) identified in Table 1.

EXAMPLE 31

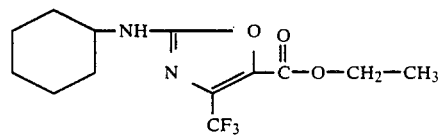

Ethyl
2-(cyclohexylamino)-4-(trifluoromethyl)-5-oxazolecarboxylate

By the procedure of Example 4, 8.52 g (60 mmol) of cyclohexyl urea was reacted with 10.9 g (50 mmol) of ethyl 2-chloro-4,4,4-trifluoroacetoacetate at 140°-150°

C. for 72 hours. The product was separated and then recrystallized several times from methylcyclohexane to yield 5.92 g of a fine white powder product (m.p.=73°-74° C.) identified in Table I.

EXAMPLE 32

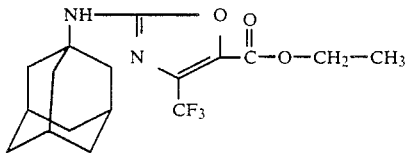

Ethyl 2-(1-adamantanylamino)-4-(trifluoromethyl)-5-oxazolecarboxylate

By the procedure of Example 4, 11.6 g (60 mmol) of adamantyl urea was reacted with 10.9 g (50 mmol) of ethyl 2-chloro-4,4,4-trifluoroacetoacetate at 140°-150° C. for 24 hours. The product was separated and then recrystallized from methylcyclohexane to yield 7.0 g of a white solid product (m.p.=109°-111° C.) identified in Table I.

EXAMPLE 33

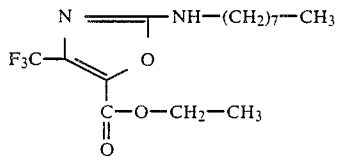

Ethyl 2-(octylamino)-4-(trifluoromethyl)-5-oxazolecarboxylate

By the procedure of Example 4, 5.16 g (30 mmol) of n-octyl urea was reacted with 5.4 g (25 mmol) of ethyl 2-chloro-4,4,4-trifluoroacetoacetate at 140°-150° C. for 18 hours. The product was separated and then recrystallized from petroleum ether to yield 1.5 g of a white powder product (m.p.=36°-37° C.) identified in Table I.

EXAMPLE 34

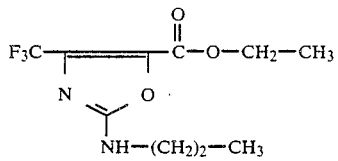

Ethyl 2-(propylamino)-4-(trifluoromethyl)-5-oxazolecarboxylate

By the procedure of Example 4, 6.13 g (60 mmol) of n-propyl urea was reacted with 10.9 g (50 mmol) of ethyl 2-chloro-4,4,4-trifluoroacetoacetate at 140°-150° C. for 18 hours. The product was separated and then recrystallized from n-heptane to yield 2.3 g of a yellow powder product (m.p.=33°-34° C.) identified in Table I.

EXAMPLE 35

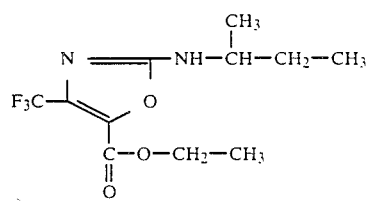

Ethyl 2-[(1-methylpropyl)amino]-4-(trifluoromethyl)-5-oxazolecarboxylate

By the procedure of Example 4, 6.96 g (60 mmol) of sec-butyl urea was reacted with 10.9 g (50 mmol) of ethyl 2-chloro-4,4,4-trifluoroacetoacetate at 140°-150° C. for 3 hours. The product was separated and then Kugelrohr distilled to yield 4.0 g of a colorless oil product (b.p.=100° C. @ 0.25 mm Hg) identified in Table I.

EXAMPLE 36

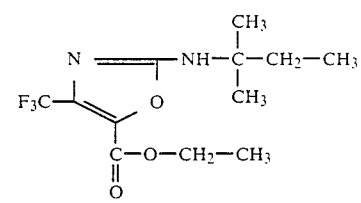

Ethyl 2-[(1,1-dimethylpropyl)amino]-4-(trifluoromethyl)-5-oxaxolecarboxylate

By the procedure of Example 4, 7.8 g (60 mmol) of tert-pentyl urea was reacted with 10.9 g (50 mmol) of ethyl 2-chloro-4,4,4-trifluoroacetoacetate at 140°-150° C. for 66 hours. The product was separated and then Kugelrohr distilled to yield 4.82 g of a yellow oil product (b.p.=120° C. @ 0.25 mm Hg) identified in Table I.

EXAMPLE 37

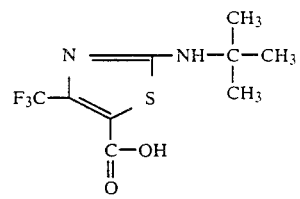

2-[(1,1-dimethyl)amino]-4-(trifluoromethyl)-5-thiazolecarboxylic acid

A reaction vessel was charged with 35 ml of tetrahydrofuran and 5 g (17 mmol) of ethyl 2-[(1,1-dimethylethyl)amino]-4-trifluoromethyl-5-thiazolecarboxylate (prepared by Example 22). With this mixture stirred at ambient temperature, 50% aqueous sodium hydroxide (1.35 g; 34 mmol) was added followed by 8 ml of water as a rinse. The yellow reaction mixture was stirred at ambient temperature for 64 hours. The mixture was then poured into 100 ml of 5% hydrochloric acid, filtered, washed with large amounts of water, and dried to yield 3.4 g of a light yellow solid product (m.p.=223°-224° C.) identified in Table I.

EXAMPLE 38

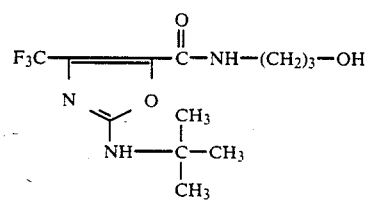

2-[(1,1-dimethylethyl)amino]-N-(3-hydroxypropyl)4-(trifluoromethyl)-5-oxazolecarboxamide A reaction vessel fitted with a calcium sulfate drying tube was charged with 10 ml of methylene chloride, 0.9 g (12 mmol) of 3-amino-1-propanol, and 1.34 g (13.2 mmol) oftriethylamine. With this mixture stirred at 0° C., there was added dropwise over a 15-minute period a solution of 25 ml of methylene chloride containing 3.25 g (20 mmol) of 2-(tert-butylamine)-4-trifluoromethyl-5-oxazolecarbonyl chloride. The reaction mixture was stirred at ambient temperature for 1½ hours. The resulting yellow mixture was washed with large amounts of water, dried over magnesium sulfate, and concentrated under reduced pressure to yield 3.26 g of a light yellow solid material which was recrystallized in toluene to yield 1.2 g of a yellow solid material which contained significant amounts of toluene. This solid material was maintained under reduced pressure overnight and then subjected to Kugelrohr distillation (105°-110° C. @ 5 mm) to yield 0.8 g of a yellow solid product (m.p.=106°-108° C.) identified in Table I.

EXAMPLE 39

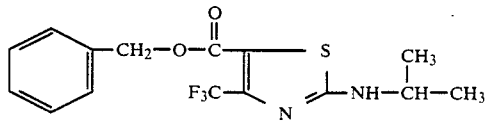

Benzyl 2-[(1-methylethyl)amino]-4-(trifluoromethyl)-5-thiazolecarboxylate

A reaction vessel was charged with 25 ml of acetonitrile, 2.94 g (49.8 mmol) of iso-propylamine, and 8 g (24.9 mmol) of benzyl 2-chloro-4-trifluoromethyl-5-thiazolecarboxylate (prepared as described in U.S. Pat. No. 4,199,506). The reaction mixture was heated at reflux for 16 hours. The mixture was then cooled to ambient temperature, diluted with ethyl ether, washed with large amounts of water, dried over magnesium sulfate, and concentrated under reduced pressure to yield 5.32 g of a gold oil. This oil was subjected ! to Kugelrohr distillation (145°-155° C. @ 0.5 mm Hg) to yield 4.97 of a gold oil which was then triturated in hexane to yield 3.99 g of a yellow solid product (m.p.=49°-53° C.) identified in Table I.

EXAMPLE 40

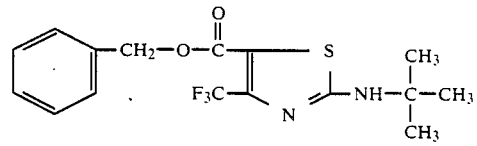

Benzyl 2[(1,1-dimethylethyl)amino]-4-(trifluoromethyl)-5-thiazolecarboxylate

By the procedure of Example 39, a stirred mixture of 15 ml of acetonitrile, 2.72 g (38 mmol) of tert-butylamine, and 6 g (19 mmol) of benzyl 2-chloro-4-trifluoromethyl-5-thiazolecarboxylate (prepared as described in U.S. Pat. No. 4,199,506), was heated at reflux for 66 hours. The product was separated and then recrystallized from hexane to yield 2.90 g of an off-white powder product (m.p.=79°-81° C.) identified in Table I.

EXAMPLE 41

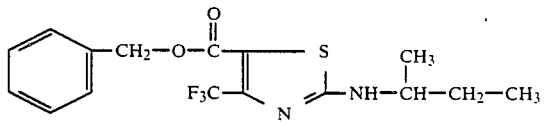

Benzyl 2-[(1-methylpropyl)amino]-4-(trifluoromethyl)-5-thiazolecarboxylate

By the procedure of Example 39, a stirred mixture of 20 ml acetonitrile, 3.65 g (49.8 mmol) of sec-butylamine, and 8 g (24.9 mmol) of benzyl 2-chloro-4-trifluoromethyl-5-thiazolecarboxylate (prepared as described in U.S. Pat. No. 4,199,506), was heated at reflux for 16 hours. The product was separated and then triturated in hexane to yield 2.70 g of an off-white solid product (m.p.=56°-57° C.) identified in Table I.

EXAMPLE 42

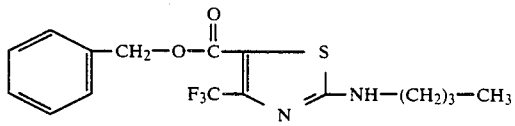

Benzyl 2-(butylamino)-4-(trifluoromethyl)-5-thiazolecarboxylate

By the procedure of Example 39, a stirred mixture of 20 ml acetonitrile, 3.65 g (49.8 mmol) of n-butylamine, and 8 g (24.9 mmol) of benzyl 2-chloro-4-trifluoromethyl-5-thiazolecarboxylate (prepared as described in U.S. Pat. No. 4,199,506), was heated at reflux for 24 hours. The product was separated and then recrystallized from hexane to yield 3.24 g of a yellow solid product (m.p.=77°-79° C.) identified in Table I.

EXAMPLE 43

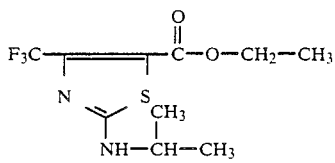

Ethyl 2-[(1-methylethyl)amino]-4-(trifluoromethyl)-5-thiazolecarboxylate

By the procedure of Example 39, a stirred mixture of 10 ml acetonitrile, 2.28 g (38.6 mmol) of iso-propylamine, and 5 g (19.3 mmol) of ethyl 2-chloro-4-trifluoromethyl-5-thiazolecarboxylate (prepared as described in U.S. Pat. No. 4,199,506), was heated at reflux for 16 hours. The product was separated and then recrystallized in hexane to yield 2.30 g of a beige solid product (m.p.=94°–97° C.) identified in Table 1.

EXAMPLE 44

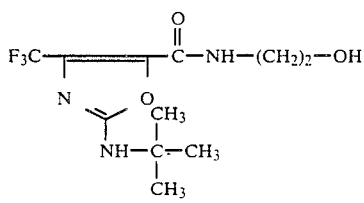

2-[(1,1-dimethylethyl)amino]-N-(2-hydroxyethyl)-4-(trifluoromethyl)-5-oxazolecarboxamide By the procedure of Example 38, a stirred mixture of 50 ml methylene chloride, 0.70 g (11.46 mmol) of ethanolamine, 1.27 g (12.61 mmol) of triethylamine, and 3.1 g (11.46 mmol) of 2-(tert-butylamino)-4-trifluoromethyl-5-oxazolecarbonyl chloride, was reacted for 64 hours at ambient temperature. The product was separated and then recrystallized to yield 1.16 g of a yellow solid product (m.p.=154°–156° C.) identified in Table 1.

EXAMPLE 45

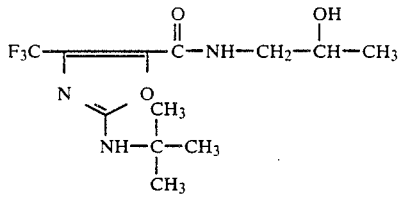

2-[(1,1-dimethylethyl)amino]-N-(2-hydroxypropyl)-4-(trifluoromethyl)-5-oxazolecarboxamide By the procedure of Example 38, a stirred mixture of 70 ml methylene chloride, 1.80 g (24 mmol) of 1-amino-2-propanol, 2.68 g (13.2 mmol) of triethylamine, and 6.50 g (24 mmol) of 2-(tert-butylamino)-4-trifluoromethyl-5-oxazolecarbonyl chloride was reacted for 16 hours at ambient temperature. The product was separated and then recrystallized to yield 3.42 g of a white solid product (m.p.=105°–107° C.) identified in Table I.

EXAMPLE 46

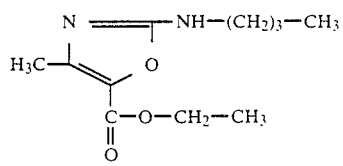

Ethyl 2-(butylamine)-4-methyl-5-oxazolecarboxylate

By the procedure of Example 4, 27.9 g (240 mmol) of n-butyl urea was reacted with 32.8 g (200 mmol) of ethyl 2-chloro-acetoacetate at 140°–150° C. for 16 hours. The product was separated and then purified by Kugelrohr distillation and column chromatography on silica gel with methylene chloride to yield 4.02 g of a light yellow oil product (b.p.=140° C. @ 0.25 mm Hg) identified in Table I.

EXAMPLE 47

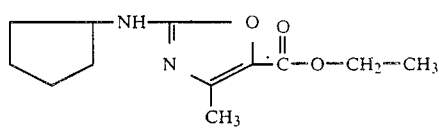

Ethyl 2-(cyclopentylamino)-4-methyl-5-oxazolecarboxylate

By the procedure of Example 4, 10 g (78 mmol) of cyclopentyl urea was reacted with 10.7 g (65 mmol) of ethyl 2-chloroacetoacetate at 140°–150° C. for 4 hours. The product was separated, then purified by Kugelrohr distillation (135° C. @ 0.5 mm Hg) and then recrystallized from hexane to yield 2.54 g of a light yellow solid product (m.p.=50°–52° C.) identified in Table I.

EXAMPLE 48

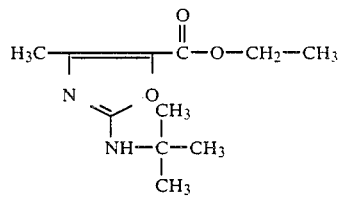

Ethyl 2-[(1,1-dimethylethyl)amino]-4-methyl-5-oxaxolecarboxylate

By the procedures of Example 4, 69.6 g (600 mmol) of tert-butyl urea was reacted with 82.3 g (500 mmol) of ethyl 2-chloro-acetoacetate in 125 ml of dimethylformamide at 140°–150° C. for 36 hours. The product was separated, then triturated in acetonitrile, and then recrystallized from hexane to yield 12.0 g of a beige solid product (m.p.=107°–108° C.) identified in Table I.

EXAMPLE 49

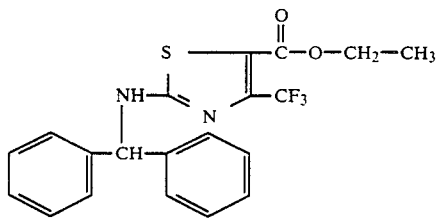

Ethyl 2[(diphenylmethyl)amino]-4-(trifluoromethyl)-5thiazolecarboxylate

A reaction vessel was charged with 120 ml of toluene and 11.0 g (42.4 mmol) of ethyl 2-chloro-4-trifluoromethyl-5-thiazolecarboxylate (prepared as described in U.S. Pat. No. 4,199,506). Then, 15.5 g (86 mmol) of aminodiphenylmethane was added in one portion. The resulting yellowish-orange solution was refluxed under nitrogen for 9 days. Then, solvent was removed from the mixture under reduced pressure to yield a yellowish-orange solid material, which was flash chromatographed (~38 ml/min) on silica gel using 10% ethyl acetate in hexane solvent. There was obtained 13.2 g of a thick yellow oil which solidified upon standing to a yellow solid product (m.p.=92°–95° C.) identified in Table I.

EXAMPLE 50

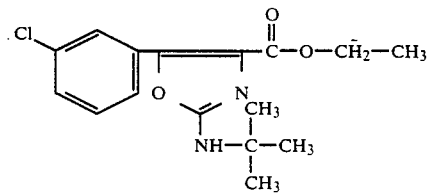

Ethyl 2-[(1,1-dimethylethyl)amino]-5-(3-chlorophenyl)-4-oxazolecarboxylate

A reaction vessel was charged with 6.5 g (25 mmol) of ethyl 3-chloro-3-(m-chlorophenyl)pyruvate and 2.9 g (25 mmol) of tert-butyl urea. The reaction mixture was heated at 105°–115° C. for 2 hours. The mixture was cooled to ambient temperature and 1.71 g of tert-butyl urea starting material was removed by crystallization in hexane-ethyl acetate solution. The remaining 10.16 g of a brown oil was subjected to Kugelrohr distillation (70°–80° C. @ 0.3 mm Hg) to yield 5.08 g of a gold viscous oil. This oil was chromatographed on silica gel using a Waters Prep 500 system and 10% ethyl acetate-in-hexane eluent to yield product identified in Table 1.

EXAMPLE 51

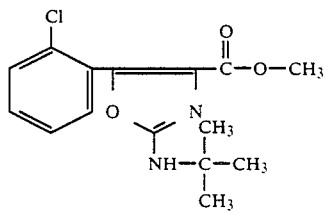

Methyl 2-[(1,1-dimethylethyl)amino]5-(2-chlorophenyl)-4-oxazolecarboxylate

By the procedure of Example 50, 12.35 g (50 mmol) of methyl 3-chloro-3-(o-chlorophenyl)pyruvate was reacted with 5.8 g (50 mmol) of tert-butyl urea at 105°–115° C. for 8 hours. The reaction mixture was cooled to ambient temperature and then diluted with methylene chloride, washed with water, dried over magnesium sulfate, and concentrated under reduced pressure to yield a yellow oil. This oil was purified by flash chromatography techniques on silic gel using 10% ethyl acetate in hexane as eluent. There was obtained 5.77 g of an orange viscous oil product identified in Table I.

EXAMPLE 52

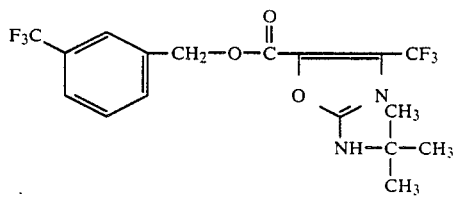

3-Trifluoromethylbenzyl 2-[(1,1-dimethylethyl)amino]-4-(trifluoromethyl)-5-oxazolecarboxylate A reaction vessel was charged with 50 ml of dimethylformamide, 2.6 g (18.8 mmol) of potassium carbonate, and 5.36 g (28 mmol) of m-trifluoromethyl benzyl chloride. With this mixture stirred at ambient temperature under a nitrogen atmosphere, there was added 4.03 g (17 mmol) of 2-[(1,1-dimethylethyl)amino]-4-trifluoromethyl-5-oxazolecarboxylic acid (prepared by Example 26). The reaction mixture was stirred at ambient temperature for 36 hours. Then, the mixture was added to water and extracted four times with ethyl ether. The ether extracts were washed with large amounts of water, then dried over magnesium sulfate, and concentrated under reduced pressure to yield 11.25 g of a yellow oily solid material. This solid material was dissolved in ethyl ether, washed with large amounts of water, dried over magnesium sulfate, and concentrated under reduced pressure to yield 10.8 g of a gold viscous oil. Then, 5.0 g of this oil was subjected to Kugelrohr distillation (83°–85° C. @ 0.5 mm Hg) to yield 1.38 g of a gold viscous oil which upon standing overnight formed an oily solid product identified in Table I.

EXAMPLE 53

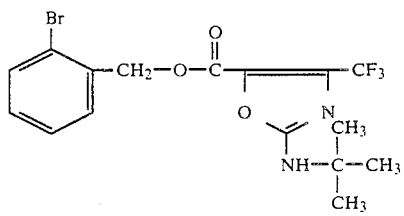

2-Bromobenzyl 2-[(1,1-dimethylethyl)amino]-4-(trifluoromethyl)-5-oxazolecarboxylate A reaction vessel was charged with 100 ml of dimethylformamide, 6.11 g (50 mmol) of potassium carbonate, and 18 g (72 mmol) of o-bromobenzyl bromide. With this mixture stirred at ambient temperature under a nitrogen atmosphere, there was added 10 g (40 mmol) of 2-[(1,1-dimethylethyl)amino]-4-trifluoromethyl-5-oxazolecarboxylic acid (prepared by Example 26). The reaction mixture was stirred at ambient temperature for 18 hours. Then, the mixture was added to water and extracted three times with ethyl ether. The ether extracts were washed with large amounts of water, then dried over magnesium sulfate, and concentrated under reduced pressure to yield 24.5 g of a gold oil. This oil was subjected to Kugelrohr distillation (65°–70° C. @ 0.4 mm Hg) to yield 9.7 g of a gold oil. The remaining still residue upon standing at ambient temperature for 30 minutes formed a solid material. Trituration of this solid material in hexane at ambient temperature resulted in 11.48 g of a white solid product (m.p.=74°–77° C.) identified in Table I.

EXAMPLE 54

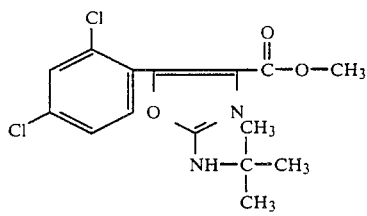

Methyl 2-[(1,1-dimethylethyl)amino]-5-(2,4-dichlorophenyl)-4-oxazolecarboxylate

By the procedure of Example 50, 2.5 g (8.9 mmol) of ethyl 2-chloro-2-(2,4-dichlorophenyl)pyruvate was reacted with 1.13 g (9.8 mol) of tertbutyl urea at about 110° C. for 12 hours. The brown residual solid material was then extracted several times with hot hexane. The hexane extracts were cooled and combined to yield 2.1 g of a white solid product (m.p.=132°–134° C.) identified in Table 1.

EXAMPLE 55

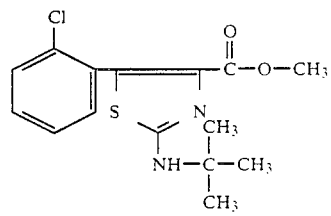

Methyl 2-[(1,1-dimethylethyl)amino]-5-(2-chlorophenyl)-4-thiazolecarboxylate

A reaction vessel was charged with 50 ml methanol and 4 g (30 mmol) of tert-butyl thiourea. With this mixture stirred and cooled in an ice bath, there was added over a 5-minute period 7.41 g of (30 mmol) methyl 3-chloro-3-(o-chlorophenyl)pyruvate. The reaction mixture was refluxed for 16 hours. The mixture was cooled to ambient temperature and concentrated under reduced pressure to yield 9.18 g of a yellow solid which became a hard, glass-like material. This material was recrystallized from an acetone-water solution to yield 7.0 g of a yellow solid product (m.p.=159°–161° C.) identified in Table I.

EXAMPLE 56

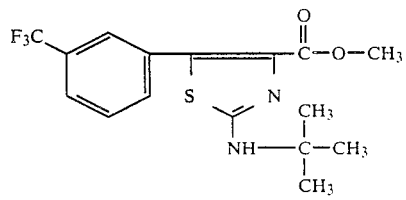

Methyl 2-[(1,1-dimethylethyl)amino]-5-[3-(trifluoromethyl)phenyl-4-thiazolecarboxylate By the procedure of Example 55, 2.4 g (18 mmol) of tert-butyl thiourea was reacted with 5.0 g (18 mmol) of methyl 3-chloro-3-(m-trifluoromethylphenyl)pyruvate in 50 ml of methanol at reflux for 16 hours. The product was separated, then triturated in hexane, and then recrystallized from an acetone-water mixture to yield 3.6 g of a yellow solid product (m.p.=78°–82° C.) identified in Table 1.

EXAMPLE 57

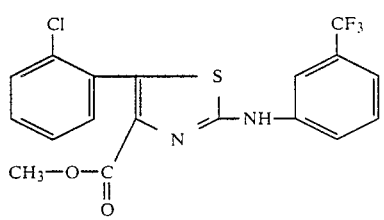

Methyl 2-{[3-(trifluoromethyl)phenyl]amino-5-(2-chlorophenyl)-4-thiazolecarboxylate By the procedure of Example 55, 5.0 g (23 mmol) of 3-trifluoromethylphenyl-2-thiourea was reacted with 5.68 g (23 mmol) of methyl 2-chloro-2-(o-chlorophenyl)pyruvate in 150 ml of methanol at reflux for 16 hours. The product was separated and then triturated in warm ethanel to yield 7.2 g of a white solid product (m.p.=209°-211° C.) identified in Table I.

EXAMPLE 58

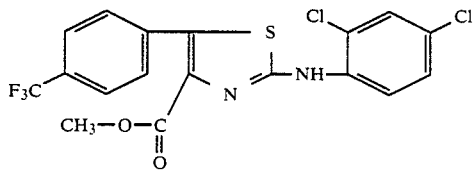

Methyl 2-[(2,4-dichlorophenyl)amino]-5-[3-(trifluoromethyl)phenyl]-4-thiazolecarboxylate By the procedure of Example 55, 5.14 g (23 mmol) of 2,4-dichlorophenyl-2-thiourea was reacted with 6.44 g (23 mmol) of methyl 3-chloro-3-(p-trifluoromethylphenyl)pyruvate in 150 ml of methanol at reflux for 72 hours. The product was separated and then recrystallized from an ethanol-water mixture to yield 7.07 g of a yellow solid product (m.p.=148°-150° C.) identified in Table 1.

EXAMPLE 59

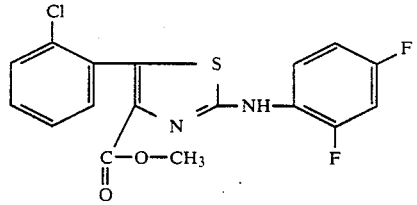

Methyl 2-[(2,4-difluorophenyl)amino]-5-(2-chlorophenyl)-4-thiazolecarboxylate

A reaction vessel was charged with 75 ml of toluene, 3.58 g (27.8 mmol) of 2,4-difluoroaniline and 4.0 g (13.9 mmol) of methyl 2-chloro-4-(o-chlorophenyl)-5-thiazolecarboxylate. The reaction mixture was refluxed for 16 hours and then cooled. The mixture was concentrated under reduced pressure to yield 2.91 g of a very dark gold oil. This oil was decolorized with carbon black, then chromatographed on silica gel with a 25% ethyl acetate-in-hexane eluent to yield 2.3 g of a gold oil product identified in Table I.

EXAMPLE 60

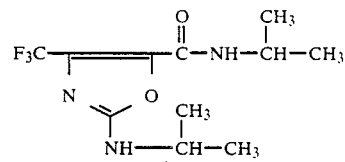

N-(1-methylethyl)-2-[(1-methylethyl)]amino]-4-(trifluoromethyl)-5-oxazolecarboxamide A reaction vessel was charged with 4.87 g (20 mmol) of ethyl 2-chloro-4-trifluoromethyl-5-oxazolecarboxylate (prepared as described in U.S. Pat. No. 4,303,439). Then, with the vessel contents at ambient temperature, 30 ml of isopropylamine was added and a slight exothermic reaction was observed. The reaction mixture was stirred at ambient temperature for 72 hours and then concentrated under reduced pressure to yield 10.6 g of a gold viscous oil which was recrystallized from an ethanol-water solution to yield 5.5 g of a gold solid product (m.p.=176°-179° C.) identified in Table I.

TABLE I

| | | Antidote Compound Analytical Results | | | | | | |
|---|---|---|---|---|---|---|---|---|
| Example Compound No. | Empirical Formula | Molecular Weight | % C Theory | % C Found | % H Theory | % H Found | % N*/% F**/% S*** Theory | % N*/% F**/% S*** Found |
| 1 | $C_9H_{11}F_3N_2O_2S$ | 268.28 | 40.30 | 40.36 | 4.13 | 4.15 | 10.44 | 10.55* |
| 2 | $C_{11}H_{15}F_3N_2O_2S$ | 296.32 | 44.59 | 44.61 | 5.10 | 5.13 | 9.45 | 9.44* |
| 3 | $C_{18}H_{13}F_3N_2O_2S$ | 378.38 | 57.14 | 57.01 | 3.46 | 3.37 | 7.40 | 7.39* |
| | | | | | | | 8.48 | 8.55*** |
| | | | | | | | 15.06 | 14.91** |
| 4 | $C_{21}H_{19}F_3N_2O_3$ | 404.39 | 62.37 | 62.59 | 4.74 | 4.83 | 6.93 | 6.82* |
| 5 | $C_{21}H_{22}N_2O_3$ | 350.42 | 71.98 | 71.84 | 6.33 | 6.27 | 7.99 | 8.13* |
| 6 | $C_{11}H_{15}F_3N_2O_3$ | 280.25 | 47.14 | 47.33 | 5.40 | 5.51 | 10.00 | 9.91* |
| 7 | $C_{12}H_{17}F_3N_2O_2$ | 294.28 | 48.98 | 48.99 | 5.82 | 5.76 | 9.52 | 9.61* |
| 8 | $C_8H_9F_3N_2O_3$ | 238.17 | 40.34 | 40.41 | 3.81 | 3.75 | 11.76 | 11.89* |
| 9 | $C_{11}H_{15}F_3N_2O_3$ | 280.25 | 47.14 | 46.87 | 5.40 | 5.31 | 10.00 | 9.72* |
| 10 | $C_7H_7F_3N_2O_3$ | 224.14 | 37.51 | 37.44 | 3.15 | 3.13 | 12.50 | 12.47* |
| 11 | $C_9H_{11}F_3N_2O_3$ | 252.20 | 42.86 | 42.80 | 4.40 | 4.33 | 11.11 | 11.27* |
| | | | | | | | 22.60 | 22.31** |
| 12 | $C_{14}H_{10}F_6N_2O_3$ | 368.25 | 45.66 | 45.61 | 2.74 | 2.66 | 7.61 | 7.64* |
| 13 | $C_{10}H_{13}F_3N_2O_3$ | 266.23 | 45.12 | 43.02 | 4.92 | 4.68 | 10.52 | 10.27* |
| | | | | | | | 21.41 | 20.70** |
| 14 | $C_{13}H_{11}F_3N_2O_3$ | 300.24 | 52.01 | 52.85 | 3.69 | 3.65 | 9.33 | 9.65* |
| | | | | | | | 18.98 | 18.02** |
| 15 | $C_{14}H_{13}F_3N_2O_4$ | 330.27 | 50.91 | 50.73 | 3.97 | 3.85 | 8.48 | 8.67* |

TABLE I-continued

Antidote Compound Analytical Results

| Example Compound No. | Empirical Formula | Molecular Weight | % C Theory | % C Found | % H Theory | % H Found | % N*/% F**/% S*** Theory | Found |
|---|---|---|---|---|---|---|---|---|
| 16 | $C_{14}H_{13}F_3N_2O_3$ | 314.27 | 53.51 | 53.48 | 4.17 | 4.08 | 8.91 | 9.02* |
| 17 | $C_{16}H_{17}F_3N_2O_3$ | 342.32 | 56.14 | 56.19 | 5.01 | 4.96 | 8.18 | 8.20* |
| 18 | $C_{15}H_{15}F_3N_2O_3$ | 328.30 | 54.88 | 53.89 | 4.61 | 4.46 | 8.53 | 8.51* |
| 19 | $C_{13}H_{10}ClF_3N_2O_3$ | 334.69 | 46.65 | 46.53 | 3.01 | 2.87 | 8.37 | 8.35* |
| 20 | $C_{11}H_{13}F_3N_2O_5$ | 310.23 | 42.59 | 42.69 | 4.22 | 4.14 | 9.03 | 9.03* |
| 21 | $C_9H_{11}F_3N_2O_3$ | 252.20 | 42.86 | 42.75 | 4.40 | 4.31 | 11.11 | 10.73* |
| 22 | $C_{11}H_{15}F_3N_2O_2S$ | 296.32 | 44.59 | 44.69 | 5.10 | 5.15 | 9.45 | 9.47* |
|  |  |  |  |  |  |  | 10.82 | 10.95*** |
| 23 | $C_{12}H_{15}F_3N_2O_3$ | 296.26 | 49.32 | 49.44 | 5.17 | 5.63 | 9.59 | 9.45* |
| 24 | $C_{11}H_{15}F_3N_2O_3$ | 280.25 | 47.14 | 47.03 | 5.40 | 5.44 | 10.00 | 10.18* |
| 25 | $C_{10}H_{11}F_3N_2O_3$ | 264.21 | 45.46 | 44.80 | 4.20 | 4.08 | 10.60 | 10.63* |
| 26 | $C_9H_{11}F_3N_2O_3$ | 252.20 | 42.86 | 42.78 | 4.40 | 4.34 | 11.11 | 11.08* |
| 27 | $C_{10}H_{13}F_3N_2O_3$ | 266.23 | 45.12 | 45.14 | 4.92 | 4.90 | 10.52 | 10.53* |
| 28 | $C_9H_{10}ClF_3N_2O_2$ | 323.32 | 39.94 |  | 3.72 |  | 10.35 | * |
| 29 | $C_{13}H_2F_3N_3O_3$ | 323.32 | 48.29 | 48.73 | 6.24 | 6.30 | 13.00 | 13.12* |
| 30 | $C_{13}H_{18}F_3N_3O_2$ | 305.31 | 51.14 | 51.07 | 5.94 | 5.97 | 13.76 | 13.76* |
| 31 | $C_{13}H_{17}F_3N_2O_3$ | 306.29 | 50.98 | 51.86 | 5.59 | 5.99 | 9.15 | 9.07* |
| 32 | $C_{17}H_{21}F_3N_2O_3$ | 358.37 | 56.98 | 58.28 | 5.91 | 6.19 | 7.82 | 7.57* |
| 33 | $C_{15}H_{23}F_3H_3O_3$ | 336.36 | 53.56 | 54.12 | 6.89 | 7.02 | 8.33 | 8.33* |
| 34 | $C_{10}H_{13}F_3N_2O_3$ | 266.23 | 45.12 | 45.01 | 4.92 | 5.09 | 10.52 | 11.77* |
| 35 | $C_{11}H_{15}F_3N_2O_3$ | 280.25 | 47.14 | 46.58 | 5.40 | 5.50 | 10.00 | 10.52* |
| 36 | $C_{12}H_{17}F_3N_2O_3$ | 294.28 | 48.98 | 48.40 | 5.82 | 5.84 | 9.52 | 9.83* |
| 37 | $C_9H_{11}F_3N_2O_2S$ | 268.27 | 40.30 | 40.45 | 4.13 | 4.31 | 10.44 | 10.27* |
| 38 | $C_{12}H_{18}F_3N_3O_3$ | 309.29 | 46.60 | 46.74 | 5.87 | 5.89 | 13.59 | 13.45* |
|  |  |  |  |  |  |  | 18.43 | 18.51 (F) |
| 39 | $C_{15}H_{15}F_3N_2O_2S$ | 344.37 | 52.32 | 51.95 | 4.39 | 4.26 | 8.13 | 8.17* |
| 40 | $C_{16}H_{17}F_3N_2O_2S$ | 358.39 | 53.62 | 53.66 | 4.78 | 4.63 | 7.82 | 7.72* |
| 41 | $C_{16}H_{17}F_3N_2O_2S$ | 358.39 | 53.62 | 53.74 | 4.78 | 4.65 | 7.82 | 7.79* |
| 42 | $C_{16}H_{17}F_3N_2O_2S$ | 358.39 | 53.62 | 53.60 | 4.78 | 4.76 | 7.82 | 7.88* |
| 43 | $C_{10}H_{13}F_3N_2O_2S$ | 282.29 | 42.55 | 42.40 | 4.64 | 4.54 | 9.92 | 9.87* |
| 44 | $C_{11}H_{16}F_3N_3O_3$ | 294.27 | 44.75 | 45.12 | 5.46 | 5.31 | 14.23 | 13.93* |
| 45 | $C_{12}H_{18}F_3N_3O_3$ | 309.29 | 46.60 | 46.44 | 5.87 | 5.79 | 13.59 | 13.57* |
| 46 | $C_{11}H_{18}N_2O_3$ | 226.28 | 58.89 | 58.08 | 8.02 | 7.62 | 12.38 | 12.65* |
| 47 | $C_{12}H_{18}N_2O_3$ | 238.29 | 60.49 | 60.20 | 7.61 | 7.54 | 11.76 | 11.75* |
| 48 | $C_{11}H_{18}N_2O_3$ | 226.28 | 58.39 | 58.15 | 8.02 | 7.96 | 12.38 | 12.41* |
| 49 | $C_{20}H_{17}F_3N_2O_2S$ | 406.44 | 59.10 | 59.20 | 4.22 | 4.20 | 6.89 | 6.91* |
| 50 | $C_{16}H_{19}ClN_2O_3$ | 322.79 | 59.54 | 59.54 | 5.93 | 5.97 | 8.68 | 7.97* |
| 51 | $C_{15}H_{17}ClN_2O_3$ | 308.77 | 58.35 | 57.69 | 5.55 | 5.83 | 9.07 | 9.03* |
| 52 | $C_{17}H_{16}F_6N_3O_3$ | 410.33 | 49.76 | 49.19 | 3.93 | 3.89 | 6.83 | 6.74* |
| 53 | $C_{16}H_{16}BrF_3N_2O_3$ | 421.22 | 45.62 | 45.96 | 3.83 | 3.88 | 6.65 | 6.75* |
| 54 | $C_{15}H_{16}Cl_2N_2O_3$ | 343.21 | 52.49 | 52.10 | 4.70 | 4.67 | 8.16 | 8.19* |
| 55 | $C_{15}H_{17}ClN_2O_2S$ | 324.84 | 55.46 | 55.42 | 5.28 | 5.27 | 8.62 | 8.57* |
| 56 | $C_{16}H_{17}F_3N_2O_2S$ | 358.39 | 53.62 | 53.23 | 4.78 | 4.68 | 7.82 | 7.51* |
| 57 | $C_{18}H_{12}ClF_3N_2O_2S$ | 412.83 | 52.37 | 52.64 | 2.93 | 2.82 | 6.79 | 6.87* |
| 58 | $C_{18}H_{11}Cl_2F_3N_2O_2S$ | 447.27 | 48.34 | 48.35 | 2.48 | 2.39 | 6.26 | 6.26* |
| 59 | $C_{17}H_{11}ClF_2N_2O_2S$ | 380.81 | 53.62 | 50.36 | 2.91 | 3.35 | 7.36 | 7.23* |
| 60 | $C_{11}H_{16}F_3N_3O_2$ | 279.27 | 47.31 | 47.05 | 5.78 | 5.87 | 15.05 | 14.66* |

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil, with a mixture of herbicide and antidote, or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as "combination" is a commercially-convenient of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into or below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-50:1 (preferably 1:5-to 30:1) parts by weight may be employed. As indicated above, the antidote may be applied to the plant locus in a mixture, i.e., a mixture of a herbicidally-effective amount of herbicide and a safeningeffective amount of an antidote or sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 Kg/h. Preferably, antidote application rates range from about 0.5 Kg/ha down to about 0.05 Kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 61-64 in greenhouse testing. Measurements of biological response as reported in Tables II-V were made in the following manner. A visual comparison was made between a crop plant treated with herbicide alone and crop plant having no herbicide or antidote treatment an ("untreated control"). A number was assigned to this visual comparison indicating the percent injury or inhibition to the herbicide-alone treated crop plant (column "WO" in Tables II-V indicating herbicide "without" antidote). Also, a visual comparison was made between the crop plant treated with herbicide + antidote combination and the crop plant having no herbicide or antidote treatment (the untreated control). A number was assigned to this visual comparison indicating the percent injury or inhibition to the herbicide + antidote treated crop plant (column "W" in Tables II-V indicating herbicide "with" antidote). Where treatments involved weed plant species, observations of response to herbicide or herbicide + antidote were similarly recorded. The degree of reduction of herbicide injury provided by an antidote compound is indicated by the magnitude that the plant inhibition number of column "WO" exceeds the corresponding number of column "W". Also reported in Tables II-V are data showing "safening effect" for the herbicide + antidote combinations calculated from the plant inhibition numbers, the formula for calculation of which is shown below. Summarized below is key information for interpreting data reported in Tables II-V:

| Herbicide No. | Name |
|---|---|
| 1 | 2,3,3-trichloroallyldiisopropylthiocarbamate (triallate) |
| 2 | 2-chloro-4-ethylamine-6-isopropylamino-1,3,5-triazine (atrazine) |
| 3 | 2-chloro-2'-tert-butyl-6'-methyl-N-(methoxymethyl)acetanilide |
| 4 | 2-chloro-2',6'-diethyl-N-(methoxymethyl)-acetanilide (alachlor) |
| 5 | 2-chloro-N-(isobutoxymethyl)-2'6-acetoxylidide |
| 6 | 2-chloro-2'6'-diethyl-N-(butoxymethyl)-acetanilide (butachlor) |
| 7 | 2-chloro-N-(ethoxymethyl)-6'-ethyl-o-acetotoluidide (acetochlor) |
| 8 | 2-chloro-N-(2,6-dimethyl-1-cyclohexen-1-yl)-N-(2-ethoxyethyl)acetamide |
| 9 | 2-chloro-N-(2-methoxy-1-methylethyl)-6'-ethyl-o-acetotoluidide (metolachlor) |
| 10 | 2-chloro-2'-methyl-6'-methoxy-N-(isopropoxymethyl)acetanilide |
| 11 | 2-chloro-N-(2,6-dimethylphenyl)-N-(2-methoxyethyl)acetamde; TERIDOX dimethachlor; Ciba-Geigy CGA 17020 |
| 12 | 2-chloro-2'-methyl-6'-trifluoromethyl-N-(ethoxymethyl)acetanilide |
| 14 | 2-chloro-2'-(3-methyl)butoxy-6'-methyl-N-(methyl)acetanilide |
| 15 | 2-chloro-2'-methyl-6'-propoxy-N-(methyl)-acetanilide |
| 17 | 2-chloro-N-(ethoxymethyl)-N-[2-methyl-1-(1-methylethyl)-1-propenyl]acetanilide |
| 18 | 2-chloro-2'-ethyl-6'-(2-methylpropoxy)-N-(ethoxymethyl)acetanilide |
| 19 | 2-chloro-2'-methyl-6'-(1-methylbutoxy)-N-(methyl)acetanilide |
| 20 | 2-chloro-2'-ethyl-6'-(1-methylpropyl)-N-(methyl)acetanilide |
| 21 | 2-chloro-2'-(1,3-dimethylbutoxy)-6'-methyl- |

-continued

| Herbicide No. | Name |
|---|---|
| | N-(methyl)acetanilide |
| 22 | 2-chloro-2'-methyl-6'-(1-methylpropyl)-N-(methyl)acetanilide |

Antidote No. = Compound in corresponding Example No.
Rate = Kilograms/hectare (Kg/ha).
W = % Plant Inhibition caused by combination of herbicide and antidote.
WO = % Plant Inhibition caused by herbicide alone.
Data reported in parentheses = % Safening Effect
$$(\_) = \frac{WO - W}{WO} \times 100$$

EXAMPLE 61

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table II.

TABLE II

| | | | | % PLANT INHIBITION AND % SAFENING EFFECT ( ) | | | | | | | |
|---|---|---|---|---|---|---|---|---|---|---|---|
| HERBICIDE | | ANTIDOTE | | RICE | | SORGHUM | | WHEAT | | SOYBEAN | | CORN | |
| No. | RATE | No. | RATE | W | WO | W | WO | W | WO | W | WO | W | WO |
| 1 | 0.56 | 1 | 8.96 | 98 | 85 | 80 | 92 | 99 | 96 | | | | |
| | | | | (0) | | (13) | | (0) | | | | | |
| 1 | 0.56 | 2 | 8.96 | 90 | 90 | 10 | 90 | 90 | 98 | | | | |
| | | | | (0) | | (88) | | (8) | | | | | |
| 1 | 0.56 | 3 | 8.96 | 98 | 98 | 98 | 90 | 98 | 99 | | | | |
| | | | | (0) | | (0) | | (1) | | | | | |
| 1 | 0.56 | 4 | 8.96 | 95 | 90 | 98 | 98 | 90 | 98 | | | | |
| | | | | (0) | | (0) | | (8) | | | | | |
| 1 | 0.56 | 5 | 8.96 | 100 | 95 | 98 | 90 | 98 | 95 | | | | |
| | | | | (0) | | (0) | | (0) | | | | | |
| 1 | 0.56 | 6 | 8.96 | 80 | 85 | 20 | 98 | 85 | 96 | | | | |
| | | | | (5) | | (79) | | (11) | | | | | |
| 1 | 0.56 | 6 | 8.96 | | | | | 80 | 95 | | | | |
| | | | | | | | | (15) | | | | | |
| 1 | 0.56 | 7 | 8.96 | 80 | 97 | 50 | 97 | 85 | 98 | | | | |
| | | | | (17) | | (48) | | (13) | | | | | |
| 1 | 0.56 | 8 | 8.96 | 98 | 98 | 97 | 99 | 99 | 98 | | | | |
| | | | | (0) | | (2) | | (0) | | | | | |
| 1 | 0.56 | 9 | 8.96 | 98 | 96 | 80 | 90 | 99 | 100 | | | | |
| | | | | (0) | | (11) | | (1) | | | | | |
| 1 | 0.56 | 10 | 8.96 | 99 | 95 | 60 | 75 | 98 | 100 | | | | |
| | | | | (0) | | (20) | | (2) | | | | | |
| 1 | 0.56 | 11 | 8.96 | 100 | 98 | 96 | 97 | 100 | 99 | | | | |
| | | | | (0) | | (1) | | (0) | | | | | |
| 1 | 0.56 | 12 | 8.96 | 97 | 98 | 97 | 97 | 100 | 99 | | | | |
| | | | | (1) | | (0) | | (0) | | | | | |
| 1 | 0.56 | 13 | 8.96 | 98 | 98 | 60 | 97 | 100 | 99 | | | | |
| | | | | (0) | | (38) | | (0) | | | | | |
| 1 | 0.56 | 14 | 8.96 | 96 | 98 | 97 | 97 | 97 | 99 | | | | |
| | | | | (2) | | (0) | | (2) | | | | | |
| 1 | 0.56 | 15 | 8.96 | 100 | 98 | 80 | 95 | 100 | 97 | | | | |
| | | | | (0) | | (15) | | (0) | | | | | |
| 1 | 0.56 | 16 | 8.96 | 98 | 90 | 98 | 95 | 98 | 100 | | | | |
| | | | | (0) | | (0) | | (2) | | | | | |
| 1 | 0.56 | 17 | 8.96 | 90 | 90 | 40 | 95 | 100 | 100 | | | | |
| | | | | (0) | | (57) | | (0) | | | | | |
| 1 | 0.56 | 18 | 8.96 | 99 | 96 | 55 | 97 | 100 | 100 | | | | |
| | | | | (0) | | (43) | | (0) | | | | | |
| 1 | 0.56 | 19 | 8.96 | 98 | 98 | 98 | 97 | 99 | 100 | | | | |
| | | | | (0) | | (0) | | (1) | | | | | |
| 1 | 0.56 | 20 | 8.96 | 97 | 98 | 85 | 97 | 98 | 100 | | | | |
| | | | | (1) | | (12) | | (2) | | | | | |
| 1 | 0.56 | 21 | 8.96 | 100 | 98 | 95 | 96 | 100 | 100 | | | | |
| | | | | (0) | | (1) | | (0) | | | | | |
| 1 | 0.56 | 22 | 8.96 | 50 | 98 | 10 | 98 | 100 | 99 | | | | |
| | | | | (48) | | (89) | | (0) | | | | | |
| 1 | 0.56 | 23 | 8.96 | 90 | 99 | 20 | 90 | 100 | 100 | | | | |
| | | | | (9) | | (77) | | (0) | | | | | |
| 1 | 0.56 | 24 | 8.96 | 90 | 99 | 97 | 90 | 100 | 100 | | | | |
| | | | | (9) | | (0) | | (0) | | | | | |
| 1 | 0.56 | 25 | 8.96 | 97 | 99 | 40 | 90 | 100 | 100 | | | | |

TABLE II-continued

| HERBICIDE | | ANTIDOTE | | % PLANT INHIBITION AND % SAFENING EFFECT ( ) | | | | | | | | | |
|---|---|---|---|---|---|---|---|---|---|---|---|---|---|
| | | | | RICE | | SORGHUM | | WHEAT | | SOYBEAN | | CORN | |
| No. | RATE | No. | RATE | W | WO | W | WO | W | WO | W | WO | W | WO |
| 1 | 0.56 | 26 | 8.96 | 98 (2) | 98 | 95 (55) | 95 | 85 (0) | 95 | | | | |
| 1 | 0.56 | 27 | 8.96 | 85 (0) | 85 | 30 (0) | 90 | 90 (10) | 99 | | | | |
| 1 | 0.56 | 28 | 8.96 | 85 (0) | 85 | 0 (66) | 90 | 80 (9) | 99 | | | | |
| 1 | 0.56 | 29 | 8.96 | 85 (0) | 85 | 85 (100) | 90 | 90 (19) | 99 | | | | |
| 1 | 0.56 | 30 | 8.96 | 70 (0) | 85 | 0 (5) | 90 | 80 (9) | 99 | | | | |
| 1 | 0.56 | 31 | 8.96 | 80 (17) | 96 | 70 (100) | 98 | 85 (19) | 99 | | | | |
| 1 | 0.56 | 32 | 8.96 | 97 (16) | 96 | 99 (28) | 98 | 99 (14) | 99 | | | | |
| 1 | 0.56 | 33 | 8.96 | 99 (0) | 90 | 80 (0) | 95 | 100 (0) | 99 | | | | |
| 1 | 0.56 | 34 | 8.96 | | | | (15) | 98 (0) | 100 | | | | |
| 1 | 0.56 | 35 | 8.96 | 90 (5) | 95 | 50 (48) | 98 | 98 (2) | 95 | | | | |
| 1 | 0.56 | 36 | 8.96 | 90 (6) | 96 | 10 (89) | 98 | 97 (0) | 96 | | | | |
| 1 | 0.56 | 37 | 8.96 | | | | | 98 (0) | 100 | | | | |
| 1 | 0.56 | 38 | 8.96 | | | | | 100 (2) | 100 | | | | |
| 1 | 0.56 | 39 | 8.96 | | | | | 100 (0) | 100 | | | | |
| 1 | 0.56 | 40 | 8.96 | | | | | 100 (0) | 100 | | | | |
| 1 | 0.56 | 41 | 8.96 | | | | | 98 (0) | 100 | | | | |
| 1 | 0.56 | 42 | 8.96 | | | | | 85 (2) | 95 | | | | |
| 1 | 0.56 | 43 | 8.96 | | | | | 98 (10) | 90 | | | | |
| 1 | 0.56 | 44 | 8.96 | | | | | 95 (0) | 98 | | | | |
| 1 | 0.56 | 45 | 8.96 | | | | | 100 (3) | 95 | | | | |
| 1 | 0.56 | 46 | 8.96 | | | | | 100 (0) | 98 | | | | |
| 1 | 0.56 | 47 | 8.96 | | | | | 100 (0) | 98 | | | | |
| 1 | 0.56 | 48 | 8.96 | | | | | 100 (0) | 100 | | | | |
| 1 | 0.56 | 49 | 8.96 | | | | | 75 (0) | 80 | | | | |
| 1 | 0.56 | 50 | 8.96 | | | | | 100 (6) | 100 | | | | |
| 1 | 0.56 | 51 | 8.96 | | | | | 100 (0) | 100 | | | | |
| 1 | 0.56 | 52 | 8.96 | | | | | 100 (0) | 90 | | | | |
| 1 | 0.56 | 53 | 8.96 | | | | | 85 (0) | 100 | | | | |
| 1 | 0.56 | 54 | 8.96 | | | | | 100 (15) | 100 | | | | |
| 1 | 0.56 | 55 | 8.96 | | | | | 100 (0) | 100 | | | | |
| 1 | 0.56 | 56 | 8.96 | | | | | 100 (0) | 100 | | | | |
| 1 | 0.56 | 57 | 8.96 | | | | | 90 (0) | 90 | | | | |
| 1 | 0.56 | 58 | 8.96 | | | | | 100 (0) | 90 | | | | |
| 2 | 6.72 | 6 | 8.96 | 60 (0) | 45 | | | | | 90 (0) | 80 | | |
| 2 | 6.72 | 34 | 8.96 | 90 (0) | 75 | | | | | 90 (0) | 90 | | |
| 2 | 6.72 | 37 | 8.96 | 90 (0) | 75 | | | | | 98 (0) | 90 | | |
| 2 | 6.72 | 38 | 8.96 | 75 (0) | 75 | | | | | 98 (0) | 90 | | |
| 2 | 6.72 | 39 | 8.96 | 40 (46) | 75 | | | | | 90 (0) | 90 | | |
| 2 | 6.72 | 40 | 8.96 | 75 | 75 | | | | | 90 | 90 | | |

TABLE II-continued

| HERBICIDE | | ANTIDOTE | | % PLANT INHIBITION AND % SAFENING EFFECT ( ) | | | | | | | | | |
|---|---|---|---|---|---|---|---|---|---|---|---|---|---|
| | | | | RICE | | SORGHUM | | WHEAT | | SOYBEAN | | CORN | |
| No. | RATE | No. | RATE | W | WO | W | WO | W | WO | W | WO | W | WO |
| 2 | 6.72 | 41 | 8.96 | 70 | 75 (0) | | | | | 90 | 90 (0) | | |
| 2 | 6.72 | 42 | 8.96 | 50 | 70 (6) | | | | | 98 | 90 (0) | | |
| 2 | 6.72 | 43 | 8.96 | 60 | 50 (28) | | | | | 90 | 95 (0) | | |
| 2 | 6.72 | 44 | 8.96 | 95 | 85 (0) | | | | | 95 | 90 (5) | | |
| 2 | 6.72 | 45 | 8.96 | 95 | 65 (0) | | | | | 90 | 90 (0) | | |
| 2 | 6.72 | 46 | 8.96 | 98 | 90 (0) | | | | | 98 | 98 (0) | | |
| 2 | 6.72 | 47 | 8.96 | 98 | 90 (0) | | | | | 98 | 98 (0) | | |
| 2 | 6.72 | 48 | 8.96 | 98 | 100 (2) | | | | | 98 | 100 (2) | | |
| 2 | 4.48 | 49 | 8.96 | 90 | 75 (0) | | | | | 90 | 65 (0) | | |
| 2 | 4.48 | 50 | 8.96 | 100 | 95 (0) | | | | | 80 | 80 (0) | | |
| 2 | 4.48 | 51 | 8.96 | 10 | 99 (89) | | | | | 20 | 80 (75) | | |
| 2 | 4.48 | 52 | 8.96 | 100 | 75 (0) | | | | | 95 | 80 (0) | | |
| 2 | 4.48 | 53 | 8.96 | 95 | 90 (0) | | | | | 90 | 85 (0) | | |
| 2 | 4.48 | 54 | 8.96 | 95 | 90 (0) | | | | | 90 | 85 (0) | | |
| 2 | 4.48 | 55 | 8.96 | 80 | 80 (0) | | | | | 75 | 90 (16) | | |
| 2 | 4.48 | 56 | 8.96 | 95 | 80 (0) | | | | | 90 | 90 (0) | | |
| 2 | 4.48 | 57 | 8.96 | 90 | 85 (0) | | | | | 85 | 90 (5) | | |
| 2 | 4.48 | 58 | 8.96 | 85 | 85 (0) | | | | | 90 | 90 (0) | | |
| 4 | 4.48 | 1 | 8.96 | 100 | 100 (0) | 100 | 95 (0) | 100 | 100 (0) | | | | |
| 4 | 4.48 | 2 | 8.96 | 100 | 100 (0) | 98 | 98 (0) | 100 | 100 (0) | | | | |
| 4 | 2.24 | 3 | 8.96 | 90 | 99 (9) | 100 | 90 (0) | 70 | 70 (0) | | | | |
| 4 | 2.24 | 4 | 8.96 | 100 | 98 (0) | 80 | 95 (15) | 70 | 80 (12) | | | | |
| 4 | 2.24 | 5 | 8.96 | 100 | 98 (0) | 98 | 90 (0) | 70 | 75 (6) | | | | |
| 4 | 2.24 | 6 | 8.96 | 100 | 95 (0) | 40 | 98 (59) | 70 | 95 (26) | | | | |
| 4 | 2.24 | 6 | 8.96 | | | 10 | 90 (88) | 35 | 98 (64) | | | | |
| 4 | 2.24 | 7 | 8.96 | 99 | 98 (0) | 60 | 97 (38) | 60 | 80 (25) | | | | |
| 4 | 2.24 | 8 | 8.96 | 97 | 99 (2) | 100 | 99 (0) | 90 | 90 (0) | | | | |
| 4 | 2.24 | 9 | 8.96 | 96 | 96 (0) | 90 | 90 (0) | 85 | 95 (10) | | | | |
| 4 | 2.24 | 10 | 8.96 | 100 | 98 (0) | 80 | 80 (0) | 100 | 80 (0) | | | | |
| 4 | 2.24 | 11 | 8.96 | 100 | 95 (0) | 99 | 97 (0) | 95 | 90 (0) | | | | |
| 4 | 2.24 | 12 | 8.96 | 100 | 95 (0) | 95 | 97 (2) | 80 | 90 (11) | | | | |
| 4 | 2.24 | 13 | 8.96 | 100 | 95 (0) | 90 | 97 (7) | 85 | 90 (5) | | | | |
| 4 | 2.24 | 14 | 8.96 | 99 | 95 (0) | 100 | 97 (0) | 90 | 90 (0) | | | | |
| 4 | 2.24 | 15 | 8.96 | 100 | 99 (0) | 98 | 98 (0) | 98 | 98 (0) | | | | |
| 4 | 2.24 | 16 | 8.96 | 95 | 85 (0) | 100 | 98 (0) | 70 | 65 (0) | | | | |
| 4 | 2.24 | 17 | 8.96 | 90 | 85 (0) | 80 | 98 (18) | 70 | 65 (0) | | | | |
| 4 | 2.24 | 18 | 8.96 | 98 | 95 (0) | 70 | 97 (27) | 70 | 70 (0) | | | | |
| 4 | 2.24 | 19 | 8.96 | 100 | 96 (0) | 100 | 99 (0) | 90 | 90 (0) | | | | |
| 4 | 2.24 | 20 | 8.96 | 100 | 96 | 80 | 99 | 90 | 90 | | | | |

TABLE II-continued

% PLANT INHIBITION AND % SAFENING EFFECT ( )

| HERBICIDE | | ANTIDOTE | | RICE | | SORGHUM | | WHEAT | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 4 | 2.24 | 21 | 8.96 | 100 | (0) 99 | 97 | (19) 96 | 90 | (0) 95 | | | | |
| 4 | 2.24 | 22 | 8.96 | 100 | (0) 100 | 30 | (0) 97 | 95 | (5) 95 | | | | |
| 4 | 2.24 | 23 | 8.96 | 100 | (0) 100 | 80 | (69) 90 | 100 | (0) 85 | | | | |
| 4 | 2.24 | 24 | 8.96 | 100 | (0) 100 | 98 | (11) 90 | 90 | (0) 85 | | | | |
| 4 | 2.24 | 25 | 8.96 | 100 | (0) 100 | 75 | (0) 90 | 70 | (0) 85 | | | | |
| 4 | 2.24 | 26 | 8.96 | 99 | (0) 99 | 98 | (16) 98 | 90 | (17) 80 | | | | |
| 4 | 2.24 | 27 | 8.96 | 100 | (0) 99 | 40 | (0) 96 | 90 | (0) 90 | | | | |
| 4 | 2.24 | 28 | 8.96 | 100 | (0) 99 | 70 | (58) 96 | 95 | (0) 90 | | | | |
| 4 | 2.24 | 29 | 8.96 | 100 | (0) 99 | 99 | (27) 96 | 95 | (0) 90 | | | | |
| 4 | 2.24 | 30 | 8.96 | 100 | (0) 99 | 80 | (0) 96 | 98 | (0) 90 | | | | |
| 4 | 2.24 | 31 | 8.96 | 98 | (0) 97 | 95 | (16) 99 | 50 | (0) 70 | | | | |
| 4 | 2.24 | 32 | 8.96 | 97 | (0) 97 | 99 | (4) 99 | 85 | (28) 70 | | | | |
| 4 | 2.24 | 33 | 8.96 | 100 | (0) 97 | 80 | (0) 97 | 80 | (0) 80 | | | | |
| 4 | 2.24 | 34 | 8.96 | | | 90 | (17) 98 | 95 | (0) 90 | | | | |
| 4 | 2.24 | 35 | 8.96 | 100 | (0) 99 | 85 | (8) 98 | 70 | (0) 90 | | | | |
| 4 | 2.24 | 36 | 8.96 | 100 | (0) 99 | 50 | (13) 99 | 50 | (22) 95 | | | | |
| 4 | 2.24 | 37 | 8.96 | | | 45 | (49) 98 | 98 | (47) 90 | | | | |
| 4 | 2.24 | 38 | 8.96 | | | 98 | (54) 98 | 98 | (0) 90 | | | | |
| 4 | 2.24 | 39 | 8.96 | | | 100 | (0) 98 | 98 | (0) 90 | | | | |
| 4 | 2.24 | 40 | 8.96 | | | 30 | (0) 98 | 90 | (0) 90 | | | | |
| 4 | 2.24 | 41 | 8.96 | | | 98 | (69) 98 | 98 | (0) 90 | | | | |
| 4 | 2.24 | 42 | 8.96 | | | 100 | (0) 90 | 95 | (0) 95 | | | | |
| 4 | 2.24 | 43 | 8.96 | | | 10 | (0) 98 | 40 | (0) 90 | | | | |
| 4 | 2.24 | 44 | 8.96 | | | 30 | (89) 98 | 100 | (55) 95 | | | | |
| 4 | 2.24 | 45 | 8.96 | | | 10 | (69) 10 | 80 | (0) 85 | | | | |
| 4 | 2.24 | 46 | 8.96 | | | 100 | (0) 98 | 100 | (5) 98 | | | | |
| 4 | 2.24 | 47 | 8.96 | | | 98 | (0) 98 | 90 | (0) 98 | | | | |
| 4 | 2.24 | 48 | 8.96 | | | 60 | (0) 70 | 80 | (8) 90 | | | | |
| 4 | 2.24 | 49 | 8.96 | | | 100 | (14) 100 | 100 | (11) 90 | | | | |
| 4 | 2.24 | 50 | 8.96 | | | 80 | (0) 85 | 75 | (0) 80 | | | | |
| 4 | 2.24 | 51 | 8.96 | | | 50 | (5) 60 | 90 | (6) 80 | | | | |
| 4 | 2.24 | 52 | 8.96 | | | 35 | (16) 90 | 80 | (0) 90 | | | | |
| 4 | 2.24 | 53 | 8.96 | | | 60 | (61) 90 | 100 | (11) 85 | | | | |
| 4 | 2.24 | 54 | 8.96 | | | 80 | (33) 90 | 50 | (0) 75 | | | | |
| 4 | 2.24 | 55 | 8.96 | | | 80 | (11) 95 | 80 | (33) 80 | | | | |
| 4 | 2.24 | 56 | 8.96 | | | 55 | (15) 95 | 80 | (0) 80 | | | | |
| 4 | 2.24 | 57 | 8.96 | | | 95 | (42) 90 | 90 | (0) 85 | | | | |
| 4 | 2.24 | 58 | 8.96 | | | 95 | (0) 90 | 90 | (0) 85 | | | | |
| 6 | 6.72 | 1 | 8.96 | 90 | 62 | 80 | (0) 80 | 80 | (0) 60 | | | | |

TABLE II-continued

| HERBICIDE | | ANTIDOTE | | RICE | | SORGHUM | | WHEAT | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 6 | 6.72 | 2 | 8.96 | 90 | 70 (0) | 50 | 80 (0) | 80 | 50 (0) | | | | |
| 6 | 6.72 | 3 | 8.96 | 95 | 85 (0) | 90 | 80 (37) | 70 | 80 (0) | | | | |
| 6 | 6.72 | 4 | 8.96 | 80 | 80 (0) | 85 | 90 (0) | 85 | 80 (12) | | | | |
| 6 | 6.72 | 5 | 8.96 | 90 | 85 (0) | 95 | 90 (5) | 80 | 90 (0) | | | | |
| 6 | 6.72 | 6 | 8.96 | 90 | 80 (0) | | | | | | | | |
| 6 | 6.72 | 6 | 8.96 | 90 | 95 (5) | 50 | 98 (48) | 70 | 90 (22) | | | | |
| 6 | 6.72 | 7 | 8.96 | 75 | 90 (16) | 50 | 99 (49) | 80 | 90 (11) | | | | |
| 6 | 6.72 | 8 | 8.96 | 98 | 96 (0) | 97 | 99 (2) | 90 | 90 (0) | | | | |
| 6 | 6.72 | 9 | 8.96 | 97 | 97 (0) | 95 | 95 (0) | 95 | 97 (2) | | | | |
| 6 | 6.72 | 10 | 8.96 | 90 | 90 (0) | 50 | 60 (16) | 80 | 75 (0) | | | | |
| 6 | 6.72 | 11 | 8.96 | 96 | 90 (0) | 95 | 95 (0) | 95 | 90 (0) | | | | |
| 6 | 6.72 | 12 | 8.96 | 90 | 90 (0) | 90 | 95 (5) | 96 | 90 (0) | | | | |
| 6 | 6.72 | 13 | 8.96 | 95 | 90 (0) | 95 | 95 (0) | 96 | 90 (0) | | | | |
| 6 | 6.72 | 14 | 8.96 | 85 | 90 (5) | 95 | 95 (0) | 90 | 90 (0) | | | | |
| 6 | 6.72 | 15 | 8.96 | 97 | 90 (0) | 96 | 96 (0) | 90 | 90 (0) | | | | |
| 6 | 6.72 | 16 | 8.96 | 80 | 80 (0) | 70 | 98 (28) | 70 | 80 (12) | | | | |
| 6 | 6.72 | 17 | 8.96 | 65 | 80 (18) | 60 | 98 (38) | 80 | 80 (0) | | | | |
| 6 | 6.72 | 18 | 8.96 | 95 | 90 (0) | 75 | 95 (21) | 95 | 97 (2) | | | | |
| 6 | 6.72 | 19 | 8.96 | 85 | 90 (5) | 90 | 95 (5) | 90 | 85 (0) | | | | |
| 6 | 6.72 | 20 | 8.96 | 90 | 90 (0) | 90 | 95 (5) | 95 | 85 (0) | | | | |
| 6 | 6.72 | 21 | 8.96 | 96 | 97 (1) | 75 | 90 (16) | 90 | 90 (0) | | | | |
| 6 | 6.72 | 22 | 8.96 | 97 | 97 (0) | 50 | 90 (44) | 80 | 90 (11) | | | | |
| 6 | 6.72 | 23 | 8.96 | 98 | 97 (0) | 90 | 75 (0) | 95 | 80 (0) | | | | |
| 6 | 6.72 | 24 | 8.96 | 98 | 97 (0) | 70 | 75 (6) | 97 | 80 (0) | | | | |
| 6 | 6.72 | 25 | 8.96 | 96 | 97 (1) | 70 | 75 (6) | 90 | 80 (0) | | | | |
| 6 | 6.72 | 26 | 8.96 | 98 | 95 (0) | 99 | 95 (0) | 85 | 90 (5) | | | | |
| 6 | 6.72 | 27 | 8.96 | 85 | 95 (10) | 45 | 97 (53) | 35 | 85 (58) | | | | |
| 6 | 6.72 | 28 | 8.96 | 80 | 95 (15) | 70 | 97 (27) | 85 | 85 (0) | | | | |
| 6 | 6.72 | 29 | 8.96 | 75 | 95 (21) | 98 | 97 (0) | 95 | 85 (0) | | | | |
| 6 | 6.72 | 30 | 8.96 | 75 | 95 (21) | 65 | 97 (32) | 80 | 85 (5) | | | | |
| 6 | 6.72 | 31 | 8.96 | 96 | 90 (0) | 75 | 99 (24) | 70 | 85 (17) | | | | |
| 6 | 6.72 | 32 | 8.96 | 96 | 90 (0) | 97 | 99 (2) | 95 | 85 (0) | | | | |
| 6 | 6.72 | 33 | 8.96 | 98 | 95 (0) | 80 | 85 (5) | 96 | 85 (0) | | | | |
| 6 | 6.72 | 34 | 8.96 | 98 | 90 (0) | | | | | | | | |
| 6 | 6.72 | 35 | 8.96 | 95 | 97 (2) | 75 | 99 (24) | 65 | 95 (31) | | | | |
| 6 | 6.72 | 36 | 8.96 | 95 | 90 (0) | 65 | 97 (32) | 40 | 90 (55) | | | | |
| 6 | 6.72 | 37 | 8.96 | 90 | 90 (0) | | | | | | | | |
| 6 | 6.72 | 38 | 8.96 | 90 | 90 (0) | | | | | | | | |
| 6 | 6.72 | 39 | 8.96 | 85 | 90 | | | | | | | | |

TABLE II-continued

% PLANT INHIBITION AND % SAFENING EFFECT ( )

| HERBICIDE | | ANTIDOTE | | RICE | | SORGHUM | | WHEAT | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 6 | 6.72 | 40 | 8.96 | 90 | 90 (5) | | | | | | | | |
| 6 | 6.72 | 41 | 8.96 | 90 | 90 (0) | | | | | | | | |
| 6 | 6.72 | 42 | 8.96 | 75 | 80 (6) | | | | | | | | |
| 6 | 6.72 | 43 | 8.96 | 90 | 80 (0) | | | | | | | | |
| 6 | 6.72 | 44 | 8.96 | 90 | 85 (0) | | | | | | | | |
| 6 | 6.72 | 45 | 8.96 | 80 | 60 (0) | | | | | | | | |
| 6 | 6.72 | 46 | 8.96 | 98 | 98 (0) | | | | | | | | |
| 6 | 6.72 | 47 | 8.96 | 100 | 98 (0) | | | | | | | | |
| 6 | 6.72 | 48 | 8.96 | 95 | 98 (3) | | | | | | | | |
| 6 | 4.48 | 49 | 8.96 | 75 | 80 (6) | | | | | | | | |
| 6 | 4.48 | 50 | 8.96 | 70 | 80 (12) | | | | | | | | |
| 6 | 4.48 | 51 | 8.96 | 80 | 80 (0) | | | | | | | | |
| 6 | 4.48 | 52 | 8.96 | 60 | 85 (29) | | | | | | | | |
| 6 | 4.48 | 53 | 8.96 | 95 | 90 (0) | | | | | | | | |
| 6 | 4.48 | 54 | 8.96 | 90 | 90 (0) | | | | | | | | |
| 6 | 4.48 | 55 | 8.96 | 95 | 80 (0) | | | | | | | | |
| 6 | 4.48 | 56 | 8.96 | 85 | 80 (0) | | | | | | | | |
| 6 | 4.48 | 57 | 8.96 | 95 | 95 (0) | | | | | | | | |
| 6 | 4.48 | 58 | 8.96 | 95 | 95 (0) | | | | | | | | |
| 10 | 1.12 | 6 | 8.96 | | | | | | | | | 35 | 85 (58) |
| 10 | 1.12 | 6 | 8.96 | | | 30 | 98 (69) | | | | | 35 | 95 (63) |
| 10 | 1.12 | 7 | 8.96 | | | 70 | 98 (29) | | | | | 30 | 95 (68) |
| 10 | 1.12 | 34 | 8.96 | | | | | | | | | 98 | 95 (0) |
| 10 | 1.12 | 37 | 8.96 | | | | | | | | | 45 | 95 (52) |
| 10 | 1.12 | 38 | 8.96 | | | | | | | | | 95 | 95 (0) |
| 10 | 1.12 | 39 | 8.96 | | | | | | | | | 95 | 95 (0) |
| 10 | 1.12 | 40 | 8.96 | | | | | | | | | 95 | 95 (0) |
| 10 | 1.12 | 41 | 8.96 | | | | | | | | | 95 | 95 (0) |
| 10 | 1.12 | 42 | 8.96 | | | | | | | | | 95 | 95 (0) |
| 10 | 1.12 | 43 | 8.96 | | | | | | | | | 40 | 70 (42) |
| 10 | 1.12 | 44 | 8.96 | | | | | | | | | 65 | 95 (31) |
| 10 | 1.12 | 45 | 8.96 | | | | | | | | | 85 | 80 (0) |
| 10 | 1.12 | 46 | 8.96 | | | | | | | | | 85 | 95 (10) |
| 10 | 1.12 | 47 | 8.96 | | | | | | | | | 98 | 95 (0) |
| 10 | 1.12 | 48 | 8.96 | | | | | | | | | 90 | 95 (5) |
| 10 | 2.24 | 49 | 8.96 | | | | | | | | | 95 | 85 (0) |
| 10 | 2.24 | 50 | 8.96 | | | | | | | | | 70 | 85 (17) |
| 10 | 2.24 | 51 | 8.96 | | | | | | | | | 60 | 80 (25) |
| 10 | 2.24 | 52 | 8.96 | | | | | | | | | 55 | 90 |

TABLE II-continued

% PLANT INHIBITION AND % SAFENING EFFECT ( )

| HERBICIDE | | ANTIDOTE | | RICE | | SORGHUM | | WHEAT | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 10 | 2.24 | 53 | 8.96 | | | | | | | | | 85 | 90 (38) |
| 10 | 2.24 | 54 | 8.96 | | | | | | | | | 65 | 90 (5) |
| 10 | 2.24 | 55 | 8.96 | | | | | | | | | 90 | 90 (27) |
| 10 | 2.24 | 56 | 8.96 | | | | | | | | | 75 | 90 (0) |
| 10 | 2.24 | 57 | 8.96 | | | | | | | | | 100 | 95 (16) |
| 10 | 2.24 | 58 | 8.96 | | | | | | | | | 85 | 95 (0) |
| 3 | 2.24 | 6 | 8.96 | 100 | 99 (0) | 35 | 98 (64) | 70 | 98 (29) | | | 40 | 85 (53) |
| 3 | 0.14 | 6 | 8.96 | 0 | 30 (100) | 0 | 25 (100) | 0 | 25 (100) | | | 15 | 15 (0) |
| 3 | 0.56 | 6 | 8.96 | 70 | 70 (0) | 15 | 85 (82) | 10 | 65 (85) | | | 25 | 55 (55) |
| 5 | 4.48 | 6 | 8.96 | 70 | 70 (0) | 10 | 90 (89) | 30 | 75 (60) | | | 25 | 60 (58) |
| 5 | 1.12 | 6 | 8.96 | 60 | 50 (0) | 20 | 60 (67) | 0 | 40 (100) | | | 0 | 20 (100) |
| 5 | 0.28 | 6 | 8.96 | 10 | 20 (50) | 0 | 50 (100) | 0 | 10 (100) | | | 0 | 0 (0) |
| 8 | 2.24 | 6 | 8.96 | 90 | 90 (0) | 90 | 100 (10) | 70 | 80 (13) | | | 70 | 80 (13) |
| 8 | 0.14 | 6 | 8.96 | 0 | 20 (100) | 0 | 50 (100) | 10 | 25 (60) | | | 10 | 20 (50) |
| 8 | 0.56 | 6 | 8.96 | 50 | 50 (100) | 20 | 85 (76) | 30 | 70 (57) | | | 20 | 70 (71) |
| 11 | 0.14 | 6 | 8.96 | 0 | 60 (100) | 20 | 75 (73) | 70 | 70 (0) | | | 20 | 70 (71) |
| 11 | 0.56 | 6 | 8.96 | 50 | 95 (47) | 90 | 99 (9) | 60 | 99 (39) | | | 80 | 85 (6) |
| 11 | 2.24 | 6 | 8.96 | 98 | 100 (2) | 98 | 100 (2) | 98 | 100 (2) | | | 90 | 98 (8) |
| 13 | 1.12 | 6 | 8.96 | 100 | 95 (0) | 10 | 99 (90) | 50 | 70 (29) | | | 10 | 40 (75) |
| 13 | 4.48 | 6 | 8.96 | 100 | 100 (0) | 70 | 99 (29) | 75 | 95 (21) | | | 35 | 60 (42) |
| 13 | 0.28 | 6 | 8.96 | 30 | 85 (65) | 0 | 90 (100) | 10 | 40 (75) | | | 10 | 20 (50) |
| 14 | 1.12 | 6 | 8.96 | | | 90 | 100 (10) | | | | | 45 | 95 (53) |
| 16 | 1.12 | 6 | 8.96 | | | 100 | 100 (0) | | | | | 75 | 98 (23) |
| 16 | 0.56 | 6 | 8.96 | 90 | 90 (0) | 60 | 100 (40) | 50 | 85 (41) | | | 50 | 90 (44) |
| 16 | 0.14 | 6 | 8.96 | 50 | 70 (29) | 30 | 99 (70) | 40 | 65 (38) | | | 15 | 25 (40) |
| 16 | 2.24 | 6 | 8.96 | 100 | 98 (0) | 100 | 100 (0) | 85 | 95 (11) | | | 90 | 99 (9) |
| 17 | 0.14 | 6 | 8.96 | 10 | 25 (60) | 0 | 60 (100) | 30 | 40 (25) | | | 0 | 25 (100) |
| 17 | 0.56 | 6 | 8.96 | 99 | 90 (0) | 70 | 95 (26) | 70 | 85 (18) | | | 10 | 50 (80) |
| 17 | 2.24 | 6 | 8.96 | 100 | 98 (0) | 98 | 99 (1) | 90 | 99 (9) | | | 30 | 80 (63) |
| 18 | 4.48 | 6 | 8.96 | 100 | 100 (0) | 40 | 99 (51) | 100 | 100 (0) | | | 50 | 99 (49) |
| 18 | 0.28 | 6 | 8.96 | 65 | 80 (19) | 0 | 90 (100) | 50 | 90 (44) | | | 20 | 60 (67) |
| 18 | 1.12 | 6 | 8.96 | 99 | 97 (0) | 10 | 97 (90) | 98 | 97 (0) | | | 50 | 95 (47) |
| 19 | 2.24 | 6 | 8.96 | 98 | 97 (0) | 100 | 100 (0) | 95 | 90 (0) | | | 60 | 95 (37) |
| 19 | 0.14 | 6 | 8.96 | 0 | 10 (100) | 10 | 90 (89) | 50 | 60 (17) | | | 25 | 25 (0) |
| 19 | 0.56 | 6 | 8.96 | 50 | 70 (29) | 80 | 100 (20) | 80 | 85 (6) | | | 65 | 60 (0) |
| 20 | 2.24 | 6 | 8.96 | 90 | 90 (0) | 98 | 100 (2) | 35 | 70 (50) | | | 80 | 50 (0) |
| 20 | 0.14 | 6 | 8.96 | 0 | 0 (0) | 0 | 70 (100) | 0 | 30 (100) | | | 20 | 20 (0) |
| 20 | 0.56 | 6 | 8.96 | 50 | 50 (0) | 75 | 100 (25) | 25 | 30 (17) | | | 20 | 40 (50) |

EXAMPLE 62

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide + antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (Kg/ha), based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a bench in a greenhouse and sub-irrigated as required for the duration of the test. Plant response was observed about three weeks after initial treatment. Results are reported in Table III.

TABLE III

| HERBICIDE | | ANTIDOTE | | SORGHUM | WHEAT | RICE | SOYBEAN | CORN |
|---|---|---|---|---|---|---|---|---|
| No. | RATE | No. | RATE | W WO | W WO | W WO | W WO | W WO |
| 1 | 0.56 | 4 | 0.28 | | 100 95 (0) | | | |
| 1 | 0.56 | 5 | 0.28 | | 95 95 (0) | | | |
| 1 | 0.56 | 6 | 0.28 | | 70 100 (30) | | | |
| 1 | 0.56 | 8 | 0.28 | | 100 95 (0) | | | |
| 1 | 0.56 | 9 | 0.28 | | 95 95 (0) | | | |
| 1 | 0.56 | 12 | 0.28 | | 100 95 (0) | | | |
| 1 | 0.56 | 14 | 0.28 | | 100 95 (0) | | | |
| 1 | 0.56 | 15 | 0.28 | | 100 95 (0) | | | |
| 1 | 0.56 | 19 | 0.28 | | 100 95 (0) | | | |
| 1 | 0.56 | 20 | 0.28 | | 95 95 (0) | | | |
| 1 | 0.56 | 21 | 0.28 | | 95 95 (0) | | | |
| 1 | 0.56 | 24 | 0.28 | | 95 95 (0) | | | |
| 1 | 0.56 | 26 | 0.28 | | 95 95 (0) | | | |
| 1 | 0.56 | 28 | 0.28 | | 95 100 (5) | | | |
| 1 | 0.56 | 30 | 0.28 | | 100 100 (0) | | | |
| 1 | 0.56 | 32 | 0.28 | | 100 95 (0) | | | |
| 1 | 0.56 | 33 | 0.28 | | 100 95 (0) | | | |
| 1 | 0.56 | 34 | 0.28 | | 100 95 (0) | | | |
| 1 | 0.56 | 41 | 0.28 | | 95 95 (0) | | | |
| 1 | 0.56 | 46 | 0.28 | | 100 95 (0) | | | |
| 1 | 0.56 | 47 | 0.28 | | 95 95 (0) | | | |
| 1 | 0.56 | 48 | 0.28 | | 80 95 (15) | | | |
| 1 | 0.56 | 59 | 0.28 | | 100 95 (0) | | | |
| 1 | 0.56 | 60 | 0.28 | | 100 100 (0) | | | |
| 2 | 4.48 | 4 | 0.28 | | | | 100 100 (0) | 100 100 (0) |
| 2 | 4.48 | 5 | 0.28 | | | | 100 100 (0) | 100 100 (0) |
| 2 | 6.72 | 6 | 0.28 | | | | 100 100 (0) | 100 100 (0) |
| 2 | 4.48 | 8 | 0.28 | | | | 100 100 (0) | 100 100 (0) |
| 2 | 4.48 | 9 | 0.28 | | | | 100 100 (0) | 100 100 (0) |
| 2 | 4.48 | 12 | 0.28 | | | | 100 100 (0) | 100 100 (0) |
| 2 | 4.48 | 14 | 0.28 | | | | 100 100 | 100 100 |

TABLE III-continued

| | | | | % PLANT INHIBITION AND % SAFENING EFFECT ( ) | | | | |
|---|---|---|---|---|---|---|---|---|
| HERBICIDE | | ANTIDOTE | | SORGHUM | WHEAT | RICE | SOYBEAN | CORN |
| No. | RATE | No. | RATE | W WO | W WO | W WO | W WO | W WO |
| 2 | 4.48 | 15 | 0.28 | | | 80 95 (15) | 90 90 (0) | |
| 2 | 4.48 | 19 | 0.28 | | | 100 100 (0) | 100 100 (0) | |
| 2 | 6.72 | 20 | 0.28 | | | | 100 100 (0) | |
| 2 | 6.72 | 20 | 0.28 | | | 85 95 (10) | | |
| 2 | 4.48 | 21 | 0.28 | | | 100 100 (0) | 100 100 (0) | |
| 2 | 4.48 | 24 | 0.28 | | | 60 95 (36) | 80 90 (11) | |
| 2 | 4.48 | 26 | 0.28 | | | 100 95 (0) | 95 90 (0) | |
| 2 | 6.72 | 28 | 0.28 | | | 70 85 (17) | 100 90 (0) | |
| 2 | 6.72 | 30 | 0.28 | | | 80 85 (5) | 100 90 (0) | |
| 2 | 4.48 | 32 | 0.28 | | | 100 95 (0) | 95 90 (0) | |
| 2 | 4.48 | 33 | 0.28 | | | 100 100 (0) | 100 100 (0) | |
| 2 | 4.48 | 34 | 0.28 | | | 85 95 (10) | 85 90 (11) | |
| 2 | 4.48 | 41 | 0.28 | | | 65 95 (31) | 70 90 (22) | |
| 2 | 4.48 | 46 | 0.28 | | | 85 95 (10) | 85 90 (5) | |
| 2 | 4.48 | 47 | 0.28 | | | 70 95 (26) | 90 90 (0) | |
| 2 | 4.48 | 48 | 0.28 | | | 100 95 (0) | 100 90 (0) | |
| 2 | 4.48 | 59 | 0.28 | | | 90 90 (0) | 95 95 (0) | |
| 2 | 6.72 | 60 | 0.28 | | | | 70 75 (6) | |
| 4 | 2.24 | 4 | 0.28 | 100 100 (0) | 35 75 (54) | | | |
| 4 | 2.24 | 5 | 0.28 | 100 100 (0) | 40 75 (46) | | | |
| 4 | 2.24 | 6 | 0.28 | 0 95 (100) | 70 85 (17) | | | |
| 4 | 2.24 | 8 | 0.28 | 100 100 (0) | 85 75 (0) | | | |
| 4 | 2.24 | 9 | 0.28 | 56 100 (45) | 60 75 (20) | | | |
| 4 | 2.24 | 12 | 0.28 | 100 100 (0) | 90 75 (0) | | | |
| 4 | 2.24 | 14 | 0.28 | 95 100 (5) | 51 75 (33) | | | |
| 4 | 2.24 | 15 | 0.28 | 100 100 (0) | 70 80 (12) | | | |
| 4 | 2.24 | 19 | 0.28 | 95 100 (5) | 75 75 (0) | | | |
| 4 | 2.24 | 20 | 0.28 | 100 100 (0) | 95 100 (5) | | | |
| 4 | 2.24 | 21 | 0.28 | 95 100 (5) | 35 75 (54) | | | |
| 4 | 2.24 | 24 | 0.28 | 95 100 (5) | 60 80 (25) | | | |
| 4 | 2.24 | 26 | 0.28 | 35 100 (65) | 60 80 (25) | | | |
| 4 | 2.24 | 28 | 0.28 | 70 100 (30) | 85 80 (0) | | | |
| 4 | 2.24 | 30 | 0.28 | 20 100 (80) | 70 80 (12) | | | |
| 4 | 2.24 | 32 | 0.28 | 100 100 (0) | 80 80 (0) | | | |
| 4 | 2.24 | 33 | 0.28 | 100 100 (0) | 70 75 (6) | | | |
| 4 | 2.24 | 34 | 0.28 | 95 100 (5) | 51 80 (37) | | | |
| 4 | 2.24 | 41 | 0.28 | 90 100 (10) | 51 80 (37) | | | |
| 4 | 2.24 | 46 | 0.28 | 95 100 (5) | 85 80 (0) | | | |
| 4 | 2.24 | 47 | 0.28 | 100 100 | 65 80 | | | |

TABLE III-continued

| HERBICIDE | | ANTIDOTE | | SORGHUM | WHEAT | RICE | SOYBEAN | CORN |
|---|---|---|---|---|---|---|---|---|
| No. | RATE | No. | RATE | W WO | W WO | W WO | W WO | W WO |
| | | | | (0) | (18) | | | |
| 4 | 2.24 | 48 | 0.28 | 80 100 | 45 80 | | | |
| | | | | (20) | (43) | | | |
| 4 | 2.24 | 59 | 0.28 | 70 100 | 70 95 | | | |
| | | | | (30) | (26) | | | |
| 4 | 2.24 | 60 | 0.28 | 100 100 | 45 70 | | | |
| | | | | (0) | (35) | | | |
| 6 | 4.48 | 4 | 0.28 | | | 95 90 | | |
| | | | | | | (0) | | |
| 6 | 4.48 | 5 | 0.28 | | | 90 90 | | |
| | | | | | | (0) | | |
| 6 | 4.48 | 6 | 0.28 | | | 85 95 | | |
| | | | | | | (10) | | |
| 6 | 4.48 | 8 | 0.28 | | | 95 90 | | |
| | | | | | | (0) | | |
| 6 | 4.48 | 9 | 0.28 | | | 95 90 | | |
| | | | | | | (0) | | |
| 6 | 4.48 | 12 | 0.28 | | | 100 90 | | |
| | | | | | | (0) | | |
| 6 | 4.48 | 14 | 0.28 | | | 95 90 | | |
| | | | | | | (0) | | |
| 6 | 4.48 | 15 | 0.28 | | | 95 85 | | |
| | | | | | | (0) | | |
| 6 | 4.48 | 19 | 0.28 | | | 85 90 | | |
| | | | | | | (5) | | |
| 6 | 4.48 | 20 | 0.28 | | | 100 95 | | |
| | | | | | | (0) | | |
| 6 | 4.48 | 21 | 0.28 | | | 95 90 | | |
| | | | | | | (0) | | |
| 6 | 4.48 | 24 | 0.28 | | | 95 85 | | |
| | | | | | | (0) | | |
| 6 | 4.48 | 26 | 0.28 | | | 90 85 | | |
| | | | | | | (0) | | |
| 6 | 4.48 | 28 | 0.28 | | | 90 90 | | |
| | | | | | | (0) | | |
| 6 | 4.48 | 30 | 0.28 | | | 50 90 | | |
| | | | | | | (44) | | |
| 6 | 4.48 | 32 | 0.28 | | | 95 85 | | |
| | | | | | | (0) | | |
| 6 | 4.48 | 33 | 0.28 | | | 100 90 | | |
| | | | | | | (0) | | |
| 6 | 4.48 | 34 | 0.28 | | | 95 85 | | |
| | | | | | | (0) | | |
| 6 | 4.48 | 41 | 0.28 | | | 100 85 | | |
| | | | | | | (0) | | |
| 6 | 4.48 | 46 | 0.28 | | | 90 85 | | |
| | | | | | | (0) | | |
| 6 | 4.48 | 47 | 0.28 | | | 90 85 | | |
| | | | | | | (0) | | |
| 6 | 4.48 | 48 | 0.28 | | | 95 85 | | |
| | | | | | | (0) | | |
| 6 | 4.48 | 59 | 0.28 | | | 85 95 | | |
| | | | | | | (10) | | |
| 6 | 4.48 | 60 | 0.28 | | | 90 85 | | |
| | | | | | | (0) | | |
| 10 | 2.24 | 4 | 0.28 | | | | 40 40 | 95 95 |
| | | | | | | | (0) | (0) |
| 10 | 2.24 | 5 | 0.28 | | | | 40 40 | 70 95 |
| | | | | | | | (0) | (26) |
| 10 | 2.24 | 6 | 0.28 | | | | | 85 95 |
| | | | | | | | | (10) |
| 10 | 2.24 | 6 | 0.28 | | | | 50 50 | 0 95 |
| | | | | | | | (0) | (100) |
| 10 | 2.24 | 8 | 0.28 | | | | 60 40 | 90 95 |
| | | | | | | | (0) | (5) |
| 10 | 2.24 | 9 | 0.28 | | | | 60 40 | 95 95 |
| | | | | | | | (0) | (0) |
| 10 | 2.24 | 10 | 0.28 | | | | 30 50 | 95 95 |
| | | | | | | | (40) | (0) |
| 10 | 2.24 | 12 | 0.28 | | | | 40 40 | 95 95 |
| | | | | | | | (0) | (0) |
| 10 | 2.24 | 13 | 0.28 | | | | 10 50 | 80 95 |
| | | | | | | | (80) | (15) |
| 10 | 2.24 | 14 | 0.28 | | | | 30 40 | 95 95 |
| | | | | | | | (25) | (0) |
| 10 | 2.24 | 15 | 0.28 | | | | 50 50 | 95 95 |
| | | | | | | | (0) | (0) |
| 10 | 2.24 | 16 | 0.28 | | | | 60 50 | 85 95 |

TABLE III-continued

% PLANT INHIBITION AND % SAFENING EFFECT ( )

| HERBICIDE | | ANTIDOTE | | SORGHUM | WHEAT | RICE | SOYBEAN | CORN |
|---|---|---|---|---|---|---|---|---|
| No. | RATE | No. | RATE | W WO | W WO | W WO | W WO | W WO |
| 10 | 2.24 | 18 | 0.28 | | | | 50 50 (0) | 95 95 (10) |
| 10 | 2.24 | 19 | 0.28 | | | | 40 40 (0) | 90 95 (0) |
| 10 | 2.24 | 20 | 0.28 | | | | (0) | 95 95 (5) |
| 10 | 2.24 | 20 | 0.28 | | | | 50 60 (16) | |
| 10 | 2.24 | 21 | 0.28 | | | | 50 40 (0) | 90 95 (5) |
| 10 | 2.24 | 23 | 0.28 | | | | 45 50 (10) | 80 95 (15) |
| 10 | 2.24 | 24 | 0.28 | | | | 50 50 (0) | 95 95 (0) |
| 10 | 2.24 | 25 | 0.28 | | | | 10 50 (80) | 80 95 (15) |
| 10 | 2.24 | 26 | 0.28 | | | | 60 50 (0) | 70 95 (26) |
| 10 | 2.24 | 27 | 0.28 | | | | 10 50 (80) | 90 95 (5) |
| 10 | 2.24 | 28 | 0.28 | | | | 70 65 (0) | 95 95 (0) |
| 10 | 2.24 | 30 | 0.28 | | | | 20 65 (69) | 25 95 (73) |
| 10 | 2.24 | 31 | 0.28 | | | | 50 50 (0) | 80 95 (15) |
| 10 | 2.24 | 32 | 0.28 | | | | 50 50 (0) | 95 95 (0) |
| 10 | 2.24 | 33 | 0.28 | | | | 60 40 (0) | 95 95 (0) |
| 10 | 2.24 | 34 | 0.28 | | | | 40 50 (20) | 95 95 (0) |
| 10 | 2.24 | 36 | 0.28 | | | | 50 50 (0) | 75 95 (21) |
| 10 | 2.24 | 37 | 0.28 | | | | 55 50 (0) | 40 95 (58) |
| 10 | 2.24 | 39 | 0.28 | | | | 50 50 (0) | 95 95 (0) |
| 10 | 2.24 | 40 | 0.28 | | | | 45 50 (10) | 80 95 (15) |
| 10 | 2.24 | 41 | 0.28 | | | | 40 50 (20) | 95 95 (0) |
| 10 | 2.24 | 42 | 0.28 | | | | 70 50 (0) | 95 95 (0) |
| 10 | 2.24 | 44 | 0.28 | | | | 45 50 (10) | 30 95 (68) |
| 10 | 2.24 | 45 | 0.28 | | | | 70 50 (0) | 95 95 (0) |
| 10 | 2.24 | 46 | 0.28 | | | | 35 50 (30) | 60 95 (36) |
| 10 | 2.24 | 47 | 0.28 | | | | 50 50 (0) | 95 95 (0) |
| 10 | 2.24 | 48 | 0.28 | | | | 45 50 (10) | 60 95 (36) |
| 10 | 2.24 | 53 | 0.28 | | | | 30 50 (40) | 70 95 (26) |
| 10 | 2.24 | 59 | 0.28 | | | | 70 60 (0) | 95 95 (0) |
| 10 | 2.24 | 60 | 0.28 | | | | 95 75 (0) | 95 90 (0) |

EXAMPLE 63

The procedure of Example 61 was followed to determine the interaction between herbicide and antidote when both are incorporated in a soil cover layer before emergence of the crop species. In this series of tests, however, all containers were seeded with at least one weed species in addition to crop seed. Results are reported in Table IV.

TABLE IV

% PLANT INHIBITION AND % SAFENING EFFECT ( )

| HERBICIDE | | ANTIDOTE | | RICE | | WHEAT | | SORGHUM | | SOYBEAN | | HEMP SESBANIA | | VELVET LEAF | |
|---|---|---|---|---|---|---|---|---|---|---|---|---|---|---|---|
| No. | RATE | No. | RATE | W | WO | W | WO | W | WO | W | WO | W | WO | W | WO |
| 2 | 1.12 | 51 | 8.96 | 40 | 40 (0) | | | | | 70 | 35 (0) | 90 | 99 (9) | 100 | 90 (0) |

TABLE IV -continued

% PLANT INHIBITION AND % SAFENING EFFECT ( )

| | | | | | | | | | | | | | |
|---|---|---|---|---|---|---|---|---|---|---|---|---|---|
| 2 | 2.24 | 51 | 8.96 | 50 | 75 (33) | | | 35 | 60 (41) | 100 | 100 (0) | 100 | 99 (0) |
| 2 | 4.48 | 51 | 8.96 | 20 | 80 (75) | | | 40 | 90 (55) | 100 | 100 (0) | 100 | 100 (0) |
| 2 | 6.72 | 52 | 8.96 | 100 | 95 (0) | | | 100 | 95 (0) | 100 | 100 (0) | 100 | 100 (0) |

| HERBICIDE | | ANTIDOTE | | RICE | | WHEAT | | SORGHUM | | SOYBEAN | | SUGAR BEET | | GREEN FOXTAIL | |
|---|---|---|---|---|---|---|---|---|---|---|---|---|---|---|---|
| No. | RATE | No. | RATE | W | WO | W | WO | W | WO | W | WO | W | WO | W | WO |
| 4 | 0.56 | 4 | 2.24 | | | 80 | 50 (0) | 100 | 100 (0) | | | 40 | 80 (50) | 100 | 100 (0) |
| 4 | 0.56 | 4 | 8.96 | | | 90 | 50 (0) | 100 | 100 (0) | | | 60 | 80 (25) | 100 | 100 (0) |
| 4 | 2.24 | 4 | 2.24 | | | 95 | 90 (0) | 95 | 100 (5) | | | 55 | 80 (31) | 100 | 100 (0) |
| 4 | 2.24 | 4 | 8.96 | | | 90 | 90 (0) | 100 | 100 (0) | | | 70 | 80 (12) | 100 | 100 (0) |
| 4 | 0.56 | 6 | 2.24 | | | 15 | 35 (57) | 0 | 75 (100) | | | 80 | 70 (0) | 80 | 95 (15) |
| 4 | 0.56 | 6 | 8.96 | | | 15 | 35 (57) | 0 | 75 (100) | | | 90 | 70 (0) | 90 | 95 (5) |
| 4 | 0.56 | 6 | 8.96 | | | 40 | 40 (0) | 0 | 70 (100) | | | | | 90 | 95 (5) |
| 4 | 1.12 | 6 | 8.96 | | | 45 | 50 (10) | 0 | 90 (100) | | | | | 98 | 98 (0) |
| 4 | 2.24 | 6 | 2.24 | | | 55 | 60 (8) | 0 | 95 (100) | | | 80 | 60 (0) | 100 | 100 (0) |
| 4 | 2.24 | 6 | 8.96 | | | 10 | 60 (83) | 10 | 95 (89) | | | 100 | 60 (0) | 100 | 100 (0) |
| 4 | 2.24 | 6 | 8.96 | | | 70 | 65 (0) | 15 | 95 (84) | | | | | 98 | 98 (0) |
| 4 | 4.48 | 6 | 8.96 | | | 90 | 80 (0) | 20 | 98 (79) | | | | | 100 | 98 (0) |
| 4 | 0.56 | 7 | 8.96 | | | 10 | 40 (75) | 0 | 70 (100) | | | | | 85 | 95 (10) |
| 4 | 1.12 | 7 | 8.96 | | | 50 | 50 (0) | 0 | 90 (100) | | | | | 90 | 98 (8) |
| 4 | 2.24 | 7 | 8.96 | | | 80 | 65 (0) | 20 | 95 (78) | | | | | 98 | 98 (0) |
| 4 | 4.48 | 7 | 8.96 | | | 80 | 80 (0) | 30 | 98 (69) | | | | | 99 | 98 (0) |
| 4 | 0.56 | 9 | 2.24 | | | 20 | 60 (66) | 100 | 100 (0) | | | 95 | 85 (0) | 100 | 100 (0) |
| 4 | 0.56 | 9 | 8.96 | | | 40 | 60 (33) | 75 | 100 (25) | | | 90 | 85 (0) | 100 | 100 (0) |
| 4 | 2.24 | 9 | 2.24 | | | 75 | 75 (0) | 100 | 100 (0) | | | 90 | 85 (0) | 100 | 100 (0) |
| 4 | 2.24 | 9 | 8.96 | | | 90 | 75 (0) | 95 | 100 (5) | | | 95 | 85 (0) | 100 | 100 (0) |
| 4 | 0.56 | 18 | 8.96 | | | 50 | 60 (16) | 60 | 85 (29) | | | | | 100 | 98 (0) |
| 4 | 1.12 | 18 | 8.96 | | | 60 | 70 (14) | 60 | 90 (33) | | | | | 100 | 98 (0) |
| 4 | 2.24 | 18 | 8.96 | | | 90 | 85 (0) | 80 | 98 (18) | | | | | 100 | 99 (0) |
| 4 | 4.48 | 18 | 8.96 | | | 90 | 90 (0) | 80 | 100 (20) | | | | | 100 | 100 (0) |
| 4 | 0.56 | 21 | 2.24 | | | 70 | 90 (22) | | | | | | | 100 | 100 (0) |
| 4 | 0.56 | 21 | 8.96 | | | 75 | 90 (16) | | | | | | | 100 | 100 (0) |
| 4 | 2.24 | 21 | 2.24 | | | 95 | 95 (0) | | | | | | | 100 | 100 (0) |
| 4 | 2.24 | 21 | 8.96 | | | 90 | 95 (5) | | | | | | | 100 | 100 (0) |
| 4 | 0.56 | 22 | 8.96 | | | 50 | 70 (28) | 0 | 20 (100) | | | | | 85 | 92 (7) |
| 4 | 1.12 | 22 | 8.96 | | | 70 | 80 (12) | 0 | 60 (100) | | | | | 98 | 98 (0) |
| 4 | 2.24 | 22 | 8.96 | | | 80 | 90 (11) | 10 | 80 (87) | | | | | 98 | 100 (2) |
| 4 | 4.48 | 22 | 8.96 | | | 90 | 98 (8) | 40 | 92 (56) | | | | | 98 | 100 (2) |
| 4 | 0.56 | 26 | 2.24 | | | 55 | 60 (8) | 90 | 100 (10) | | | 80 | 85 (5) | 100 | 100 (0) |
| 4 | 0.56 | 26 | 8.96 | | | 75 | 60 (0) | 50 | 100 (50) | | | 100 | 85 (0) | 100 | 100 (0) |
| 4 | 2.24 | 26 | 2.24 | | | 90 | 75 (0) | 100 | 100 (0) | | | 85 | 85 (0) | 100 | 100 (0) |
| 4 | 2.24 | 26 | 8.96 | | | 95 | 75 | 85 | 100 | | | 95 | 85 | 100 | 100 |

TABLE IV - continued

% PLANT INHIBITION AND % SAFENING EFFECT ( )

*(Continued from previous page — trailing safening values: (0), (15), (0), (0))*

| Herbicide No. | Rate | Antidote No. | Rate | Rice W/WO (Saf) | Soybean W/WO (Saf) | Corn W/WO (Saf) | Barnyard Grass W/WO (Saf) | Green Foxtail W/WO (Saf) |
|---|---|---|---|---|---|---|---|---|
| 4 | 0.56 | 27 | 8.96 | 30 / 60 (50) | 0 / 80 (100) | | | 85 / 80 (0) |
| 4 | 1.12 | 27 | 8.96 | 65 / 70 (7) | 20 / 80 (75) | | | 95 / 85 (0) |
| 4 | 2.24 | 27 | 8.96 | 55 / 80 (31) | 20 / 95 (78) | | | 97 / 90 (0) |
| 4 | 4.48 | 27 | 8.96 | 75 / 85 (11) | 40 / 90 (55) | | | 99 / 90 (0) |
| 4 | 0.56 | 28 | 8.96 | 0 / 60 (100) | 0 / 80 (100) | | | 80 / 80 (0) |
| 4 | 1.12 | 28 | 8.96 | 80 / 70 (0) | 20 / 80 (75) | | | 95 / 85 (0) |
| 4 | 2.24 | 28 | 8.96 | 90 / 80 (0) | 10 / 95 (89) | | | 90 / 90 (0) |
| 4 | 4.48 | 28 | 8.96 | 80 / 85 (5) | 30 / 90 (66) | | | 85 / 90 (5) |
| 4 | 0.56 | 36 | 8.96 | 0 / 60 (100) | 10 / 99 (89) | | | 95 / 85 (0) |
| 4 | 1.12 | 36 | 8.96 | 50 / 99 (49) | 40 / 80 (50) | | | 98 / 95 (0) |
| 4 | 2.24 | 36 | 8.96 | 75 / 75 (0) | 65 / 99 (34) | | | 98 / 98 (0) |
| 4 | 4.48 | 36 | 8.96 | 60 / 90 (33) | 60 / 99 (39) | | | 99 / 98 (0) |
| 4 | 0.56 | 37 | 8.96 | 25 / 60 (58) | 0 / 20 (100) | | 50 / 20 (0) | 95 / 100 (5) |
| 4 | 1.12 | 37 | 8.96 | 90 / 70 (0) | 35 / 60 (41) | | 50 / 30 (0) | 99 / 100 (1) |
| 4 | 2.24 | 37 | 8.96 | 95 / 95 (0) | 35 / 90 (61) | | 90 / 30 (0) | 100 / 100 (0) |
| 4 | 4.48 | 37 | 8.96 | 80 / 90 (11) | 40 / 96 (58) | | 98 / 50 (0) | 99 / 100 (1) |
| 4 | 0.56 | 40 | 8.96 | 60 / 60 (0) | 20 / 20 (0) | | 30 / 20 (0) | 100 / 100 (0) |
| 4 | 1.12 | 40 | 8.96 | 90 / 70 (0) | 35 / 60 (41) | | 70 / 30 (0) | 100 / 100 (0) |
| 4 | 2.24 | 40 | 8.96 | 97 / 95 (0) | 35 / 90 (61) | | 90 / 30 (0) | 99 / 100 (1) |
| 4 | 4.48 | 40 | 8.96 | 90 / 90 (0) | 90 / 96 (6) | | 98 / 50 (0) | 99 / 100 (1) |
| 4 | 0.56 | 43 | 8.96 | 20 / 20 (0) | 0 / 10 (100) | | 70 / 50 (0) | 95 / 90 (0) |
| 4 | 1.12 | 43 | 8.96 | 20 / 50 (60) | 0 / 40 (100) | | 70 / 50 (0) | 95 / 98 (3) |
| 4 | 2.24 | 43 | 8.96 | 20 / 70 (71) | 30 / 60 (50) | | 90 / 60 (0) | 97 / 95 (0) |
| 4 | 4.48 | 43 | 8.96 | 80 / 75 (0) | 70 / 75 (6) | | 80 / 70 (0) | 100 / 99 (0) |
| 4 | 0.56 | 44 | 8.96 | 25 / 20 (0) | 0 / 10 (100) | | 70 / 50 (0) | 100 / 90 (0) |
| 4 | 1.12 | 44 | 8.96 | 35 / 50 (30) | 25 / 40 (37) | | 80 / 50 (0) | 100 / 98 (0) |
| 4 | 2.24 | 44 | 8.96 | 85 / 70 (0) | 25 / 60 (58) | | 95 / 60 (0) | 100 / 95 (0) |
| 4 | 4.48 | 44 | 8.96 | 85 / 75 (0) | 60 / 75 (20) | | 90 / 70 (0) | 100 / 99 (0) |
| 4 | 0.56 | 45 | 8.96 | 20 / 80 (75) | 70 / 85 (17) | | 30 / 50 (40) | 99 / 98 (0) |
| 4 | 1.12 | 45 | 8.96 | 85 / 85 (0) | 90 / 90 (0) | | 60 / 60 (0) | 100 / 98 (0) |
| 4 | 2.24 | 45 | 8.96 | 90 / 95 (5) | 99 / 97 (0) | | 99 / 80 (0) | 99 / 99 (0) |
| 4 | 4.48 | 45 | 8.96 | 100 / 95 (0) | 100 / 99 (0) | | 60 / 80 (25) | 100 / 100 (0) |
| 4 | 0.56 | 52 | 8.96 | 40 / 40 (0) | 10 / 90 (88) | | 50 / 60 (16) | 90 / 90 (0) |
| 4 | 1.12 | 52 | 8.96 | 50 / 60 (16) | 40 / 99 (59) | | 80 / 60 (0) | 75 / 90 (16) |
| 4 | 2.24 | 52 | 8.96 | 90 / 75 (0) | 55 / 99 (44) | | 80 / 70 (0) | 90 / 95 (5) |
| 4 | 4.48 | 52 | 8.96 | 90 / 95 (5) | 70 / 90 (22) | | 80 / 80 (0) | 100 / 95 (0) |

| Herbicide No. | Rate | Antidote No. | Rate | Rice W/WO (Saf) | Soybean W/WO (Saf) | Corn W/WO (Saf) | Barnyard Grass W/WO (Saf) | Green Foxtail W/WO (Saf) |
|---|---|---|---|---|---|---|---|---|
| 6 | 1.12 | 6 | 0.56 | 30 / 25 (0) | | | 100 / 100 (0) | |
| 6 | 1.12 | 6 | 2.24 | 20 / 25 (20) | | | 100 / 100 (0) | |

TABLE IV -continued

% PLANT INHIBITION AND % SAFENING EFFECT ( )

| | | | | | | | | | | | | | |
|---|---|---|---|---|---|---|---|---|---|---|---|---|---|
| 6 | 1.12 | 6 | 8.96 | 10 | 25 (60) | | | | | 95 (5) | 100 | | |
| 6 | 4.48 | 6 | 0.56 | 45 | 80 (43) | | | | | 100 (0) | 100 | | |
| 6 | 4.48 | 6 | 2.24 | 45 | 80 (43) | | | | | 100 (0) | 100 | | |
| 6 | 4.48 | 6 | 8.96 | 40 | 80 (50) | | | | | 100 (0) | 100 | | |
| 10 | 0.56 | 6 | 0.56 | | | 80 (0) | 65 | | | 100 (0) | 100 | | |
| 10 | 0.56 | 6 | 2.24 | | | 10 (50) | 20 | | | 95 (5) | 100 | | |
| 10 | 0.56 | 6 | 2.24 | | | 80 (0) | 45 | | | 100 (0) | 100 | 100 (0) | 100 |
| 10 | 0.56 | 6 | 2.24 | | | 15 (76) | 65 | | | 100 (0) | 100 | | |
| 10 | 0.56 | 6 | 8.96 | | | 15 (66) | 45 | | | 50 (50) | 100 | 100 (0) | 100 |
| 10 | 0.56 | 6 | 8.96 | | | 0 (100) | 20 | | | 100 (0) | 100 | | |
| 10 | 0.56 | 6 | 8.96 | | | 0 (100) | 65 | | | 100 (0) | 100 | | |
| 10 | 2.24 | 6 | 0.56 | | | 75 (6) | 80 | | | 100 (0) | 100 | | |
| 10 | 2.24 | 6 | 2.24 | | | 45 (43) | 80 | | | 100 (0) | 100 | | |
| 10 | 2.24 | 6 | 2.24 | | | 20 (63) | 55 | | | 100 (0) | 100 | | |
| 10 | 2.24 | 6 | 2.24 | | | 90 (10) | 100 | | | 100 (0) | 100 | 100 (0) | 100 |
| 10 | 2.24 | 6 | 8.96 | | | 15 (72) | 55 | | | 100 (0) | 100 | | |
| 10 | 2.24 | 6 | 8.96 | | | 30 (70) | 100 | | | 100 (0) | 100 | 100 (0) | 100 |
| 10 | 2.24 | 6 | 8.96 | | | 5 (93) | 80 | | | 100 (0) | 100 | | |
| 10 | 0.56 | 7 | 2.24 | | | 60 (36) | 95 | | | 100 (0) | 100 | | |
| 10 | 0.56 | 7 | 8.96 | | | 25 (73) | 95 | | | 100 (0) | 100 | | |
| 10 | 2.24 | 7 | 2.24 | | | 65 (35) | 100 | | | 100 (0) | 100 | | |
| 10 | 2.24 | 7 | 8.96 | | | 35 (65) | 100 | | | 100 (0) | 100 | | |
| 10 | 0.56 | 22 | 0.56 | | | 50 (23) | 65 | | | 100 (0) | 100 | | |
| 10 | 0.56 | 22 | 2.24 | | | 65 (0) | 65 | | | 95 (5) | 100 | | |
| 10 | 0.56 | 22 | 8.96 | | | 10 (84) | 65 | | | 100 (0) | 100 | | |
| 10 | 2.24 | 22 | 0.56 | | | 85 (0) | 80 | | | 100 (0) | 100 | | |
| 10 | 2.24 | 22 | 2.24 | | | 50 (37) | 80 | | | 100 (0) | 100 | | |
| 10 | 2.24 | 22 | 8.96 | | | 50 (37) | 80 | | | 100 (0) | 100 | | |
| 10 | 2.24 | 25 | 2.24 | 40 (0) | 35 | | | | | 100 (0) | 100 | | |
| 10 | 2.24 | 25 | 8.96 | 60 (0) | 35 | | | | | 100 (0) | 100 | | |
| 10 | 4.48 | 25 | 2.24 | 65 (7) | 70 | | | | | 100 (0) | 100 | | |
| 10 | 4.48 | 25 | 8.96 | 85 (0) | 70 | | | | | 100 (0) | 100 | | |
| 10 | 2.24 | 27 | 2.24 | 55 (0) | 25 | | | | | 100 (0) | 100 | | |
| 10 | 2.24 | 27 | 8.96 | 15 (40) | 25 | | | | | 100 (0) | 100 | | |
| 10 | 4.48 | 27 | 2.24 | 50 (16) | 60 | | | | | 100 (0) | 100 | | |
| 10 | 4.48 | 27 | 8.96 | 70 (0) | 60 | | | | | 100 (0) | 100 | | |
| 10 | 0.14 | 37 | 8.96 | 40 (20) | 50 | | | | | 98 (0) | 98 | 95 (0) | 95 |
| 10 | 0.56 | 37 | 2.24 | 75 (0) | 45 | | | | | 100 (0) | 100 | 100 (0) | 100 |
| 10 | 0.56 | 37 | 8.96 | 25 (44) | 45 | | | | | 100 (0) | 100 | 100 (0) | 100 |
| 10 | 0.56 | 37 | 8.96 | 50 (37) | 80 | | | | | 98 (0) | 98 | 95 (3) | 98 |
| 10 | 1.12 | 37 | 8.96 | 65 | 90 | | | | | 100 | 99 | 98 | 98 |

TABLE IV -continued

| % PLANT INHIBITION AND % SAFENING EFFECT ( ) | | | | | | | | | | |
|---|---|---|---|---|---|---|---|---|---|---|
| 10 | 2.24 | 37 | 2.24 | 95 (27) | 100 | 100 (0) | 100 | 100 (0) | 100 |
| 10 | 2.24 | 37 | 8.96 | 90 (5) | 95 | 100 (0) | 100 | 99 (0) | 99 |
| 10 | 2.24 | 37 | 8.96 | 75 (5) | 100 | 100 (0) | 100 | 100 (0) | 100 |
| 10 | 0.56 | 44 | 2.24 | 85 (25) | 95 | 100 (0) | 100 | | |
| 10 | 0.56 | 44 | 8.96 | 20 (10) | 95 | 100 (0) | 100 | | |
| 10 | 2.24 | 44 | 2.24 | 80 (78) | 100 | 100 (0) | 100 | | |
| 10 | 2.24 | 44 | 8.96 | 70 (20)(30) | 100 | 100 (0) | 100 | | |

EXAMPLE 64

The following procedure shows interaction between a herbicide and antidote when applied together as a mixture before emergence of the crop and weed species. Containers were filled and compacted with fumigated silt loam top soil to a depth of about 1.3 cm from the top of the container. A first container was designated as an untreated control, a second container was designated as a herbicide control, and a third container was designated as a herbicide + antidote test container. Each of the containers was seeded with both crop plant and weed species. The herbicide + antidote mixture was applied to the seeded containers either by a procedure of topical application of the mixture to a soil layer placed over the seed bed followed by watering to achieve incorporation, or by a procedure of incorporation of a quantity of the mixture into soil and then placement of the treated soil into the container over the seed bed. The containers were then placed on a greenhouse bench, and sub-irrigated as required for the duration of the test. Plant response was observed about three weeks after initial treatment. Results are reported in Table V.

TABLE V

| % PLANT INHIBITION AND % SAFENING EFFECT ( ) | | | | | | | |
|---|---|---|---|---|---|---|---|
| HERBICIDE | | ANTIDOTE | | BARNYARD GRASS | | RICE | |
| No. | RATE | No. | RATE | W | WO | W | WO |
| 6 | 1.68 | 6 | 0.84 | 100 (0) | 100 | 10 (0) | 8 |
| 6 | 1.68 | 6 | 1.68 | 100 (0) | 100 | 10 (0) | 8 |
| 6 | 1.68 | 6 | 3.36 | 100 (0) | 100 | 10 (0) | 8 |
| 6 | 3.36 | 6 | 0.84 | 100 (0) | 100 | 33 (5) | 35 |
| 6 | 3.36 | 6 | 1.68 | 100 (0) | 100 | 33 (5) | 35 |
| 6 | 3.36 | 6 | 3.36 | 100 (0) | 100 | 10 (71) | 35 |
| 6 | 6.72 | 6 | 0.84 | 100 (0) | 100 | 60 (0) | 58 |
| 6 | 6.72 | 6 | 1.68 | 100 (0) | 100 | 48 (17) | 58 |
| 6 | 6.72 | 6 | 3.36 | 100 (0) | 100 | 60 (0) | 58 |

The foregoing examples illustrate that the 2-amino-4,5-substituted-oxazole/thiazone compounds of this invention are useful in reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate, and the sodium salts of alkylnaphthalenesulfonic acids, fatty alcohol sulfates such as the sodium salts of monoesters of sulfuric acid with n-aliphatic alcohols containing 8-18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, longchain alcohols usually containing 10-18 carbon atoms, and condensation products of ethylene oxide with fatty acids, alkylphenols, and mercaptans.

The following examples describe preparation of herbicide formulations, antidote formulations, and herbicide + antidote formulations, and use of these formulations, under field test conditions.

EXAMPLE 65

Antidote compound in crystalline form as prepared in Example 6 was converted to a wettable powder for use in field tests. The wettable powder contained the following ingredients:

|  | % by wt. |
|---|---|
| Antidote Cpd. #6 | 80.0 |
| Barden clay carrier; J. M. Huber Co., Havre de Grace, Md. | 20.0 |

These components were mixed together until uniformly dispersed and then further blended and ground in a hammer mill to a fine powder of particle size from about 50 microns to about 100 microns in diameter.

EXAMPLE 66

Antidote compound in crystalline form as prepared in Example 6 was converted to an 80% powder for use in field tests. The powder contained the following ingredients:

|  | % by wt. |
|---|---|
| Antidote Cpd. #6 | 80.8 |
| Kaolinite clay | 16.0 |
| Glycerine | 4.0 |

These components were mixed together until uniformly dispersed and then further blended and ground in a hammer mill to a fine powder of particle size from about 50 microns to about 100 microns in diameter.

EXAMPLE 67

An emulsifiable concentrate formulation containing antidote compound (as made in Example 6) was prepared for use in field tests. The formulation contained the following ingredients:

|  | % by wt. |
|---|---|
| Antidote Cpd. #6 (100% tech) | 23.51 |
| GAFAC RE-610 emulsifier (mixture of mono- and di- phosphate esters of ethoxylated nonyl phenol); GAF Corp., New York, N.Y. | 3.30 |
| FLOMO 6NP emulsifier (mixture of phosphate esters of ethoxylated nonyl phenol); DeSoto Chemical Co., Chicago, Ill. | 1.70 |
| T-400 solvent (mixture of C$_9$ aromatic compounds); Tenneco Chemical Co., Atlanta, Ga. | 35.75 |
| Monochlorobenzene | 35.74 |

These components were mixed together at room temperature until a uniform blend was obtained. The formulation had a specific gravity of 1.0209 observed at 25° C. calculated against water at 15.6° C., a solution point of 6.5° C., and a flash point less than 38° C. The formulation showed good bloom at concentrations in water of 114 ppm and 1000 ppm, and perfect bloom at 342 ppm. Emulsions containing 5% of the formulation were observed one hour after preparation as having a cream layer 0.5 cm in thickness at 114 ppm, at 342 ppm and at 1000 ppm water-hardness concentrations.

EXAMPLE 68

A sand-based granular formulation containing antidote compound (as made in Example 6) was prepared for use in field tests. The formulation contained the following ingredients:

|  | % by wt. |
|---|---|
| Antidote Cpd. #6 | 0.5 |
| Sand | 99.5 |

The antidote compound, dissolved in acetone, was added to the sand while the sand was tumbling in a small cement mixer. An air flow was maintained through the mixer to remove the acetone solvent during mixing. The antidote and sand were mixed together until these components were uniformly dispersed.

EXAMPLE 69

Antidote-coated crop seed was prepared by placing a measured quantity of seed in a plastic container along with a measured quantity of the 80% powder formulation containing antidote compound #6. The powder formulation was prepared by procedures of Example 66. The crop seed was previously treated with the fungicide captan (Chevron Chemical Co., San Francisco, CA.) and with the insecticide methoxychlor (e.i. du-Pont de Nemours & Co. Wilmington, Del.). The plastic container containing seed and powder formulation was shaken until all seed was thoroughly coated with the formulation. Antidote-coated crop seed was prepared having antidote at concentrations of 0.125% and 0.50% antidote weight to seed weight.

EXAMPLE 70

An emulsifiable concentrate type formulation containing acetochlor (herbicide compound #7) was prepared containing the following components:

|  | % by wt. |
|---|---|
| Acetochlor (93.5% technical) | 92.00 |
| Witco C-5438 emulsifier (blend of anionic/non-ionic emulsifiers in ethylene glycol); Witco Chemical Co., New York, N.Y. | 7.96 |
| GE AG-78 antifoaming agent (polysiloxane); General Electric Co., Waterford, N.Y. | 0.02 |
| Methyl violet dye; Dye Specialities Co., Jersey City, N.J. | 0.017 |

These components were mixed together at room temperature until a uniform blend was obtained. The formulation had a specific gravity of 1.1167 observed at 20° C. and calculated against water at 15.6° C., and had a flash point above 100° C. (tag closed-cup method). The formulation showed perfect emulsion bloom at water hardness concentrations of 114 ppm, 342 ppm and 1000 ppm. The emulsions were observed as 100 percent stable after one hour at each water hardness concentration. The formulation was blue and contained 86.02% by weight of acetochlor.

EXAMPLE 71

AN emulsifiable concentrate formulation containing the herbicide 2-chloro-2'-methyl-6'-methoxy-N-(isopropoxymethyl)acetanilide (herbicide compound #10) was prepared containing the following components:

|  | % by wt. |
|---|---|
| 2-chloro-2'-methyl-6'-methoxy-N-(isopropoxymethyl)acetanilide (78% Tech.) | 41.16 |
| FLOMO 50H emulsifier (50% solution of calcium dodecylbenzene sulfonate in mineral spirits); De Soto Chemical Co., Chicago, Ill. | 1.79 |
| FLOMO 14D emulsifier (reaction product of dodecyl phenol and 14 mols ethylene oxide); De Soto Chemical Co., Chicago, Ill. | 1.91 |
| FLOMO XH emulsifier (block copolymer of propylene oxide and ethylene oxide); De Soto Chemical Co., Chicago, Ill. | 0.93 |
| FLOMO 54C emulsifier (caster oil ethoxylated with 54 moles ethylene oxide); De Soto Chemical Co., Chicago, Ill. | 0.17 |
| Naphtha Solvent | 0.20 |
| Monochlorobenzene Solvent | 53.84 |

These components were mixed together at room temperature until a uniform blend was obtained. The formulation had a specific gravity of 1.1213 observed at 25° C. and calculated against water at 15.6° C., a solution point at 2° C., and a flash point less than 38° C. The formulation showed perfect emulsion bloom at water hardness concentrations of 114 ppm and 342 ppm, and very good bloom at 1000 ppm. The emulsions were observed as 100 percent stable after one hour at each test concentration. The liquid formulation was white in color and contained 32.1% by weight of herbicide compound #10.

EXAMPLE 72

Commercially-available formulations of two herbicides were used in the field tests. An atrazine (herbicide cpd. #2) formulation (Farmland Chemicals, Kansas City, Mo.) contained 43% by wt. active thiazines (480g/l or 4 lbs/gal) and 57% by wt. inert ingredients. An alachlor (herbicide cpd. #4) formulation in emulsifiable-concentrate form (LASSO ® herbicide, Monsanto Co., St. Louis, Mo.) contained 45.1% by wt. alachlor (480 g/l; 4 lb/gal) and 54.9% by wt. inert ingredients.

Other, non-commercially available herbicide formulations used in the field tests were prepared in emulsifiable-concentrate form in accordance with procedures such as described in Examples 70 and 71 for preparation of formulations of herbicide cpds. #7 and #10, respectively. These herbicides and their concentrations of active ingredient were as follows:

| Herbicide Cpd. # | Concentration of Active Ingredient |
|---|---|
| 3 | 480 g/l; 4 lb/gal |
| 9 | 720 g/l; 6 lb/gal |
| 12 | 480 g/l; 4 lb/gal |
| 14 | 600 g/l; 5 lb/gal |
| 15 | 480 g/l; 4 lb/gal |
| 16 | 360 g/l; 3 lb/gal |
| 19 | 480 g/l; 4 lb/gal |
| 20 | 600 g/l; 5 lb/gal |
| 21 | 600 g/l; 5 lb/gal |
| 22 | 600 g/l; 5 lb/gal |

EXAMPLE 73

Formulations were prepared for field testing to determine the comparative effects of herbicide alone, herbicide-and-antidote in combination, and antidote alone. The herbicide and/or antidote formulations were applied by tank-mix spraying. Also, the antidote was evaluated as a seed coating and as an in-furrow granule. For each formulation, a tractormounted 20-liter spray tank was filled about half-full with water. For the herbicide formulations containing no antidote, an appropriate amount of emulsifiable concentrate (as prepared in Examples 70-72) wa added directly to a tank. For the antidote-containing tank-mix formulations, the antidote in wettable powder form (as prepared in Example 65) or in emulsifiable form (as prepared in Example 67) was added to a tank. Then for the herbicide + antidote formulation, antidote emulsifiable concentrate was added to a tank containing herbicide. Each tank-mix formulation was agitated sufficiently to ensure a uniform suspension. The relative amounts of water, herbicide emulsifiable concentrate, or antidote, added to the tank were calculated for each formulation based upon a formulation spraying rate of 281 l/ha (30 gal/acre) in order to achieve various field application rates of herbicide and antidote, as appropriate, for the rates shown in Tables VI-XIV. Each formulation was sprayed on three replicate plots, with a small-plot tractormounted sprayer with a 3 meter (10 ft) boom delivering 281 l/ha (30 gal/ac) at 2 atm pressure (30 psi), unless otherwise specified. The treatments were made to Ray silt loam topsoil containing approximately one percent organic matter and were selected in a random manner in order to normalize variations in plot soil conditions. Three control plots were established which were not treated with herbicide or with antidote formulations. Where appropriate, crop seed used in the field tests was treated prior to planting with the fungicide captan and the insecticide methoxychlor.

EXAMPLE 74

Formulations of alachlor (herbicide cpd. #4), atrazine + alachlor (herbicide cpds #2 + #4), and atrazine (herbicide cpd. #2), were surface-applied pre-emergent to side-by-side field plots to determine their relative inhibition of grassy and broadleaf weeds and their relative injury to grain sorghum grown from seed treated with antidote compound #6. DeKalb E59+ hybrid grain sorghum seed, treated with antidote #6 in an 80% powder formulation (prepared as described in Examples 66 and 69) was planted into four rows to a depth of 2.5 cm (1 in) in Ray silt loam soil using a John Deere 71 Flexiplanter at a seeding rate of at least 22 Kg/ha (20 lb/ac). The herbicide test and control formulations were prepared and surface-applied to the field plots (3×6 m; 10×20 ft) as described in Example 73. Test observations, taken by three observers, are reported in Table VI.

Field Conditions at Treatment:
Wind speed: 10-13 Km/hr (6-8 mph)
Air temperature: 24° C. (75° F.)
Soil temperature: 20° C. (68° F.)
Relative humidity: 74%
Soil moisture: surface dry, subsurface moist.
Climatic Conditions First-Three Weeks:
Average air temp.: Hi/Lo 29° C. (84° F.) / 18° C. (64° F.)
Extreme air temp.: Hi/Lo 34° C. (93° F.) / 11° C. (52° F.)
Rainfall: ~2.5 cm (i in.) 11 days after treatment total 3.51 cm (1.38 in)
Irrigation: None

TABLE VI

| Formulation* | | Crop & Weed Inhibition (%) | | | |
|---|---|---|---|---|---|
| Herbicide | Antidote | Grain Sorghum | Giant Foxtail | Lambs-quarter | Common Purslane |
| #2 | & #4 | #6 | a/b | a/b | a/b | a/b |
| 0 | 0 | 0 | 0/0 | 0/0 | 0/0 | 0/0 |
| 0 | 2.24 | 0 | 97/88 | 99/100 | 100/100 | 100/100 |
| 0 | 4.48 | 0 | 97/93 | 100/100 | 100/100 | 100/100 |
| 1.4 | 2.24 | 0 | 94/78 | 100/100 | 100/100 | 100/100 |
| 1.4 | 0 | 0 | 18/15 | 100/100 | 100/100 | 100/100 |
| 0 | 0 | 0.125 | 2/3 | 0/0 | 0/0 | 0/0 |
| 0 | 2.24 | 0.125 | 7/3 | 100/100 | 100/100 | 100/100 |
| 0 | 4.48 | 0.125 | 14/12 | 100/100 | 100/100 | 100/100 |
| 1.4 | 2.24 | 0.125 | 18/8 | 100/100 | 100/100 | 100/100 |
| 0 | 0 | 0.50 | 5/7 | 0/0 | 0/0 | 0/0 |
| 0 | 2.24 | 0.50 | 3/5 | 100/100 | 100/100 | 100/100 |
| 0 | 4.48 | 0.50 | 19/17 | 100/100 | 100/100 | 100/100 |
| 1.4 | 2.24 | 0.50 | 12/8 | 100/100 | 100/100 | 100/100 |

*Herbicide active ingredient in Kg/ha; antidote rate in % concentration (weight of antidote compound per unit weight of seed).
a = Observations taken at 19 days after treatment.
b = Observations taken at 39 days after treatment.

EXAMPLE 75

Formulations of alachlor (herbicide cpd. #4), atrazine+alachlor (herbicide cpds. #2 + #4), and atrazine (herbicide cpd. #2), were applied pre-emergent to side-by-side field plots to determine their relative inhibition of broadleaf weeds and their relative injury to grain sorghum grown from seed treated with antidote compound #6. DeKalb E59+ hybrid grain sorghum seed, treated with antidote #6 in an 80% powder formulation (prepared as described in Examples 66 and 69) was planted into four rows to a depth of 2.5 cm (1 in) in Ray silt loam soil using a John Deere 71 Flexiplanter at a seeding rate of at least 22 Kg/ha (20 lb/ac). The herbicide test and control formulations were prepared and surface-applied to the field plots (3×6 m; 10×20 ft) as described in Example 73. Test observations, taken by one observer, are reported in Table VII.

Field Conditions at Treatment:
Wind speed: 8-16 Km/hr (5-10 mph)
Air temp.: 30° C. (86° F.)
Soil temp.: 26° C. (78° F.)
Relative humidity: 50%
Soil moisture: Fine, moist seed bed
Climatic Conditions First-Three Weeks:
Average air temp.: Hi/Lo 35° C. (95° F.) / 23° C. (73° F.)
Extreme air temp.: Hi/Lo 41° C. (105° F.) / 13° C. (56° F.)
Rainfall: 2.5 cm (1 in) 5 days after treatment; 10.9 cm (4.35 in) total.
Irrigation: None

TABLE VII

| Formulation* | | | Crop/Weed Inhibition (%)** | | |
|---|---|---|---|---|---|
| Herbicide | | Antidote | Grain Sorghum | Carpet Weed | Morning-glory |
| #2 | & #4 | #6 | | | |
| 0 | 0 | 0 | 0 | 0 | 0 |
| 0 | 2.24 | 0 | 28 | 100 | 3 |
| 0 | 4.48 | 0 | 48 | 100 | 18 |
| 1.4 | 2.24 | 0 | 25 | 100 | 98 |
| 1.4 | 0 | 0 | 22 | 100 | 97 |
| 0 | 0 | 0.125 | 3 | 0 | 0 |
| 0 | 2.24 | 0.125 | 13 | 100 | 0 |
| 0 | 4.48 | 0.125 | 18 | 100 | 10 |
| 1.4 | 2.24 | 0.125 | 25 | 100 | 94 |
| 0 | 0 | 0.50 | 7 | 0 | 0 |
| 0 | 2.24 | 0.50 | 18 | 100 | 0 |
| 0 | 4.48 | 0.50 | 23 | 100 | 17 |
| 1.4 | 2.24 | 0.50 | 13 | 100 | 99 |

*Herbicide rate in Kg/ha; antidote rate in % concentration (weight of antidote compound per unit weight of seed).
**Observations taken at 35 days after treatment.

EXAMPLE 76

Formulations of alachlor (herbicide cpd. #4) atrazine+alachlor (herbicide cpds. #2 + #4), and atrazine (herbicide cpd. #2), were applied pre-emergent to side-by-side field plots to determine their relative inhibition of grassy and broadleaf weeds and their relative injury to grain sorghum grown from seed in furrows treated with antidote-containing granules. DeKalb E59+ hybrid grain sorghum seed was planted into four furrows spaced 76 cm (30 in) apart to a depth of 2.5 cm (1 in) in Ray silt loam soil using a John Deere 71 Flexiplanter at a seeding rate of 9-14 Kg/ha (8-12 lb/ac). Sand granules containing antidote #6 at ½% w/w concentration (prepared as described in Example 68) were applied directly into the open furrows immediately behind the seed disc openers through plastic tubes leading from granular insecticide boxes mounted on the Flexiplanter. The herbicide test and control formulations were prepared and surface-applied to the field plots (3×6 m; 10×20 ft) as described in Example 73. Test observations, taken by two observers, are reported in Table VIII.

Field Conditions at Treatment:
Wind speed: 2-5 Km/hr (1-3 mph)
Air temperature: 26° C. (78° F.)
Soil temperature: 22° C. (72° F.)
Relative humidity: 58%
Soil moisture: surface moist, subsurface very moist
Climatic Conditions First-Three Weeks:
Average air temp.: Hi/Lo 29° C. (84° F.) / 18° C. (64° F.)
Extreme air temp.: Hi/Lo 34° C. (93° F.) / 11° C. (52° F.)
Rainfall: 1.1 cm (0.45 in.) 3 days after treatment; 2.94 cm (1.16 in) total
Irrigation: None

TABLE VIII

| Formulation* | | Crop & Weed Inhibition (%) | | | |
|---|---|---|---|---|---|
| Herbicide #2 & #4 | Antidote #6 | Grain Sorghum a/b | Giant Foxtail a/b | Common Purslane a/b | Pigweed a/b |
| 0 | 0 | 0/0 | 0/0 | 0/0 | 0/0 |
| 0 | 2.24 | 36/20 | 99/96 | 79/78 | 100/100 |
| 0 | 4.48 | 58/36 | 100/100 | 98/97 | 100/100 |
| 1.4 | 2.24 | 24/23 | 100/100 | 100/100 | 100/100 |
| 1.4 | 0 | 11/6 | 91/96 | 100/100 | 100/100 |
| 0 | 0 | 0.14 | 16/0 | 0/0 | 0/0 | 0/0 |
| 0 | 2.24 | 0.14 | 18/7 | 99/99 | 80/72 | 100/100 |
| 0 | 4.48 | 0.14 | 22/15 | 100/100 | 94/98 | 100/100 |
| 1.4 | 2.24 | 0.14 | 18/12 | 100/100 | 100/100 | 100/100 |
| 0 | 0 | 0.56 | 7/0 | 0/0 | 0/0 | 0/0 |
| 0 | 2.24 | 0.56 | 5/9 | 99/98 | 70/85 | 100/100 |
| 0 | 4.48 | 0.56 | 12/17 | 100/99 | 91/94 | 100/100 |
| 1.4 | 2.24 | 0.56 | 13/11 | 100/100 | 100/100 | 100/100 |

*Herbicide and antidote rates in Kg/ha.
a = Observations taken at 23 days after treatment.
b = Observations taken at 42 days after treatment.

EXAMPLE 77

Formulations of alachlor (herbicide cpd. #4) and tank-mix safened alachlor (with antidote cpd. #6) were pre-emergent surface-applied in side-by-side field plots to determine their relative inhibition of grassy and broadleaf weeds in the presence of corn in eastern Missouri. Four rows of DeKalb E59+ grain sorghum seed, four rows of green foxtail seed, and four rows of barnyardgrass seed were planted 2-4 cm (¾-1½ in) deep in Ray silt loam topsoil using a Planet Jr. planter at a seeding rate of at least 22 Kg/ha (20 lb/ac). Test formulations of alachlor, safened alachlor and a control formulation of antidote without herbicide, were prepared as described in Example 73. The plots (2×5 m; 7×15 ft) were sprayed with a $CO_2$-pressurized small-plot backpack sprayer at a rate of 281 l/ha (30 gal/ac). Test observations, taken by one observer, are reported in Table IX.
Field Conditions at Treatment:
Wind speed: 8-16 Km/hr (5-10 mph)
Air temperature: 29° C. (85° F.)
Soil temperature: 25.5° C. (78° F.)
Relative humidity: 50%
Soil moisture: surface moist, subsurface very moist
Climatic Conditions First-Three Weeks:
Average air temp.: Hi/Lo 28° C. (83° F.) / 17° C. (63° F.)
Extreme air temp.: Hi/Lo 34° C. (93° F.) / 11° C. (52° F.)
Rainfall: 0.5 cm (0.2 in.) 2 days after treatment; 3.12 cm (1.23 in) total
Irrigation: None

TABLE IX

| Formulation* | | Crop & Weed Inhibition (%) | | | |
|---|---|---|---|---|---|
| Herbicide #4 | Antidote #6 | Grain Sorghum a/b | Barnyard- Grass a/b | Giant Foxtail a/b | Pigweed a/b |
| 0 | 0 | 0/0 | 0/0 | 0/0 | 0/0 |
| 2.24 | 0 | 38/13 | 97/87 | 97/85 | 99/97 |
| 4.48 | 0 | 62/30 | 98/92 | 99/90 | 100/100 |
| 0 | 2.24 | 13/0 | 13/0 | 13/0 | 0/0 |
| 2.24 | 2.24 | 10/0 | 98/85 | 97/80 | 100/90 |
| 4.48 | 2.24 | 42/27 | 99/95 | 98/87 | 100/100 |
| 0 | 4.48 | 12/0 | 13/0 | 10/0 | 0/0 |
| 2.24 | 4.48 | 15/0 | 98/93 | 98/93 | 100/100 |
| 4.48 | 4.48 | 18/5 | 99/95 | 99/95 | 100/98 |

*Herbicide + antidote tank-mix; rates in Kg/ha
a = Observations taken at 22 days after treatment.
b = Observations taken at 42 days after treatment.

EXAMPLE 78

Formulations of 11 acetanilide herbicides (cpds. #3, #4, #7, #9, #10, #12, #14, #15, #16, #19 and #20) were individually surface-applied pre-emergent to side-by-side field plots to determine their relative inhibition of narrow and broadleaf weeds and their relative injury to grain sorghum grown from seed treated with antidote compound #6. DeKalb E59+ hybrid grain sorghum seed, treated with antidote #6 in an 80% powder formulation (prepared as described in Examples 66 and 69) was planted into 16 rows in Ray silt loam soil to a depth of 2.5 cm (1 in) using a John Deere 71 Flexi-planter at a seeding rate of 9-14 Kg/ha (8-12 lb/ac). The herbicide test and control formulations were prepared and surface-applied to the field plots (3×12 m; 10×40 ft) as described in Example 73. Test observations, taken by one observer, are reported in Table X.
Field Conditions at Treatment:
Wind speed: 5-10 Km/hr (3-6 mph)
Air temperature: 28° C. (82° F.)
Soil temperature: 27° C. (80° F.)
Relative humidity: >50%
Soil moisture: surface dry, subsurface moist
Climatic Conditions First-Three Weeks:
Average air temp.: Hi/Lo 28° C. (83° F.) / 17° C. (62° F.)
Extreme air temp.: Hi/Lo 34° C. (93° F.) / 11° C. (52° F.)
Rainfall: 0.7 cm (0.29 in.) one day after treatment; 4.1 cm (1.60 in) total
Irrigation: None

TABLE X

| | | Sorghum Inhibition (%) | | Weed Inhibition (%) | |
|---|---|---|---|---|---|
| Herbicide | | No Antidote | Antidote #6 ½% on Seed | Giant Foxtail | Pigweed |
| # | Kg/ha | a/b | a/b | a/b | a/b |
| 0 | 0 | 0/0 | 3/0 | 0/0 | 0/0 |
| #3 | 1.12 | 5/0 | 10/3 | 97/100 | 96/90 |
| | 2.24 | 22/18 | 15/3 | 98/100 | 97/94 |
| | 4.48 | 58/57 | 53/43 | 99/100 | 97/93 |
| #4 | 1.12 | 10/0 | 7/0 | 99/99 | 99/95 |
| | 2.24 | 20/0 | 7/0 | 100/100 | 100/100 |
| | 4.48 | 23/3 | 15/0 | 99/100 | 99/100 |
| #7 | 1.12 | 23/17 | 12/0 | 99/100 | 100/100 |
| | 2.24 | 25/27 | 17/10 | 99/100 | 99/100 |
| | 4.48 | 30/13 | 27/8 | 100/100 | 100/100 |
| #9 | 1.12 | 23/13 | 18/3 | 99/100 | 98/96 |
| | 2.24 | 17/7 | 13/0 | 99/100 | 98/96 |
| | 4.48 | 35/20 | 23/0 | 99/100 | 99/99 |
| #10 | 1.12 | 12/32 | 12/10 | 100/100 | 98/97 |
| | 2.23 | 30/30 | 28/15 | 99/100 | 100/100 |
| | 4.48 | 78/68 | 68/58 | 100/100 | 100/100 |
| #12 | 1.12 | 17/3 | 20/3 | 99/100 | 98/99 |

TABLE X-continued

| Herbicide | | Sorghum Inhibition (%) | | Weed Inhibition (%) | |
|---|---|---|---|---|---|
| | | No Antidote | Antidote #6 ⅛% on Seed | Giant Foxtail | Pigweed |
| # | Kg/ha | a/b | a/b | a/b | a/b |
| | 2.24 | 18/5 | 12/0 | 99/100 | 99/99 |
| | 4.48 | 57/40 | 32/13 | 100/100 | 99/99 |
| #14 | 1.12 | 12/7 | 10/0 | 98/100 | 96/95 |
| | 2.24 | 10/0 | 18/0 | 99/100 | 95/99 |
| | 4.48 | 17/7 | 15/0 | 98/100 | 99/100 |
| #15 | 1.12 | 27/7 | 23/3 | 97/100 | 97/93 |
| | 2.24 | 30/12 | 12/0 | 99/100 | 98/98 |
| | 4.48 | 58/52 | 43/38 | 99/99 | 99/99 |
| #16 | 1.12 | 13/0 | 17/0 | 98/100 | 96/94 |
| | 2.24 | 30/12 | 20/3 | 99/100 | 98/97 |
| | 4.48 | 27/10 | 23/5 | 99/100 | 99/100 |
| #19 | 1.12 | 8/3 | 8/0 | 98/100 | 98/97 |
| | 2.24 | 18/3 | 8/0 | 98/100 | 96/98 |
| | 4.48 | 33/5 | 23/3 | 99/100 | 99/99 |
| #20 | 1.12 | 18/17 | 15/7 | 98/100 | 98/92 |
| | 2.24 | 30/12 | 25/0 | 99/100 | 98/96 |
| | 4.48 | 60/43 | 60/37 | 99/99 | 99/99 | a = Observations taken at 21 days after treatment.
b = Observations taken at 44 days after treatment.

EXAMPLE 79

Formulations of nine acetanilide herbicides (cpds. #3, #7, #10, #14, #15, #16, #19, #21 and #22) were individually surface-applied pre-emergent to side-by-side field plots to determine their relative inhibition of narrow and broadleaf weeds and their relative injury to corn grown from seed treated with antidote compound #6. Pioneer 3369A hybrid field corn seed, treated with antidote #6 in an 80% powder formulation (prepared as described in Examples 66 and 69) was planted into 16 rows to a depth of 2.5 cm (1 in) in Ray silt loam soil using a John Deere 71 Flexiplanter at a seeding rate of at least 9–14 Kg/ha (8–12 lb/ac). The herbicide test and control formulations were prepared and surface-applied to the field plots (3×12 m; 10×40 ft) as described in Example 73. Test observations, taken by one observer, are reported in Table XI.

Field Conditions at Treatment:
Wind speed: 10–13 Km/hr (6–8 mph)
Air temperature: 32° C. (90° F.)
Soil temperature: 29° C. (85° F.)
Relative humidity: >50%
Soil moisture: surface dry, subsurface moist
Climatic Conditions First-Three Weeks:
Average air temp.: Hi/Lo 29° C. (84° F.) / 18° C. (64° F.)
Extreme air temp.: Hi/Lo 34° C. (93° F.) / 11° C. (52° F.)
Rainfall: 1.1 cm (0.45 in.) two days after treatment; 2.94 cm (1.16 in) total
Irrigation: None

TABLE XI

| Herbicide | | Sorghum Inhibition (%) | | Weed Inhibition (%) | | |
|---|---|---|---|---|---|---|
| | | No Antidote | Antidote #6 ⅛% on Seed | Giant Foxtail | Common Purslane | Pigweed |
| # | Kg/ha | a/b | a/b | a/b | a | a/b |
| 0 | 0 | 0/0 | 5/7 | 0/0 | 0 | 0/0 |
| #3 | 1.12 | 37/25 | 38/25 | 96/98 | 98 | 99/98 |
| | 2.24 | 65/43 | 50/33 | 99/100 | 100 | 100/100 |
| | 4.48 | 78/70 | 73/47 | 100/100 | 100 | 100/100 |
| #7 | 1.12 | 30/40 | 28/33 | 98/99 | 100 | 99/100 |
| | 2.24 | 33/43 | 37/28 | 100/100 | 100 | 100/100 |
| | 4.48 | 60/50 | 45/37 | 100/100 | 100 | 100/100 |

TABLE XI-continued

| Herbicide | | Sorghum Inhibition (%) | | Weed Inhibition (%) | | |
|---|---|---|---|---|---|---|
| | | No Antidote | Antidote #6 ⅛% on Seed | Giant Foxtail | Common Purslane | Pigweed |
| # | Kg/ha | a/b | a/b | a/b | a | a/b |
| #10 | 1.12 | 38/37 | 35/18 | 100/100 | 100 | 100/100 |
| | 2.24 | 68/65 | 47/47 | 100/100 | 100 | 100/100 |
| | 4.48 | 68/67 | 47/50 | 100/100 | 100 | 100/100 |
| #14 | 1.12 | 17/20 | 20/25 | 99/97 | 100 | 97/95 |
| | 2.24 | 22/42 | 23/40 | 95/99 | 100 | 96/99 |
| | 4.48 | 65/53 | 65/48 | 100/99 | 100 | 100/99 |
| #15 | 1.12 | 20/32 | 38/43 | 99/99 | 100 | 99/99 |
| | 2.24 | 18/28 | 28/32 | 99/97 | 100 | 100/97 |
| | 4.48 | 37/47 | 35/47 | 100/99 | 100 | 100/100 |
| #16 | 1.12 | 23/22 | 25/32 | 98/98 | 100 | 99/99 |
| | 2.24 | 45/30 | 40/33 | 99/97 | 100 | 100/97 |
| | 4.48 | 35/35 | 30/42 | 100/100 | 100 | 100/100 |
| #19 | 1.12 | 15/17 | 18/20 | 98/99 | 100 | 98/99 |
| | 2.24 | 27/28 | 27/27 | 96/98 | 98 | 96/98 |
| | 4.48 | 53/45 | 48/57 | 100/100 | 100 | 100/100 |
| #21 | 1.12 | 10/28 | 28/30 | 96/99 | 99 | 100/99 |
| | 2.24 | 43/47 | 48/43 | 99/100 | 100 | 98/100 |
| | 4.48 | 58/40 | 52/40 | 99/99 | 100 | 99/99 |
| #22 | 1.12 | 15/30 | 35/27 | 98/99 | 100 | 100/99 |
| | 2.24 | 45/35 | 57/47 | 99/99 | 100 | 100/100 |
| | 4.48 | 53/43 | 53/40 | 100/100 | 100 | 100/100 | a = Observations taken at 26 days after treatment.
b = Observations taken at 42 days after treatment.

EXAMPLE 80

Formulations of 11 acetanilide herbicides (cpds. #3, #4, #7, #9, #10, #12, #13, #14, #15, #16, #19 and #20) were individually surface-applied pre-emergent to side-by-side field plots to determine their relative inhibition of Giant Foxtail and grain sorghum grown from seed in furrows treated with antidote-containing granules. DeKalb E59+ hybrid grain sorghum seed was planted into twelve furrows spaced 76 cm (30 in) apart to a depth of 2.5 cm (1 in) using a John Deere 71 Flexiplanter at a seeding rate of 9–14 Kg/ha (8–12 lb/ac). Sand granules containing antidote #6 at ½% w/w concentration (prepared as described in Example 68) were applied directly into the open furrow immediately behind the seed disc openers through plastic tubes leading from granular insecticide boxes mounted on the Flexiplanter. The herbicide test and control formulations were prepared and surface-applied to the field plots (3×9 m; 10×30 ft) as described in Example 73. Test observations, taken by two observers, are reported in Table XII.

Field Conditions at Treatment:
Wind speed: 3–8 Km/hr (2–5 mph)
Air temperature: 30° C. (86° F.)
Soil temperature: 26° C. (79° F.)
Relative humidity: >50%
Soil moisture: surface moist, subsurface very moist
Climatic Conditions First-Three Weeks:
Average air temp.: Hi/Lo 29° C. (84° F.) / 17° C. (63° F.)
Extreme air temp.: Hi/Lo 35° C. (95° F.) / 11° C. (52° F.)
Rainfall: 0.1 cm (0.05 in.) one day after treatment; 3.33 cm (1.31 in) total
Irrigation: None

TABLE XII

| Herbicide # | Kg/ha | Sorghum Inhibition (%)* No Antidote | Sorghum Inhibition (%)* Antidote #6 0.14 Kg/ha | Weed Inhibition (%)* Giant Foxtail |
|---|---|---|---|---|
| 0 | 0 | 0 | 15 | 0 |
| #3 | 1.12 | 12 | 37 | 98 |
|  | 2.24 | 22 | 40 | 98 |
|  | 4.48 | 23 | 30 | 100 |
| #4 | 1.12 | 15 | 12 | 100 |
|  | 2.24 | 22 | 7 | 99 |
|  | 4.48 | 25 | 35 | 100 |
| #7 | 1.12 | 17 | 20 | 100 |
|  | 2.24 | 38 | 23 | 100 |
|  | 4.48 | 65 | 55 | 100 |
| #9 | 1.12 | 22 | 25 | 100 |
|  | 2.24 | 15 | 13 | 99 |
|  | 4.48 | 37 | 27 | 100 |
| #10 | 1.12 | 43 | 32 | 99 |
|  | 2.24 | 63 | 45 | 100 |
|  | 4.48 | 52 | 43 | 100 |
| #12 | 1.12 | 17 | 30 | 98 |
|  | 2.24 | 25 | 25 | 99 |
|  | 4.48 | 58 | 40 | 100 |
| #14 | 1.12 | 22 | 22 | 100 |
|  | 2.24 | 48 | 37 | 100 |
|  | 4.48 | 58 | 48 | 100 |
| #15 | 1.12 | 20 | 12 | 100 |
|  | 2.24 | 47 | 25 | 100 |
|  | 4.48 | 53 | 45 | 100 |
| #16 | 1.12 | 30 | 28 | 99 |
|  | 2.24 | 45 | 38 | 100 |
|  | 4.48 | 58 | 47 | 100 |
| #19 | 1.12 | 47 | 48 | 98 |
|  | 2.24 | 38 | 28 | 100 |
|  | 4.48 | 52 | 37 | 100 |
| #20 | 1.12 | 20 | 22 | 98 |
|  | 2.24 | 45 | 40 | 100 |
|  | 4.48 | 52 | 52 | 100 |

*Observations taken at 22 days after treatment; no observations were recorded at six-week period because of plot overgrowth with velvetleaf.

EXAMPLE 81

Formulations of nine acetanilide herbicides (cpds. #3, #7, #10, #14, #15, #16, #19, #21 and #22) were individually surface-applied pre-emergent to side-by-side field plots to determine their relative inhibition of grassy and broadleaf weeds and relative injury to corn grown from seed in furrows treated with antidote-containing granules. Pioneer 3369A hybrid field corn seed was planted into 16 furrows spaced 76 cm (30 in) apart to a depth of 2.5 cm (1 in) using a John Deere 71 Flexi-planter at a seeding rate of 9-14 Kg/ha (8-12 lb/ac). Sand granules containing antidote #6 at ½% w/w concentration (prepared as described in Example 68) were applied directly into the open furrow immediately behind the seed disc openers through plastic tubes leading from granular insecticide boxes mounted on the Flexi-planter. The herbicide test and control formulations were prepared and surface-applied to the field plots (3×12 m; 10×40 ft) as described in Example 73. Test observations, taken by two observers, are reported in Table XIII.

Field Conditions at Treatment:
Wind speed: 5-10 Km/hr (3-6 mph)
Air temperature: 28° C. (82° F.)
Soil temperature: 23° C. (74° F.)
Relative humidity: 55%
Soil moisture: surface dry, subsurface moist
  Climatic Conditions First-Three Weeks:
Average air temp.: Hi/Lo 29° C. (84° F.) / 18° C. (64° F.)
Extreme air temp.: Hi/Lo 34° C. (93° F.) / 11° C. (52° F.)
Rainfall: 0.80 cm (0.35 in.) one day after treatment; 3.12 cm (1.23 in) total
Irrigation: None

TABLE XIII

| Herbicide # | Kg/ha | Corn Inhibition (%) No Antidote a/b | Corn Inhibition (%) Antidote #6 0.14 Kg/ha a/b | Weed Inhibition (%) Giant Foxtail a/b | Weed Inhibition (%) Common Purslane a | Weed Inhibition (%) Pigweed a/b |
|---|---|---|---|---|---|---|
| 0 | 0 | 0 | 43/30 | 0/0 | 0 | 0/0 |
| #3 | 1.12 | 15/28 | 35/52 | 99/99 | 100 | 100/99 |
|  | 2.24 | 52/37 | 60/57 | 99/98 | 99 | 99/100 |
|  | 4.48 | 53/55 | 64/75 | 100/100 | 100 | 100/100 |
| #7 | 1.12 | 23/23 | 47/45 | 100/99 | 100 | 100/100 |
|  | 2.24 | 13/10 | 47/57 | 100/100 | 100 | 100/100 |
|  | 4.48 | 23/25 | 58/55 | 100/100 | 100 | 100/100 |
| #10 | 1.12 | 23/45 | 37/48 | 100/100 | 100 | 100/100 |
|  | 2.24 | 30/53 | 56/78 | 100/99 | 100 | 100/100 |
|  | 4.48 | 45/55 | 62/78 | 100/100 | 100 | 100/100 |
| #14 | 1.12 | 13/30 | 32/58 | 98/97 | 99 | 98/97 |
|  | 2.24 | 33/42 | 53/62 | 98/98 | 99 | 99/98 |
|  | 4.48 | 27/30 | 45/53 | 99/99 | 100 | 100/100 |
| #15 | 1.12 | 17/27 | 55/63 | 98/99 | 99 | 99/99 |
|  | 2.24 | 22/27 | 52/60 | 100/99 | 100 | 100/100 |
|  | 4.48 | 63/73 | 70/78 | 99/99 | 100 | 100/100 |
| #16 | 1.12 | 22/23 | 33/47 | 99/99 | 99 | 99/99 |
|  | 2.24 | 27/35 | 43/52 | 99/98 | 100 | 100/100 |
|  | 4.48 | 43/55 | 72/68 | 100/88 | 100 | 100/100 |
| #19 | 1.12 | 30/48 | 62/58 | 98/89 | 99 | 99/100 |
|  | 2.24 | 18/13 | 47/50 | 98/99 | 98 | 100/100 |
|  | 4.48 | 35/33 | 62/57 | 99/99 | 100 | 100/99 |
| #21 | 1.12 | 30/27 | 62/55 | 97/99 | 99 | 99/100 |
|  | 2.24 | 22/28 | 50/45 | 100/99 | 100 | 100/99 |
|  | 4.48 | 50/57 | 57/63 | 100/99 | 99 | 100/100 |
| #22 | 1.12 | 7/17 | 38/58 | 99/98 | 99 | 99/98 |
|  | 2.24 | 22/23 | 67/67 | 100/100 | 100 | 100/100 |
|  | 4.48 | 25.28 | 47/68 | 99/98 | 100 | 100/100 | a = Observations taken at 25 days after treatment.
b = Observations taken at 41 days after treatment.

EXAMPLE 82

Formulations of four herbicides (cpds. #4, #10, #12, and #16) tank-mix safened with antidote compound #6 were surface-applied pre-emergent to side-by-side field plots to determine their relative inhibition of five different crops. Two rows were planted of each of the following crop seed: Corn - Pioneer 3369A; Sorghum - DeKalb E59+; Wheat - Arthur 71; Rice - Brazos; Soybeans - Williams. The seed was planted to a depth of 2 to 2.5 cm (¾ to 1 in) in Ray silt loam soil using a Planet Jr. planter at a seeding rate of at least 22 Kg/ha (20 lb/cc). Test formulations of the herbicides and the tank-mix safened-herbicides, and a control formulation of antidote without herbicide, were prepared and sprayed on field plots (3×5 m; 10×15 ft) as described in Example 73. Test observations, taken by two observers, are reported in Table XIV.

Field Conditions at Treatment:
Wind speed: 3-6 Km/hr (2-4 mph)
Air temperature: 29° C. (85° F.)
Soil temperature: 29° C. (84° F.)
Relative humidity: >50%
Soil moisture: surface dry, subsurface slightly moist
  Climatic Conditions First-Three Weeks:
Average air temp.: Hi/Lo 33° C. (92° F.) / 722° C. (72° F.)
Extreme air temp.: Hi/Lo 41° C. (105° F.) / 16° C. (61° F.)
Rainfall: 1.3 cm (0.5 in.) one day after treatment; 11.0 cm (4.35 in) total
Irrigation: 1.3 cm (0.50 in)

TABLE XIV

| Tank-Mix Formulation | | Crop Inhibition (%) | | | | |
|---|---|---|---|---|---|---|
| Herbicide # | Antidote #6 Rate | Rice a* | Wheat a* | Soybean a/b | Sorghum a/b | Corn a/b |
| 0 | 0 | 0 | 0 | 0/0 | 0/0 | 0/0 |
| 0 | 2.24 | 0 | 0 | 0/0 | 0/0 | 0/0 |
| #4 2.24 | 0 | 91 | 75 | 22/0 | 65/43 | 7/7 |
| 2.24 | 2.24 | 94 | 73 | 27/5 | 30/0 | 12/2 |
| #10 2.24 | 0 | 100 | 92 | 15/5 | 92/83 | 80/67 |
| 2.24 | 2.24 | 100 | 96 | 17/8 | 98/87 | 85/80 |
| #12 2.24 | 0 | 100 | 96 | 30/5 | 98/96 | 27/20 |
| 2.24 | 2.24 | 100 | 97 | 35/3 | 89/80 | 20/12 |
| #16 2.24 | 0 | 65 | 62 | 32/13 | 91/93 | 63/47 |
| 2.24 | 2.24 | 53 | 70 | 32/8 | 94/87 | 38/42 | a = Observations taken at 20 days after treatment.
b = Observations taken at 33 days after treatment.
a* - Observations taken at 20 days after treatment, but no observations recorded at 33 days because plots were overgrown with morningglory and velvetleaf.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:

1. A method for reducing herbicide injury to a monocotyledonous crop plant due to application of a herbicidally-effective amount of a herbicide compound selected from the group consisting of thiocarbamates, triazines, acetamides and mixtures thereof, which method comprises applying to the plant locus a safening-effective amount of at least one antidote compound of the structural formula

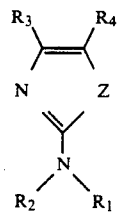

wherein Z is an oxygen atom or a sulfur atom; wherein each of $R_1$ and $R_2$ is independently selected from hydribo, alkyl, haloalkyl, hydroxyalkyl, monocycloalkyl, bicycloalkyl, tricycloalkyl, alkenyl, alkoxycarbonylalkyl, aryl and aralkyl, with the proviso that when Z is sulfur atom, $R_1$ and $R_2$ cannot both be hydrido; wherein each of $R_3$ and $R_4$ is independently selected from alkyl, alkoxy, hydroxyalkyl, alkoxyalkyl, haloalkyl, aryl, aralkyl, carboxylic acid derivatives and carbothioic acid derivatives selected from

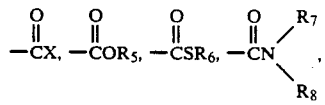

and oxazolyl or substituted oxazolyl of the formula

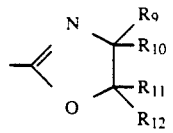

wherein X is halo, wherein each of $R_5$ and $R_6$ is independently selected from hydrido, alkyl and agriculturally-acceptable cations, alkoxyalkyl, aryl and aralkyl, wherein each of $R_7$ and $R_8$ is independently selected from hydrido, alkyl, hydroxyalkyl, alkoxyalkyl, aryl and aralkyl; wherein each of $R_1$ through $R_8$ is further independently selected from aryl and aralkyl substituted with one or more groups selected from alkyl, halo, haloalkyl, alkoxy, alkylthio, phenyl, phenoxy, phenylthio, dialkylamino, diphenylamino, cyano, nitro, carbamyl, acetamido and carboalkoxy; wherein each $R_9$ through $R_{12}$ is independently selected from hydrido, alkyl, hydroxyalkyl, alkoxy, alkoxyalkyl and halo; with the proviso that one of $R_3$ and $R_4$ must be selected from said carboxylic acid derivatives, said carbothioic acid derivatives, said oxazolyl and said substituted oxazolyl.

2. The method of claim 1 wherein said antidote compound is of the formula wherein each of $R_1$ and $R_2$ is independently selected from hydrido, methyl, ethyl, propyl, isopropyl, n-butyl, sec-butyl, tert-butyl, tert-pentyl, alkenyl of two to eight carbon atoms, cyclopentyl, phenyl and benzyl; wherein each of $R_3$ and $R_4$ is independently selected from trifluoromethyl, chlorophenyl, trifluoromethylphenyl,

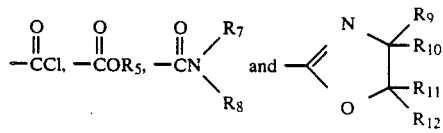

wherein $R_5$ is selected from hydrido, methyl, ethyl, benzyl, bromobenzyl and trifluoromethylbenzyl; $R_7$ is hydrido; $R_8$ is linear or branched hydroxyalkyl of two to five carbon atoms; and each of $R_9$ through $R_{12}$ is independently selected from hydrido, methyl and ethyl.

3. The method of claim 2 wherein said herbicide compound is selected from triallate, alachlor and butachlor, and said antidote compound is of the formula wherein each of R and Rz is independently selected from hydrido, methyl, ethyl, 1-methylethyl, 1,1-dimethylethyl, 1,1-dimethylpropyl, cyclopentyl, 2-propenyl and phenyl; $R_3$ is trifluoromethyl; $R_4$ is selected from

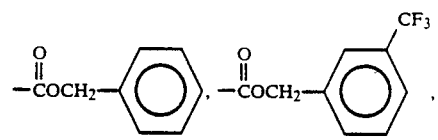

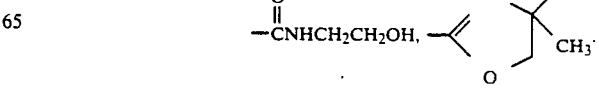

4. The method of claim 3 wherein said crop plant is grain sorghum and said herbicide is alachlor.

5. The method of claim 4 wherein said antidote compound is ethyl 2-[(1,1-dimethylethyl)amino]-4-(trifluoromethyl)-5-oxazolecarboxylate.

6. The method of claim 4 wherein said antidote compound is ethyl 2-[(1,1-dimethylethyl)methylamino]-4-(trifluoromethyl)-5-oxazolecarboxylate.

7. The method of claim 4 wherein said antidote compound is ethyl 2-[(1,1-dimethylethyl)amino]-4-(trifluoromethyl)-5-thiazolecarboxylate.

8. The method of claim 4 wherein said antidote compound is 2-[(1,1-dimethylethyl)amino]-4-(trifluoromethyl)-5-oxazolecarboxylic acid.

9. The method of claim 4 wherein said antidote compound is methyl 2-[(1,1-dimethylethyl)amino]-4-(trifluoromethyl)-5-oxazolecarboxylate.

10. The method of claim 4 wherein said antidote compound is 2-[(1,1-dimethylethyl)amino]-4-(trifluoromethyl)-5-oxazolecarbonyl chloride.

11. The method of claim 4 wherein said antidote compound is N-(1,1-dimethylethyl)-4,5-dihydro-4,4-dimethyl-4'-(trifluoromethyl)-2,5'-bioxazol-2'-amine.

12. The method of claim 4 wherein said antidote compound is ethyl 2-[(1,1-dimethylpropyl)amino]-4-(trifluoromethyl)-5-oxazolecarboxylate.

13. The method of claim 4 wherein said antidote compound is 2-[(1,1-dimethylethyl)amino]-4-(trifluoromethyl)-5-thiazolecarboxylic acid.

14. The method of claim 4 wherein said antidote compound is phenylmethyl 2-[(1,1-dimethylethyl)amino]-4-(trifluoromethyl)-5-thiazolecarboxylate.

15. The method of claim 4 wherein said antidote compound is ethyl 2-[(1-methylethyl)amino]-4-(trifluoromethyl)-5-thiazolecarboxylate.

16. The method of claim 4 wherein said antidote compound is 2-[(1,1-dimethylethyl)amino-N-(2-hydroxyethyl)-4-(trifluoromethyl)-5-oxazolecarboxamide.

17. The method of claim 4 wherein said antidote compound is 3-trifluoromethyl)phenyl]methyl 2-[(1,1-dimethylethyl)amino]-4-(trifluoromethyl) 5-oxazolecarboxylate.

18. The method of claim 2 wherein said crop plant is corn, said herbicide is selected from acetochlor and 2-chloro-2'-methyl-6'-methoxy-N-(isopropoxymethyl)acetanilide, and said antidote compound is of the formula wherein each of $R_1$ and $R_2$ is independently selected from hydrido, methyl, ethyl and 1,1-dimethylethyl; $R_3$ is trifluoromethyl; $R_4$ is selected from

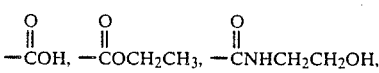

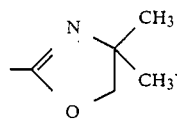

19. The method of claim 18 wherein said antidote compound is ethyl 2-(1,1-dimethylethyl)amino]-4-(trifluoromethyl)-5-oxazolecarboxylate.

20. The method of claim 18 wherein said antidote compound is ethyl 2-[(1,1-dimethylethyl)methylamino]-4-(trifluoromethyl)-5-oxazolecarboxylate.

21. The method of claim 18 wherein said antidote compound is ethyl 2-[(1,1-dimethylethyl)amino]-4-(trifluoromethyl)-5-thiazolecarboxylate.

22. The method of claim 18 wherein said antidote compound is N-(1,1-dimethyethyl)-4,5-dihydro-4,4-dimethyl-4'-(trifluoromethyl)-2,5'-bioxazol-2'-amine.

23. The method of claim 18 wherein said antidote compound is 2-[(1,1-dimethylethyl)amino]-4-(trifluoromethyl)-5-thiazolecarboxylic acid.

24. The method of claim 18 wherein said antidote compound is 2-[(1,1-dimethylethyl)amino]-N-(2-hydroxyethyl)-4-(trifluoromethyl)-5-oxazolecarboxamide.

25. The method of claim 2 wherein said herbicide compound is selected from the group of acetamide herbicide compounds consisting of:

2-chloro-2'-tert-butyl-6'-methyl-N-(methoxymethyl)acetanilide;

2-chloro-2',6'-diethyl-N-(methoxymethyl)acetanilide;

2-chloro-N-(isobutoxymethyl)-2'6-acetoxylidide;

2-chloro-2',6'-diethyl-N-(butoxymethyl)acetanilide;

2-chloro-N-(ethoxymethyl)-6'-ethyl-o-acetotoluidide;

2-chloro-N-(2,6-dimethyl-1-cyclohexen-1-yl)-N-(2-ethoxyethyl)acetamide;

2-chloro-N-(2-methoxy-1-methylethyl)-6'-ethyl-o-acetotoluidide;

2-chloro-2'-methyl-6'-methoxy-N-(isopropoxymethyl)acetanilide;

2-chloro-N-(2,6-dimethylphenyl)-N-(2-methoxyethyl)acetamide;

2-chloro-2'-methyl-6'-trifluoromethyl-N-(ethoxymethyl)acetanilide;

2-chloro-2'-methyl-6'-trifluoromethyl-N-(propoxymethyl)acetanilide;

2-chloro-2'-(3-methyl)butoxy-6'-methyl-N-(methyl)acetanilide;

2-chloro-2'-methyl-6'-propoxy-N-(methyl)acetanilide;

2-chloro-2'-butoxy-6'-methyl-N-(methyl)acetanilide;

2-chloro-N-(ethoxymethyl)-N-2-methyl-1-(1-methylethyl)-1-propenyl]acetanilide;

2-chloro-2'-ethyl-6'-(2-methylpropoxy)-N-(ethoxymethyl)acetanilide;

2-chloro-2'-methyl-6'-(1-methylbutoxy)-N-(methyl)acetanilide;

2-chloro-2'-ethyl-6'-(1-methylpropyl)-N-(methyl)acetanilide;

2-chloro-2'-(1,3-dimethylbutoxy)-6'-methyl-N-(methyl)acetanilide; and 2-chloro-2'-methyl-6'-(1-methylpropyl)-N-(methyl)acetanilide.

26. A combination of a herbicidally-effective amount of a herbicide compound selected from the group consisting of thiocarbamates, triazines, acetamides and mixtures thereof and a safening-effective amount of an antidote compound of the formula

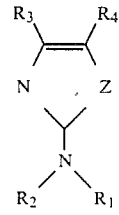

where Z is an oxygen atom or a sulfur atom; wherein each of $R_1$ and $R_2$ is independently selected from hydrido, alkyl, haloalkyl, hydroxyalkyl, monocycloalkyl, bicycloalkyl, tricycloalkyl, alkenyl, alkoxycarbonylalkyl, aryl and aralkyl, with the proviso that when Z is sulfur atom, $R_1$ and $R_2$ cannot both be hydrido; wherein each of $R_3$ and $R_4$ is independently selected from alkyl, alkoxy, hydroxyalkyl, alkoxyalkyl, haloalkyl, aryl, aralkyl, carboxylic acid derivatives and carbothioic acid derivatives selected from

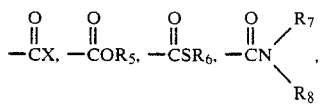

and oxazolyl or substituted oxazolyl of the formula

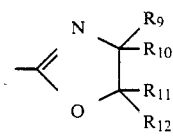

wherein X is halo, wherein each of $R_5$ and $R_6$ is independently selected from hydrido, alkyl and agriculturally-acceptable cations, alkoxyalkyl, arayl and aralkyl, wherein each of $R_7$ and $R_8$ is independently selected from hydrido, alkyl, hydroxyalkyl, alkoxyalkyl, aryl and aralkyl; wherein each of $R_1$ through $R_8$ is further independently selected from aryl and aralkyl substituted with one or more groups selected from alkyl, halo, haloalkyl, alkoxy, alkylthio, phenyl, phenoxy, phenylthio, dialkylamino, diphenylamino, cyano, nitro, carbamyl, acetamido and carboalkoxy; wherein each $R_9$ through $R_{12}$ is independently selected from hydrido, alkyl, hydroxyalkyl, alkoxy, alkoxyalkyl and halo; with the proviso that one of $R_3$ and $R_4$ must be selected from said carboxylic acid derivatives, said carbothioic acid derivatives, said oxazolyl and said substituted oxazolyl.

27. The combination of claim 26 wherein said antidote compound is of the formula wherein each of $R_1$ and $R_2$ is independently selected from hydrodo, methyl, ethyl, propyl, isopropyl, n-butyl, sec-butyl, tert-butyl, tert-pentyl, alkenyl of two to eight carbon atoms, cyclopentyl, phenyl and benzyl; wherein each of $R_3$ and $R_4$ is independently selected from trifluoromethyl, chlorophenyl, trifluoromethylphenyl,

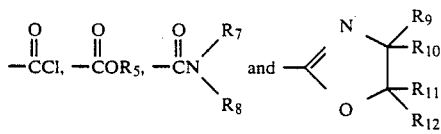

wherein $R_5$ is selected from hydrido, methyl, ethyl, benzyl, bromobenzyl and trifluoromethylbenzyl; $R_7$ is hydrido; $R_8$ is linear or branched hydroxyalkyl of two to five carbon atoms; and each of $R_9$ through $R_{12}$ is independently selected from hydrido, methyl and ethyl.

28. The combination of claim 27 wherein said herbicide compound is selected from triallate, alachlor and butachlor, and said antidote compound is of the formula wherein each of $R_1$ and $R_2$ is independently selected from hydrido, methyl, ethyl, 1-methylethyl, 1,1-dimethylethyl, 1,1-dimethylpropyl, cyclopentyl, 2-propenyl and phenyl; $R_3$ is trifluoromethyl; $R_4$ is selected from

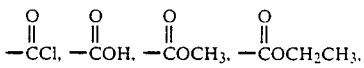

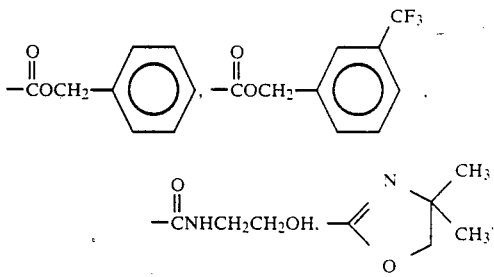

29. The combination of claim 28 wherein said herbicide is alachlor.

30. The combination of claim 29 wherein said antidote compound is ethyl 2-[(1,1-dimethylethyl)amino]-4-(trifluoromethyl)-5-oxazolecarboxylate.

31. The combination of claim 29 wherein said antidote compound is ethyl 2-[(1,1-dimethylethyl)methylamino]-4-(trifluoromethyl)-5-oxazolecarboxylate.

32. The combination of claim 29 wherein said antidote compound is ethyl 2-[(1,1-dimethylethyl)amino]-4-(trifluoromethyl)-5-thiazolecarboxylate.

33. The combination of claim 29 wherein said antidote compound is 2-[(1,1-dimethylethyl)amino]-4-(trifluoromethyl)-5-oxazolecarboxylic acid.

34. The combination of claim 29 wherein said antidote compound is methyl 2[(1,1-dimethylethyl)amino]-4-(trifluoromethyl)-5-oxazolecarboxylate.

35. The combination of claim 29 wherein said antidote compound is 2-[(1,1-dimethylethyl)amino]-4-(trifluoromethyl)-5-oxazolecarbonyl chloride.

36. The combination of claim 29 wherein said antidote compound is N-(1,1-dimethylethyl)-4,5-dihydro-4,4-dimethyl-4'-(trifluoromethyl)-2,5'-bioxazol-2-'amine.

37. The combination of claim 29 wherein said antidote compound is ethyl 2-[(1,1-dimethylpropyl)amino]-4-(trifluoromethyl)-5-oxazolecarboxylate.

38. The combination of claim 29 wherein said antidote compound is 2-[(1,1-dimethylethyl)amino]-4-(trifluoromethyl)-5-thiazolecarboxylic acid.

39. The combination of claim 29 wherein said antidote compound is phenylmethyl 2-[(1,1-dimethylethyl)amino]-4-(trifluoromethyl)-5-thiazolecarboxylate.

40. The combination of claim 29 wherein said antidote compound is ethyl 2-[(1-methylethyl)amino]-4-(trifluoromethyl)-5-thiazolecarboxylate.

41. The combination of claim 29 wherein said antidote compound is 2-[(1,1-dimethylethyl)amino]-N-(2-hydroxyethyl)-4-(trifluoromethyl)-5-oxazolecarboxamide.

42. The combination of claim 29 wherein said antidote compound is 3-(trifluoromethyl)phenyl]methyl 2-[(1,1-dimethylethyl)amino]-4-(trifluoromethyl)-5-oxazolecarboxylate.

43. The combination of claim 26 wherein said herbicide compound is selected from acetochlor and 2-chloro-2'-methyl-6'-methoxy-N-(isopropoxymethyl)acetanilide, and said antidote compound is of the formula wherein each of $R_1$ and $R_2$ is independently selected from hydrido, methyl, ethyl and 1,1dimethylehtyl; $R_3$ is trifluoromethyl; $R_4$ is selected from

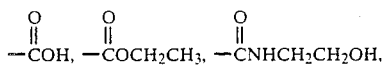

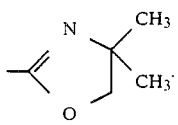

44. The combination of claim 43 wherein said antidote compound is ethyl 2-[(1,1-dimethylethyl)amino]-4-(trifluoromethyl)-5-oxazolecarboxylate.

45. The combination of claim 43 wherein said antidote compound is ethyl 2-[(1,1-dimethylethyl)methylamino]-4-(trifluoromethyl)-5-oxazolecarboxylate.

46. The combination of claim 43 wherein said antidote compound is ethyl 2-[(1,1-dimethylethyl)amino]-4-(trifluoromethyl)-5-thiazolecarboxylate.

47. The combination of claim 43 wherein said antidote compound is N-(1,1-dimethylethyl)-4,5-dihydro-4,4-dimethyl-4'-(trifluoromethyl)-2,5'-bioxazol-2'-amine.

48. The combination of claim 43 wherein said antidote compound is 2-[(1,1-dimethylethyl)amino]-4-(trifluoromethyl)-5-thiazolecarboxylic acid.

49. The combination of claim 43 wherein said antidote compound is 2-[(1,1-dimethylethyl)amino]-N-(2-hydroxyethyl)-4-(trifluoromethyl)-5-oxazolecarboxamide.

50. The combination of claim 26 wherein said herbicide compound is selected from the group of acetamide herbicide compounds consisting of:
   2-chloro-2'-tert-butyl-6'-methyl-N-(methoxymethyl)acetanilide;
   2-chloro-2',6'-diethyl-N-(methoxymethyl)acetanilide;
   2-chloro-N-(isobutoxymethyl)-2'6-acetoxylidide;
   2-chloro-2'6'-diethyl-N-(butoxymethyl)acetanilide;
   2-chloro-N-(ethoxymethyl)-6'-ethyl-o-acetotoluidide;
   2-chloro-N-(2,6-dimethyl-1-cyclohexen-1-yl)-N-(2-ethoxyethyl)acetamide;
   2-chloro-N-(2-methoxy-1-methylethyl)-6'-ethyl-o-acetotoluidide;
   2-chloro-2'-methyl-6'-methoxy-N-(isopropoxymethyl)acetanilide;
   2-chloro-N-(2,6-dimethylphenyl)-N-(2-methoxyethyl)acetamide;
   2-chloro-2'-methyl-6'-trifluoromethyl-N-(ethoxymethyl)acetanilide;
   2-chloro-2'-methyl-6'-trifluoromethyl-N-(propoxymethyl)acetanilide;
   2-chloro-2'-(3-methyl)butoxy-6'-methyl-N-(methyl)acetanilide;
   2-chloro-2'-methyl-6'-propoxy-N-(methyl)acetanilide;
   2-chloro-2'-butoxy-6'-methyl-N-(methyl)acetanilide;
   2-chloro-N-(ethoxymethyl)-N-2-methyl-1-(1-methylethyl)-1-propenyl]acetanilide;
   2-chloro-2'-ethyl-6'-(2-methylpropoxy)-N-(ethoxymethyl)acetanilide;
   2-chloro-2'-methyl-6'-(1-methylbutoxy)-N-(methyl)acetanilide;
   2-chloro-2'-ethyl-6'-(1-methylpropyl)-N-(methyl)acetanilide;
   2-chloro-2'-(1,3-dimethylbutoxy)-6'-methyl-N-(methyl)acetanilide; and
   2-chloro-2'-methyl-6'-(1-methylpropyl)-N-(methyl)acetanilide.

51. A combination comprising:
   2-chloro-2',6'-diethyl-N-(methoxymethyl)acetanilide and
   ethyl 2-[(1,1-dimethylethyl)amino]-4-(trifluoromethyl)-5-oxazolecarboxylate.

52. A combination comprising:
   2-chloro-N-(ethoxymethyl)-6'-ethyl-o-acetotoluidide and
   ethyl 2-[(1,1-dimethylethyl)amino]-4-(trifluoromethyl)-5-oxazolecarboxylate.

53. A combination comprising:
   2-chloro-2'-methyl-6'-methoxy-N-(isopropoxymethyl)acetanilide and
   ethyl 2-[(1,1-dimethylethyl)amino]-4-(trifluoromethyl)-5-oxazolecarboxylate.

54. A combination comprising:
   2-chloro-N-(2-methoxy-1-methylethyl)-6'-ethyl-o-acetotoluidide and
   ethyl 2-[(1,1-dimethylethyl)amino]-4-(trifluoromethyl)-5-oxazolecarboxylate.

55. Monocotyledonous crop seed, the plants grown from which are resistant to injury from a herbicide compound selected from the group consisting of thiocarbamates triazines, acetamides and mixtures thereof, said crop seed coated with a safening-effective amount of at least one antidote compound of the formula

wherein Z is an oxygen atom wherein each of $R_1$ and $R_2$ is independently selected from hydrido, alkyl, haloalkyl, hydroxyalkyl, monocycloalkyl, bicycloalkyl, tricycloalkyl, alkenyl alkoxycarbonylalkyl, aryl and aralkyl, with the proviso that when Z is sulfur atom, $R_1$ and $R_2$ cannot both be hydrido; wherein each of $R_3$ and $R_4$ is independently selected from alkyl, alkoxy, hydroxyalkyl, alkoxyalkyl, haloalkyl, aryl, aralkyl, carboxylic acid derivatives and carbothioic acid derivatives selected from

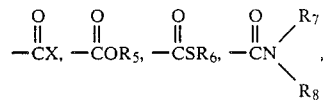

and oxazolyl or substituted oxazolyl of the formula

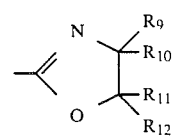

wherein X is halo, wherein each of $R_5$ and $R_6$ is independently selected from hydrido, alkyl and agriculturally-acceptable cations, alkoxyalkyl, aryl and aralkyl, wherein each of $R_7$ and $R_8$ is independently selected from hydrido, alkyl, hydroxyalkyl, alkoxyalkyl, aryl and aralkyl; wherein each of $R_1$ through $R_8$ is further independently selected from aryl and aralkyl substituted with one or more groups selected from alkyl, halo, haloalkyl, alkoxy, alkylthio, phenyl, phenoxy, phenylthio, dialkylamino, diphenylamino, cyano, nitro, carbamyl, acetamido and carboalkoxy; wherein each $R_9$ through $R_{12}$ is independently selected from hydrido, alkyl, hydroxyalkyl, alkoxy, alkoxyalkyl and halo; with the proviso that one of $R_3$ and $R_4$ must be selected from said carboxylic acid derivatives, said carbothioic acid derivatives, said oxazolyl and said substituted oxazolyl.

56. Crop seed of claim 55 wherein each antidote compound is of the formula wherein each of $R_1$ and $R_2$ is independently selected from hydrido, methyl, ethyl, propyl, isopropyl, n-butyl, sec-butyl, tert-butyl, tert-pentyl, alkenyl of two to eight carbon atoms, cyclopentyl, phenyl and benzyl; wherein each of $R_3$ and $R_4$ is independently selected from trifluoromethyl, chlorophenyl, trifluoromethylphenyl

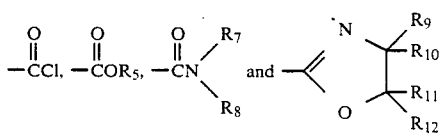

wherein $R_5$ is selected from hydrido, methyl, ethyl, benzyl, bromobenzyl and trifluoromethylbenzyl; $R_7$ is hydrido; $R_8$ is linear or branched hydroxyalkyl of two to five carbon atoms; and each of $R_9$ through $R_{12}$ is independently selected from hydrido, methyl and ethyl.

57. Crop seed of claim 56 wherein said herbicide compound is selected from triallate, alachlor and butachlor, and said antidote compound is of the formula wherein each of $R_1$ and $R_2$ is independently selected from hydrido, methyl, ethyl, 1-methylethyl, 1,1-dimethylethyl, 1,1-dimethylpropyl, cyclopentyl, 2-propenyl and phenyl; $R_3$ is trifluoromethyl; $R_4$ is selected from

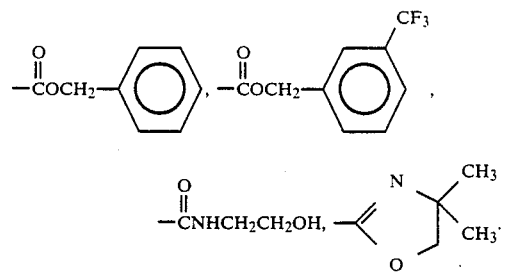

58. Crop seed of claim 57 wherein said crop plant is grain sorghum and said herbicide is alachlor.
59. Crop seed of claim 57 wherein said antidote compound is ethyl 2-[(1,1-dimethylethyl)amino]-4-(trifluoromethyl)-5-oxazolecarboxylate.
60. Crop seed of claim 57 wherein said antidote compound is ethyl 2-[(1,1-dimethylethyl)methylamino]-4-(trifluoromethyl)-5-oxazolecarboxylate.
61. Crop seed of claim 57 wherein said antidote compound is ethyl 2-[(1,1-dimethylethyl)amino]-4-(trifluoromethyl)-5-thiazolecarboxylate.
62. Crop seed of claim 57 wherein said antidote compound is 2-[(1,1-dimethylethyl)amino]-4-(trifluoromethyl)-5-oxazolecarboxylic acid.
63. Crop seed of claim 57 wherein said antidote compound is methyl 2-[(1,1-dimethylethyl)amino]-4-(trifluoromethyl)-5-oxazolecarboxylate.
64. Crop seed of claim 57 wherein said antidote compound is 2-[(1,1-dimethylethyl)amino]-4-(trifluoromethyl)-5-oxazolecarbonyl chloride.
65. Crop seed of claim 57 wherein said antidote compound is N-(1,1-dimethylethyl)-4,5-dihydro-4,4-dimethyl-4'-(trifluoromethyl)-2,5'-bioxazol-2'-amine.
66. Crop seed of claim 57 wherein said antidote compound is ethyl 2-[(1,1-dimethylpropyl)amino]-4-(trifluoromethyl)-5-oxazolecarboxylate.
67. Crop seed of claim 57 wherein said antidote compound is 2-[(1,1-dimethylethyl)amino]-4-(trifluoromethyl)-5-thiazolecarboxylic acid.
68. Crop seed of claim 57 wherein said antidote compound is phenylmethyl 2-[(1,1-dimethylethyl)amino]-4-(trifluoromethyl)-5-thiazolecarboxylate.
69. Crop seed of claim 57 wherein said antidote compound is ethyl 2-[(1-methylethyl)amino]-4-(trifluoromethyl)-5-thiazolecarboxylate.
70. Crop seed of claim 57 wherein said antidote compound is 2-[(1,1-dimethyethyl)amino]-N-(2-hydroxyethyl)-4-(trifluoromethyl)-5-oxazolecarboxamide.
71. Crop seed of claim 57 wherein said antidote compound is [3-trifluoromethyl)phenyl]methyl 2-[(1,1-dimethylethyl)amino]-4-(trifluoromethyl) 5-oxazolecarboxylate.
72. Crop seed of claim 56 wherein said herbicide is selected from acetochlor and 2-chloro-2'-methyl-6'-methoxy-N-(isopropoxymethyl)acetanilide, and said antidote compound is of the formula wherein each of $R_1$ and $R_2$ is independently selected from hydrido, methyl, ethyl and 1,1-dimethylethyl; $R_3$ is trifluoromethyl; $R_4$ is selected from

73. Crop seed of claim 72 wherein said antidote compound is ethyl 2-[(1,1-dimethylethyl)amino]-4-(trifluoromethyl)-5-oxazolecarboxylate.
74. Crop seed of claim 72 wherein said antidote compound is ethyl 2-[(1,1-dimethylethyl)methylamino]-4-(trifluoromethyl)-5-oxazolecarboxylate.
75. Crop seed of claim 72 wherein said antidote compound is ethyl 2-[(1,1-dimethylethyl)amino]-4-(trifluoromethyl)-5-thiazolecarboxylate.
76. Crop seed of claim 72 wherein said antidote compound is N-(1,1-dimethylethyl)-4,5-dihydro-4,4-dimethyl-4'-(trifluoromethyl)-2,5'-bioxazol2'-amine.
77. Crop seed of claim 72 wherein said antidote compound is 2-[(1,1-dimethylethyl)amino]-4-(trifluoromethyl)-5-thiazolecarboxylic acid.
78. Crop seed of claim 72 wherein said antidote compound is 2-[(1,1-dimethylethyl)amino]-N-(2-hydroxyethyl)-4-(trifluoromethyl)-5-oxazolecarboxamide.

* * * * *